(12) United States Patent
Cohen et al.

(10) Patent No.: US 9,598,383 B2
(45) Date of Patent: Mar. 21, 2017

(54) REACTIVE OXYGEN SPECIES-BASED PRODRUGS

(71) Applicant: The Regents of the University of California, Oakland, CA (US)

(72) Inventors: Seth M. Cohen, La Jolla, CA (US); Jean-Philippe Monserrat, La Jolla, CA (US); Christian Perez, La Jolla, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/316,427

(22) Filed: Jun. 26, 2014

(65) Prior Publication Data

US 2015/0005352 A1    Jan. 1, 2015

Related U.S. Application Data

(60) Provisional application No. 61/839,704, filed on Jun. 26, 2013.

(51) Int. Cl.
*C07D 277/14* (2006.01)

(52) U.S. Cl.
CPC ................... *C07D 277/14* (2013.01)

(58) Field of Classification Search
CPC .................................................. C07D 277/14
USPC ........................................................ 548/188
See application file for complete search history.

(56) References Cited

FOREIGN PATENT DOCUMENTS

WO    WO-00/61549 A2 * 10/2000

OTHER PUBLICATIONS

Shaye et al., Tetrahedron: Asymmetry (available online Mar. 30, 2011), 22(4), pp. 439-463.*
Bigot et al., Journal of the American Chemical Society (Aug. 17, 2011), 133(35), pp. 13778-13781.*
Benoit et al., Tetrahedron: Asymmetry, May 16, 2008, 19(9), pp. 1068-1077.*
Shaye et al., Synlett, 2009, 6, pp. 960-964.*
Chang et al., Journal of the Chinese Chemical Society, 1990, 37(6), pp. 577-582.*
Chauvin et al., Journal of Organic Chemistry, 1993, 58(8), pp. 2291-2295.*
Chemical Abstracts Registry No. 71904-69-3, indexed in the Registry file on STN CAS Online Nov. 16, 1984.*
Cao, S. et al. (2012). "ROS-Inducible DNA Cross-Linking Agent as a New Anticancer Prodrug Building Block," *Chem. Eur. J.* 18:3850-3854.
Charkoudian, L.K. et al. (Nov. 21, 2007, e-published Sep. 19, 2007). "Modifications of boronic ester pro-chelators triggered by hydrogen peroxide tune reactivity to inhibit metal-promoted oxidative stress," *Dalton Trans* 43:5031-5042.
Daniel, K.B. et al. (Feb. 2011, e-published Nov. 4, 2010). Activation of sulfonate ester based matrix metalloproteinase proinhibitors by hydrogen peroxide, *J Biol Inorg Chem* 16(2):313-323.
Evans, D.A. et al. (1987). "Contrasteric Carboximide Hydrolysis with Lithium Hydroperoxide," *Tet. Lett.* 28(49):6141-6144.
Hsieh, P.W. et al. (2009). "Current prodrug design for drug discovery," *Curr Pharm Des* 15(19):2236-2250.
Kratz, F. et al. (Jan. 2008). "Prodrug strategies in anticancer chemotherapy," *ChemMedChem* 3(1):20-53.
Kurumbail, R.G. et al. (Dec. 19-26, 1996). "Structural basis for selective inhibition of cyclooxygenase-2 by anti-inflammatory agents," *Nature* 384(6610):644-648.
Lopez-Lazaro, M. et al. (Jul. 8, 2007, e-published Dec. 5, 2006). "Dual role of hydrogen peroxide in cancer: possible relevance to cancer chemoprevention and therapy," *Cancer Lett* 252(1):1-8.
Major Jourden, J.L. et al. (Sep. 10, 2010). "Hydrogen peroxide activated matrix metalloproteinase inhibitors: a prodrug approach," *Angew Chem Int Ed Engl* 49(38):6795-6797.
Major Jourden, J.L. et al. (Jul. 28, 2011, e-published Jun. 16, 2011). "Investigation of self-immolative linkers in the design of hydrogen peroxide activated metalloprotein inhibitors," *Chem Commun* 47(28):7968-7970.
Nagata, M. (Aug. 2005). "Inflammatory cells and oxygen radicals," *Curr Drug Targets Inflamm Allergy* 4(4):503-504.
Pelicano, H. et al. (Apr. 2004). "ROS stress in cancer cells and therapeutic implications," *Drug Resist Updat* 7(2):97-110.
Watermeyer, J.M. et al. (Apr. 28, 2010). "Characterization of domain-selective inhibitor binding in angiotensin-converting enzyme using a novel derivative of Lisinopril," *Biochem J* 428(1):67-74.

* cited by examiner

*Primary Examiner* — Laura L Stockton
(74) *Attorney, Agent, or Firm* — Mintz Levin Cohn Ferris Glovsky and Popeo, P.C.

(57) ABSTRACT

Provided herein are ROS-sensitive prodrug compositions and methods of treating ROS-associated diseases by administering the ROS-sensitive prodrug compositions.

4 Claims, 10 Drawing Sheets

REACTIVE OXYGEN SPECIES-BASED PRODRUGS

CROSS-REFERENCES TO RELATED APPLICATIONS

This application claims the benefit of U.S. Provisional Application No. 61/839,704, filed Jun. 26, 2013 which is hereby incorporated by reference in its entirety and for all purposes.

STATEMENT AS TO RIGHTS TO INVENTIONS MADE UNDER FEDERALLY SPONSORED RESEARCH AND DEVELOPMENT

This invention was made with Government support under grant number GM098435 awarded by the National Institutes of Health. The Government has certain rights in the invention.

BACKGROUND OF THE INVENTION

Prodrug strategies often serve to improve the drug-like properties of bioactive molecules such as bioavailability, cell permeability and toxicity. Prodrugs can further aid in overcoming barriers typically encountered in drug formulation. Indeed, many global-marketed therapeutics indicate the success of prodrugs and their use and demand. Prodrugs often use a chemical modification that renders the active-drug, inactive or less active. However, removing and targeting prodrugs to specific locations requires specific manipulation to allow efficient in-vivo removal of the chemical modification in a specified location. One common approach to facilitate in-vivo removal is catalysis by an esterase. This approach involves esterification of an acid moiety, which can then become hydrolyzed in vivo by ubiquitous esterases. These approaches suffer from non-specificity because esterases are ubiquitous and constitutively active. There is a need in the art to provide prodrugs which include specificity to the disease and target of the indication. Provided herein are solutions to these and other problems in the art.

BRIEF SUMMARY OF THE INVENTION

Provided herein are prodrugs sensitive to ROS as defined herein.

Provided herein are compounds having the formula:

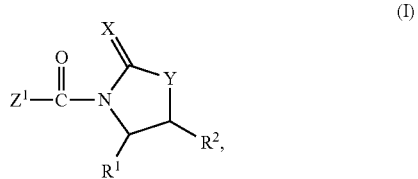

(I)

In formula (I), —C(O)Z$^1$ together form a drug moiety. X and Y are independently —S— or —O—. R$^1$ is independently hydrogen, halogen, —CCl$_3$, —CBr$_3$, —CF$_3$, —CI$_3$, —CN, —SR$^6$, —SO$_2$Cl, —SO$_{n1}$R$^6$, SO$_{v1}$NR$^3$R$^4$, —NHNH$_2$, —ONR$^3$R$^4$, —NHC(O)NHNH$_2$, —NHC(O)NR$^3$R$^4$, —N(O)$_{m1}$, —NR$^3$R$^4$, —C(O)R$^5$, —C(O)—OR$^5$, —C(O)NR$^3$R$^4$, —OR$^6$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. R$^2$ is independently hydrogen, halogen, —CCl$_3$, —CBr$_3$, —CF$_3$, —CI$_3$, —SR$^{10}$, —CN, —SO$_2$Cl, —SO$_{n2}$R$^{10}$, —SO$_{v2}$NR$^7$R$^8$, —NHNH$_2$, —ONR$^7$R$^8$, —NHC(O)NHNH$_2$, —NHC(O)NR$^7$R$^8$, —N(O)$_{m2}$, —NR$^7$R$^8$, —C(O)R$^9$, —C(O)—OR$^9$, —C(O)NR$^7$R$^8$, —OR$^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. R$^3$, R$^4$, R$^5$, R$^6$, R$^7$, R$^8$, R$^9$ and R$^{10}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n1 and n2 are independently an integer from 0 to 4. The symbols m1 and m2 are independently an integer from 1 to 2. The symbols v1 and v2 are independently an integer from 1 to 2.

Provided herein are pharmaceutical compositions. In one aspect is a pharmaceutical composition which includes a pharmaceutically acceptable excipient and a compound as described herein, including embodiments thereof.

Also provided herein are methods of treating a ROS-associated disease in a subject in need thereof. In one aspect, is a method of treating cancer associated with ROS by administering a therapeutically effective amount of a compound of formula (I) or a compound as described herein, including embodiments thereof. In another aspect, is a method of treating neurodegenerative disease associated with ROS by administering a therapeutically effective amount of a compound of formula (I) or a compound as described herein, including embodiments thereof. In yet another aspect, is a method of treating inflammation associated with ROS by administering a therapeutically effective amount of a compound of formula (I) or a compound as described herein, including embodiments thereof. In still another aspect, is a method of treating fibrosis associated with ROS by administering a therapeutically effective amount of a compound of formula (I) or a compound as described herein, including embodiments thereof. In another aspect, is a method of treating cardiovascular disease associated with ROS by administering a therapeutically effective amount of a compound of formula (I) or a compound as described herein, including embodiments thereof.

DETAILED DESCRIPTION OF THE INVENTION

Figure 1:
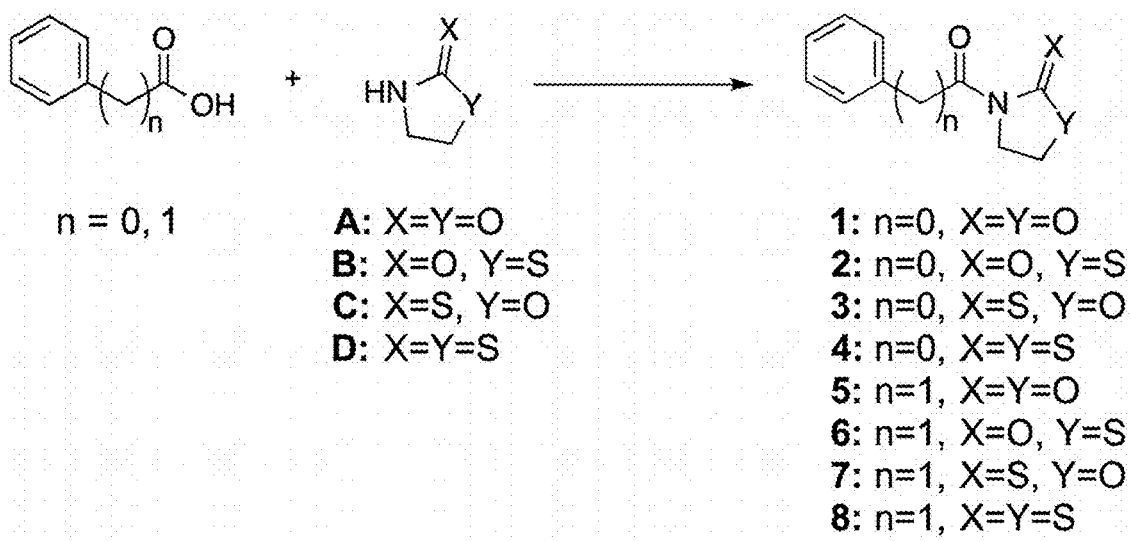
FIG. 1 Model compounds demonstrating prodrug moiety removal conditions.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multi-valent radicals, having the number of carbon atoms designated (i.e., $C_1$-$C_{10}$ means one to ten carbons). An "alkyl" is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. A heteroalkyl is not cyclized. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, —CH═CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, refers to a moiety with formula, —C(O)R, where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as B, N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include boron (B), oxygen (O), nitrogen (N), sulfur (S), phosphorus (P), and silicon (Si).

A "substituent group," as used herein, means a group selected from the following moieties:
(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

The reactive functional groups can be chosen such that they do not participate in, or interfere with, the chemical stability of the conjugate described herein. Alternatively, a reactive functional group can be protected from participating in the crosslinking reaction by the presence of a protecting group.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. Alternatively, at least one or all of these groups are substituted with at least one lower substituent group.

In other embodiments of the compounds herein, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and/or each substituted or unsubstituted heterocycloalkyl is a substituted or unsubstituted 5 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_5$-$C_7$ cycloalkylene, and/or each substituted or unsubstituted heterocycloalkylene is a substituted or unsubstituted 5 to 7 membered heterocycloalkylene. In some embodiments, the compound is a chemical species set forth in the Examples section below.

The term "pharmaceutically acceptable salts" is meant to include salts of the compounds disclosed herein that are prepared with acids or bases, depending on the particular substituents found on the compounds. When compounds of the present invention contain relatively acidic functionalities, base addition salts can be obtained by contacting the neutral form of such compounds with a sufficient amount of the desired base, either neat or in a suitable inert solvent. Examples of acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with acceptable acids or bases. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art. As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

A "prodrug," as used herein, refers to an pharmacological substance having biological (e.g. pharmacological) activity or increased biological activity upon undergoing a chemical reaction. The prodrugs herein may be activated upon contacting the prodrug with a chemical capable of breaking the covalent bond (e.g. through hydrolysis) between the carboxyl of the drug moiety and the nitrogen of the prodrug moiety as described herein, such as an ROS. Thus a prodrug may be a less active pharmacological substance that becomes more active upon undergoing the activating chemical reaction (e.g. upon contact with a ROS). A prodrug may have little or no activity and become active upon undergoing the activating chemical change. A prodrug includes a prodrug moiety and a drug moiety. A "prodrug moiety," is a portion of a prodrug that is modified or removed (either partially or wholly) when the prodrug undergoes the activating chemical reaction (e.g. thereby producing an carboxylate drug). Thus, the prodrug moiety is typically responsible for the inactivity, or reduced activity, of the prodrug (e.g. the prodrug moiety masks the activity of the drug moiety until it is removed from the prodrug). The "drug moiety" is a portion of the prodrug which is substantially inactive when covalently linked to the remainder of the prodrug but is an active drug when not covalently linked to the remainder of the prodrug. The drug moiety disclosed herein may contain a carboxyl group point of attachment to the remainder of the prodrug which becomes a carboxylate moiety of the drug upon disruption (e.g. cleavage or hydrolysis) of the covalent bond. In its active form, the drug is typically useful in the treatment, cure, or prevention of a disease or condition, or used to otherwise enhance the physical or mental well-being of an organism, such as a human). Thus, the drug moiety may be derived from carboxylate drugs useful in treating diseases associated with ROS activity. A drug moiety may be a non-steroidal anti-inflammatory drug moiety, a histone deacetylase inhibitor drug moiety, a statin drug moiety, a leukotriene receptor antagonist drug moiety, a fluoroquinolone drug moiety, a matrix metalloproteinase inhibitor drug moiety, cardiovascular therapy drug moiety (e.g. ACE inhibitor drug moiety or ARB drug moiety), or an antifolate drug moiety.

A "carboxylate drug" is an active pharmacological substance (e.g., any chemical substance, including organic molecules and inorganic molecules and combinations thereof, useful in the treatment, cure, or prevention of a disease or condition, or used to otherwise enhance the physical or mental well-being of an organism, such as a human). As used herein, a carboxylate drug refers to the compound having a carboxylic acid moiety formed upon removal of the prodrug moiety. As used herein, the term "drug," "medicine," and "medication" are interchangeable. The carboxylate drug may be a non-steroidal anti-inflammatory drug, a histone deacetylase inhibitor drug, a statin drug, a leukotriene receptor antagonist drug, a fluoroquinolone drug, a matrix metalloproteinase inhibitor drug, cardiovascular therapy drug (e.g. ACE inhibitor drug or ARB drug), or an antifolate drug. The term "inactive" as used herein in the context of a prodrug moiety means substantially inactive, completely inactive or relatively inactive as compared to the free drug not attached to the prodrug moiety.

A "non-steroidal anti-inflammatory drug moiety" or "NSAID moiety" as used herein refers to the inactive form of a compound covalently linked to a prodrug moiety that upon activation (i.e. removal of a prodrug moiety) reduces inflammation. A NSAID moiety may be an inactive compound which upon activation (i.e. removal of the prodrug moiety) inhibits the protein cyclooxygenase and may herein be referred to as a "cyclooxygenase inhibitor drug moiety" or "COX inhibitor drug moiety". A COX inhibitor drug moiety may be a salicylate drug moiety or a salicylate drug moiety analogue such as, for example, an acetylsalicylic acid drug moiety, a diflunisal drug moiety, a salsalate drug moiety, or a choline magnesium trisalicylate drug moiety. A COX inhibitor drug moiety may be a "propionic acid COX inhibitor drug moiety" (e.g. a COX inhibitor drug moiety having a propionic acid functional groups). Exemplary propionic acid COX inhibitor drug moieties include ibuprofen drug moiety, a dexibuprofen drug moiety, a naproxen drug moiety, a fenoprofen drug moiety, a ketoprofen drug moiety, a dexketoprofen drug moiety, a flurbiprofen drug moiety, an oxaprozin drug moiety, or a loxoprofen drug moiety, including analogues thereof. A COX inhibitor drug moiety may be a "acetic acid COX inhibitor drug moiety" (e.g. a COX inhibitor drug moiety having an acetic acid functional group). Exemplary acetic acid COX inhibitor drug moieties include indomethacin drug moiety, a tolmetin drug moiety, a sulindac drug moiety, an etodolac drug moiety, a ketorolac drug moiety, a diclofenac drug moiety, or and aceclofenac, including analogues thereof. A COX inhibitor drug moiety may be a "anthranilic acid COX inhibitor drug moiety" (e.g. a COX inhibitor drug moiety having an anthranilic acid functional group). Exemplary anthranilic acid COX inhibitor drug moieties include a mefenamic acid drug moiety, a meclofenamic acid drug moiety, a flufenamic acid drug moiety, or a tolfenamic acid drug moiety, including analogues thereof.

A "non-steroidal anti-inflammatory drug" or "NSAID" is a drug that provides analgesic, antipyretic or anti-inflammatory effects. A NSAID as used herein refers to the carboxylate drug of NSAID moieties described herein.

A "histone deacetylase inhibitor drug moiety" or "HDAC inhibitor drug moiety" as used herein refers to the inactive form of a compound covalently linked to a prodrug moiety that upon activation (i.e. removal of a prodrug moiety) inhibits at least one of the activity of histone deacetylase. A HDAC inhibitor drug moiety may be a "Class I HDAC inhibitor drug moiety" (i.e. a HDAC inhibitor drug moiety which inhibits HDAC1, -2, -3, or -8); a "Class II HDAC inhibitor drug moiety" (i.e. a HDAC inhibitor drug moiety which inhibits HDAC5, -6, -7, -9, or -10); a "Class III HDAC inhibitor drug moiety" (i.e. a HDAC inhibitor drug moiety which inhibits SIRT1-7) or a "Class IV HDAC inhibitor drug moiety" (i.e. a HDAC inhibitor drug moiety which inhibits HDAC 11). Exemplary HDAC inhibitor drug moieties include a phenylbutyric acid drug moiety or a valproic acid drug moiety.

A "histone deacetylase inhibitor drug" or "HDAC inhibitor drug" is a drug that inhibits at least one of the activity of histone deacetylase and which is covalently linked to a prodrug moiety. A HDAC inhibitor drug as used herein refers to the carboxylate drug of the HDAC inhibitor drug moieties described herein.

A "statin drug moiety" as used herein refers to the inactive form of a compound covalently linked to a prodrug moiety that upon activation (i.e. removal of a prodrug moiety) inhibits HMG-CoA reductase. Exemplary statin drug moieties include an atorvastatin drug moiety, a cerivastatin drug moiety, a fluvastatin drug moiety, a pitavastatin drug moiety, or a rosuvastatin drug moiety, including analogues thereof.

A "statin drug" as used herein refers to a compound that inhibits HMG-CoA reductase. A statin drug as used herein refers to the carboxylate drug of the statin drug moieties described herein.

A "leukotriene receptor antagonist drug moiety" or "LTRA drug moiety" as used herein refers to the inactive form of a compound covalently linked to a prodrug moiety that upon activation (i.e. removal of a prodrug moiety) inhibits binding of a leukotriene compound to its cognate receptor. Exemplary LTRA drug moieties include a montelukast drug moiety and its carboxylate-analogues.

A "leukotriene receptor antagonist drug" or "LTRA drug" as used herein refers to a compound that inhibits binding of a leukotriene compound to its cognate receptor. A LTRA drug as used herein refers to the carboxylate drug of the LTRA drug moieties described herein.

A "fluoroquinolone drug moiety" refers to the inactive form of fluorinated analogues of quinolone, that is covalently linked to a prodrug moiety which upon activation (i.e. removal of a prodrug moiety) possess antibacterial activity. Exemplary fluoroquinolone drug moieties include a ciprofloxin drug moiety, a balofloxacin drug moiety, a grepafloxacin drug moiety, a levofloxacin drug moiety, a pazufloxacin drug moiety, a sparfloxacin drug moiety, a temafloxacin drug moiety, a tosufloxacin drug moiety, a clinafloxacin drug moiety, a gatifloxacin drug moiety, a gemifloxacin drug moiety, a moxifloxacin drug moiety, a sitafloxacin drug moiety, a trovafloxacin drug moiety, a prulifloxacin drug moiety, a delafloxacin drug moiety, a JNJ-Q2 drug moiety, or a nemonoxacin drug moiety, including carboxylate-analogues thereof.

A "fluoroquinolone drug" as used herein, refers to fluorinated analogues of quinolone having antibacterial drug activity. A fluoroquinolone drug as used herein refers to the carboxylate drug of the fluoroquinolone drug moieties described herein.

A "matrix metalloproteinase inhibitor drug moiety" or "MMP inhibitor drug moiety" as used herein refers to the inactive form of a compound covalently linked to a prodrug moiety that upon activation (i.e. removal of a prodrug moiety) inhibits a MMP. A MMP inhibitor drug moiety may inhibit MMP1, MMP2, MMP3, or MMP9. Exemplary MMP inhibitor drug moieties include "sulfonamide-based MMP inhibitor drug moieties" (i.e. compounds that inhibit MMP and include a sulfonamide functional group (e.g. arylsulfonamides, cyclic sulfonamides)).

A "matrix metalloproteinase inhibitor drug" or "MMP inhibitor drug" as used herein refers to a compound that inhibits a MMP. A MMP inhibitor drug as used herein refers to the carboxylate drug of the MMP inhibitor drug moieties described herein.

A "cardiovascular therapy drug moiety" refers to the inactive form of a compound covalently linked to a prodrug moiety that upon activation (i.e. removal of a prodrug moiety) treats cardiovascular disease or its associated disease. Exemplary cardiovascular therapy drug moieties include, for example, a "Angiotensin Converting Enzyme Inhibitor drug moiety" or "ACE inhibitor drug moiety" such as a enalapril drug moiety, a ramipril drug moiety, a quinapril drug moiety, a perindopril drug moiety, a lisinopril drug moiety, a benazepril drug moiety, an imidapril drug moiety, a trandolapril drug moiety, or a cilazapril drug moiety; or a "Angiotensin Receptor Blocker drug moiety" or "ARB drug moiety" such as a valsartan drug moiety, a telmisartan drug moiety, an azilsartan drug moiety, or an olmesartan drug moiety.

A "cardiovascular therapy drug" refers to a compound which treats cardiovascular disease or its associated disease. A cardiovascular therapy drug may be a "Angiotensin Converting Enzyme Inhibitor drug" or "ACE inhibitor drug"; or a "Angiotensin Receptor Blocker drug" or "ARB drug". An ACE inhibitor drug and ARB drug, as used herein refer respectively to the carboxylate drug of the ACE inhibitor drug moieties and ARB drug moieties described herein.

A "furosemide drug moiety" as used herein refers to the inactive form of furosemide and its analogues that is covalently linked to a prodrug moiety that upon activation (i.e. removal of a prodrug moiety) treats hypertension or edema.

A "furosemide drug" or "furosemide" as used herein refers to a compound that treats hypertension or edema and is the active form of the furosemide drug moieties or furosemide analogue drug moieties described herein.

Retinoic acid is used according to its plain and ordinary meaning and includes retinoic acid analogues having a carboxylate moiety. A "retinoic acid drug moiety" as used herein refers to an inactive retinoic acid covalently linked to a prodrug moiety that upon activation releases the active form of retinoic acid.

An "anti-cancer drug moiety" as used herein refers to the inactive form of a compound covalently linked to a prodrug moiety that upon activation (i.e. removal of a prodrug moiety) inhibits the growth or proliferation of cells.

An "anti-cancer drug" as used herein refers to a compound which has a carboxylate that treats cancer by inhibiting the growth or proliferation of cells (i.e. anti-neoplastic properties). An anti-cancer drug may be chemotherapeutic. An anti-cancer drug may be approved by the FDA or similar regulatory agency of a country other than the USA, for treating cancer.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "⁓" denotes the point of attachment of a chemical moiety to the remainder of a molecule or chemical formula.

Moreover, where a moiety is substituted with an R substituent, the group may be referred to as "R-substituted." Where a moiety is R-substituted, the moiety is substituted with at least one R substituent and each R substituent is optionally different (i.e. independently substituted). Where a particular R group is present in the description of a chemical genus (such as Formula (I)), a Roman alphabetic symbol may be used to distinguish each appearance of that particular R group. For example, where multiple $R^3$ substituents are present, each $R^3$ substituent may be distinguished as $R^{3A}$, $R^{3B}$, $R^{3C}$, $R^{3D}$, etc., wherein each of $R^{3A}$, $R^{3B}$, $R^{3C}$, $R^{3D}$, etc. is defined within the scope of the definition of $R^3$ and optionally differently.

Description of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "peptide," "polypeptide," and "protein" are used interchangeably herein to refer to a polymer of amino acid residues.

The term "peptidyl" and "peptidyl moiety" means a monovalent peptide.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. An oligomer comprising amino acid mimetics is a peptidomimetic. A peptidomimetic moiety is a monovalent peptidomimetic.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)). In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions. In some embodiments, there may be 1, 2, 3, 4, 5, 6, 7, 8, 9, 10, 15, 20, 25, 30, 35, or 40 conservative substitutions.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

A nucleic acid (such as a polynucleotide), a polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters as known in the art, for example BLAST or BLAST 2.0. For example, comparison can be conducted, e.g., by the local homology algorithm of Smith & Waterman, 1981, *Adv. Appl. Math.* 2:482, by the Homology Alignment Algorithm of Needleman & Wunsch, 1970, *J. Mol. Biol.* 48:443, by the search for similarity method of Pearson & Lipman, 1988, *Proc. Nat'l. Acad. Sci. USA* 85:2444, or by computerized implementations of these algorithms (GAP, BESTFIT, FASTA, and TFASTA in the Wisconsin Genetics Software Package, Genetics Computer Group, 575 Science Dr., Madison, Wis.). Thus alignment can be carried out for sequences that have deletions and/or additions, as well as those that have substitutions, as well as naturally occurring, e.g., polymorphic or allelic variants, and man-made variants.

The phrase "substantial sequence identity" or "substantial identity," in the context of two polypeptide sequences, refers to a sequence that has at least 70% identity to a reference sequence. Percent identity can be any integer from 70% to 100%. Two polypeptide sequences that have 100% sequence identity are said to be "identical." A polypeptide sequence is said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, or at least 99% or greater sequence identity as determined using the methods described herein, such as BLAST using standard parameters as described above.

The term "expression" includes any step involved in the production of the polypeptide including, but not limited to, transcription, post-transcriptional modification, translation, post-translational modification, and secretion.

An amino acid or peptide is "heterologous" to another sequence with which it is operably linked if the two sequences are not associated in nature.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853). The methods above may be used to synthesize single molecular species for incorporation into a prodrug.

The term "reactive oxygen species" or "ROS", as used herein, is a molecule comprising a reactive oxygen having unpaired valence shell electrons. A "ROS" generally refers to free radicals, reactive anions containing oxygen atoms, or molecules containing oxygen atoms that can either produce free radicals or are chemically activated by them. Accordingly, reactive oxygen species may include, without limitation, superoxide radicals, hydrogen peroxide, peroxynitrite (e.g. ONOO−), lipid peroxides, hydroxyl radicals, thiyl radicals, superoxide anion, organic hydroperoxide, RO.alkoxy and ROO.peroxy radicals, and hypochlorite (OCl−). Accumulating oxidative damage may also affect the efficiency of mitochondria and further increase the rate of ROS production.

The term "metal binding moiety", as used herein, is a drug moiety that forms an active, or more active, metal binding drug upon modification or removal of the prodrug moiety. A metal binding drug is a drug that is capable of coordinating one or more metal atoms.

The term "zinc binding moiety", as used herein, is a metal binding moiety that forms an active, or more active, zinc binding drug upon modification or removal of the prodrug moiety. A zinc binding drug is a drug that is capable of coordinating one or more zinc atoms. (e.g. a zinc atom necessary for a protein's function).

The term "carbohydrate", as used herein, is used herein according to its plain ordinary meaning and refers to a molecule consisting of carbon, hydrogen and oxygen. "Saccharide" is used interchangeably with "carbohydrate". Carbohydrates include monosaccharides, for example glucose, and ribose, and polysaccharides. A "carbohydrate moiety", as used herein, is a monovalent carbohydrate. A carbohydrate or a carbohydrate moiety may be unsubstituted or it may be substituted with the substituents described herein.

The term "oxidatively-sensitive prodrug", as used herein, is a prodrug having a prodrug moiety that is modified or removed in the presence of an oxidative compound. An "oxidative compound" is a chemical compound that has the ability to oxidize other substances (e.g. a reactive oxygen species such as hydrogen peroxide).

The term "metalloprotein", as used herein, is a protein that is coordinated to at least one metal atom. The term "metalloenzyme", as used herein, is a metalloprotein in which the coordinated metal atom participates in a reaction catalyzed by the metalloenzyme.

The term "metalloprotease" or "metalloproteinase", as used herein, is a protease enzyme that coordinates a metal atom in the protease active site and the metal atom, often zinc or cobalt, participates in the reaction catalyzed by the enzyme. Participation by the metal atom may be direct or may be mediated through another atom or molecule, for example the enzyme or a water molecule or another molecule. The term "matrix metalloprotease" or "matrix metalloproteinase" or "MMP", as used herein, is a metalloprotease of a family of proteases generally capable of degrading extracellular matrix proteins. Certain matrix metalloproteases are also capable of cleaving substrates that are not extracellular matrix proteins.

"Analog," or "analogue" are used in accordance with plain ordinary meaning within Chemistry and Biology and refer to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

A "carboxylate-analogue" is an analogue as described above which includes a carboxylate moiety.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, electrocardiogram, echocardiography, radio-imaging, nuclear scan, and/or stress testing, neuropsychiatric exams, and/or a psychiatric evaluation. For example, certain methods herein treat ROS-associated diseases, including cancer, cardiovascular disease, inflammatory disease, neurodegenerative diseases, or fibrotic disease. Certain methods herein may treat cancer, where the cancer may be associated with ROS overexpression. Certain methods herein may treat cardiovascular disease where the cardiovascular disease is associated with ROS overexpression. Certain methods herein may treat inflammatory disease, where the inflammation is associated with ROS overexpression. Certain method herein may treat fibrotic disease, where the fibrotic disease is associated with ROS overexpression. Certain methods herein may treat neurodegenerative diseases, where the neurodegenerative disease is associated with ROS overexpression or cellular damage associated with ROS overexpression. The term "treating" and conjugations thereof, include prevention of an injury, pathology, condition, or disease.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a patient is human.

"Disease" or "condition" refer to a state of being or health status of a patient or subject capable of being treated with a compound, pharmaceutical composition, or method provided herein. The disease may be inflammatory disease. The disease may be cancer. The disease may be fibrotic disease. The disease may be cardiovascular disease. The disease may be a neurodegenerative disease.

A "ROS-associated disease" refers to a disease caused or characterized by increased expression of ROS or otherwise having increased ROS activity.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" refers to oral administration (i.e. solid or liquid), administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. cardiovascular therapies, diabetes therapies, cancer therapies or another complex described herein).

The compounds and complexes described herein can be used in combination with one another, with other active drugs known to be useful in treating a disease (e.g. anti-cancer drugs or anti-inflammatory drugs) or with adjunctive agents that may not be effective alone, but may contribute to the efficacy of the active agent.

In embodiments, co-administration includes administering one active agent (e.g. a complex described herein) within 0.5, 1, 2, 4, 6, 8, 10, 12, 16, 20, or 24 hours of a second active agent (e.g. anti-cancer drugs or anti-inflammatory drugs). Also contemplated herein, are embodiments, where co-administration includes administering one active agent (e.g. metformin) within 0.5, 1, 2, 4, 6, 8, 10, 12, 16, 20, or 24 hours of a second active agent (e.g. TGR5 ligand). Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another. In embodiments, the compounds and complexes described herein may be combined with treatments for cancer such as chemotherapy or radiation therapy.

The term "associated" or "associated with" in the context of a substance or substance activity or function associated with a disease (e.g. a protein associated disease, a symptom associated with a disease) means that the disease is caused or characterized by (in whole or in part), or a symptom of the disease is caused or characterized by (in whole or in part) the substance or substance activity or function. For example, a symptom of a disease or condition associated with an increased level of ROS. As used herein, what is described as being associated with a disease, if a causative or characterizing agent, could be a target for treatment of the disease. For example, a disease associated ROS overexpression, may be treated with a prodrug described herein which releases a carboxylate drug at the site of ROS overexpression.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, where the two species may be a compound as described herein and a ROS compound. In embodiments contacting includes allowing the ROS compound to react with the prodrug described herein to release a drug which can interact with a protein, enzyme, or cell that is associated with the treated disease.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. In embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

As used herein, the term "neurodegenerative disease" refers to a disease or condition in which the function of a subject's nervous system becomes impaired. Examples of neurodegenerative diseases that may be treated with a prodrug or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), or Mitochondrial Parkinson's disease.

As used herein, the term "cancer" refers to all types of cancer, neoplasm, or malignant or benign tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelog-enous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

As used herein, "cardiovascular disease" refers to diseases associated with the heart, blood vessels or both. Cardiovascular diseases include, but are not limited to, coronary heart disease, cardiomyopathy, hypertensive heart disease, heart failure, cardiac dysrhythmias, inflammatory heart disease, peripheral arterial disease, cerebrovascular disease and inflammatory heart disease.

As used herein "Fibrosis" or "fibrotic disease" refers to any disease or condition characterized by the formation of excess fibrous connective tissue. The formation of excess fibrous connective tissue may be in response to a reparative or reactive process. Fibrosis may be pulmonary fibrosis, liver fibrosis, myelofibrosis, skin fibrosis (e.g. nephrogenic systemic fibrosis and keloid fibrosis), mediastinal fibrosis, cardiac fibrosis, kidney fibrosis, stromal fibrosis, epidural fibrosis, or idiopathic fibrosis.

I. COMPOSITIONS

Provided herein compounds having a prodrug moiety that is removable from a drug moiety after contacting with a ROS to form a carboxylate-drug.

In one aspect, the compounds have the formula:

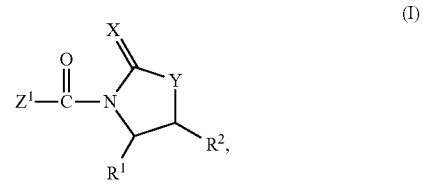

(I)

In formula (I), —C(O)Z' together form a drug moiety. X and Y are independently —S— or —O—. $R^1$ is independently hydrogen, halogen, —CCl$_3$, —CBr$_3$, —CF$_3$, —CI$_3$, —CN, —SR$^6$, —SO$_2$Cl, —SO$_{n1}$R$^6$, —SO$_{v1}$NR$^3$R$^4$, —NHNH$_2$, —ONR$^3$R$^4$, —NHC(O)NHNH$_2$, —NHC(O)NR$^3$R$^4$, —N(O)$_{m1}$, —NR$^3$R$^4$, —C(O)R$^5$, —C(O)—OR$^5$, —C(O)NR$^3$R$^4$, —OR$^6$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^2$ is independently hydrogen, halogen, —CCl$_3$, —CBr$_3$, —CF$_3$, —CI$_3$, —Se, —CN, —SO$_2$Cl, —SO$_{n2}$R$^{10}$, —SO$_{v2}$NR$^7$R$^8$, —NHNH$_2$, —ONR$^7$R$^8$, —NHC(O)NHNH$_2$, —NHC(O)NR$^7$R$^8$, —N(O)$_{m2}$, —NR$^7$R$^8$, —C(O)R$^9$, —C(O)—OR$^9$, —C(O)NR$^7$R$^8$, —OR$^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^3$, $R^4$, $R^5$, $R^6$, $R^7$, $R^8$, $R^9$, and $R^{10}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n1 and n2 are independently an integer from 0 to 4. The symbols m1 and m2 are independently an integer from 1 to 2. The symbols v1 and v2 are independently an integer from 1 to 2.

The compound of formula (I) may have formula:

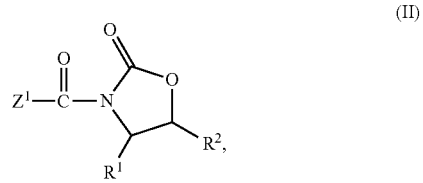

(II)

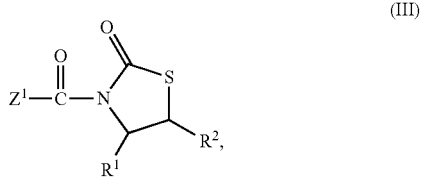

(III)

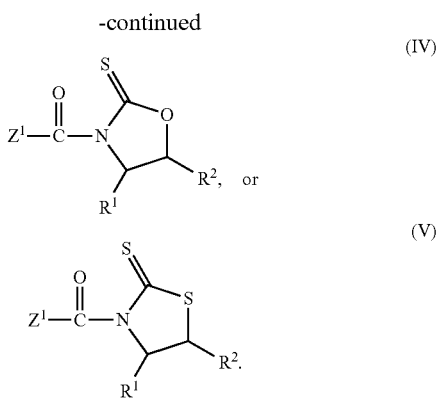

R[1] may independently be hydrogen, halogen, oxo —CCl$_3$, —CBr$_3$, —CF$_3$, —CI$_3$, —CN, —SR$^6$, —SO$_2$Cl, —SO$_{n1}$R$^6$, —SO$_{v1}$NR$^3$R$^4$, —NHNH$_2$, —ONR$^3$R$^4$, —NHC(O)NHNH$_2$, —NHC(O)NR$^3$R$^4$, —N(O)$_{m1}$, —NR$^3$R$^4$, —C(O)R$^5$, —C(O)—OR$^5$, —C(O)NR$^3$R$^4$, —OR$^6$, where R$^3$, R$^4$, R$^5$, R$^6$, n1, m1, and v1 are as described herein. R[1] may independently be hydrogen, halogen, oxo —CCl$_3$, —CBr$_3$, —CF$_3$, —CI$_3$, —CN, —SH, —SO$_2$Cl, —SO$_2$NH$_2$, —NHNH$_2$, —ONH$_2$, —NHC(O)NHNH$_2$, —NHC(O)NH$_2$, —NO$_2$, —NH$_2$, —C(O)OH, —C(O)NH$_2$, —OH. R[1] may independently be hydrogen, halogen, oxo, —CF$_3$, —COOH, or —OH. R[1] may be hydrogen. R[1] may be halogen. R[1] may be oxo. R[1] may be —COOH. R[1] may be —OH. R$^3$, R$^4$, R$^5$, and R$^6$ may independently be hydrogen, halogen, or substituted or unsubstituted alkyl (e.g. C$_1$-C$_5$ substituted or unsubstituted alkyl).

R[1] may independently be substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R[1] may independently be substituted or unsubstituted alkyl. R[1] may independently be unsubstituted alkyl. R[1] may independently be substituted or unsubstituted C$_1$-C$_{20}$ alkyl. R[1] may independently be unsubstituted C$_1$-C$_{20}$ alkyl. R[1] may independently be R$^{11}$-substituted or unsubstituted C$_1$-C$_{20}$ alkyl. R[1] may independently be substituted or unsubstituted C$_1$-C$_{10}$ alkyl. R[1] may independently be unsubstituted C$_1$-C$_{10}$ alkyl. R[1] may independently be R$^{11}$-substituted or unsubstituted C$_1$-C$_{10}$ alkyl. R[1] may independently be substituted or unsubstituted C$_1$-C$_5$ alkyl. R[1] may independently be unsubstituted C$_1$-C$_5$ alkyl. R[1] may independently be R$^{11}$-substituted or unsubstituted alkyl. R[1] may independently be methyl, substituted or unsubstituted ethyl, or substituted or unsubstituted propyl. R[1] may independently be methyl. R[1] may independently be substituted or unsubstituted ethyl. R[1] may independently be substituted or unsubstituted propyl.

R[1] may independently be substituted or unsubstituted heteroalkyl. R[1] may independently be unsubstituted heteroalkyl. R[1] may independently be substituted or unsubstituted 2 to 20 membered heteroalkyl. R[1] may independently be unsubstituted 2 to 20 membered heteroalkyl. R[1] may independently be R$^{11}$-substituted or unsubstituted 2 to 20 membered heteroalkyl. R[1] may independently be substituted or unsubstituted 2 to 10 membered heteroalkyl. R[1] may independently be unsubstituted 2 to 10 membered heteroalkyl. R[1] may independently be R$^{11}$-substituted or unsubstituted 2 to 10 membered heteroalkyl. R[1] may independently be substituted or unsubstituted 2 to 6 membered heteroalkyl. R[1] may independently be unsubstituted 2 to 6 membered heteroalkyl. R[1] may independently be R$^{11}$-substituted or unsubstituted 2 to 6 membered heteroalkyl.

R[1] may independently be substituted or unsubstituted cycloalkyl. R[1] may independently be substituted or unsubstituted 3 to 20 membered cycloalkyl. R[1] may independently be unsubstituted 3 to 20 membered cycloalkyl. R[1] may independently be R$^{11}$-substituted or unsubstituted 3 to 20 membered cycloalkyl. R[1] may independently be substituted or unsubstituted 3 to 10 membered cycloalkyl. R[1] may independently be unsubstituted 3 to 10 membered cycloalkyl. R[1] may independently be R$^{11}$-substituted or unsubstituted 3 to 10 membered cycloalkyl. R[1] may independently be substituted or unsubstituted 3 to 6 membered cycloalkyl. R[1] may independently be unsubstituted 3 to 6 membered cycloalkyl. R[1] may independently be R$^{11}$-substituted or unsubstituted 3 to 6 membered cycloalkyl. R[1] may independently be substituted or unsubstituted 3 membered cycloalkyl. R[1] may independently be unsubstituted 3 membered cycloalkyl. R[1] may independently be R$^{11}$-substituted or unsubstituted 3 membered cycloalkyl. R[1] may independently be substituted or unsubstituted 4 membered cycloalkyl. R[1] may independently be unsubstituted 4 membered cycloalkyl. R[1] may independently be R$^{11}$-substituted or unsubstituted 4 membered cycloalkyl. R[1] may independently be substituted or unsubstituted 5 membered cycloalkyl. R[1] may independently be unsubstituted 5 membered cycloalkyl. R[1] may independently be R$^{11}$-substituted or unsubstituted 5 membered cycloalkyl. R[1] may independently be substituted or unsubstituted 6 membered cycloalkyl. R[1] may independently be unsubstituted 6 membered cycloalkyl. R[1] may independently be R$^{11}$-substituted or unsubstituted 6 membered cycloalkyl.

R[1] may independently be substituted or unsubstituted heterocycloalkyl. R[1] may independently be substituted or unsubstituted 3 to 20 membered heterocycloalkyl. R[1] may independently be unsubstituted 3 to 20 membered heterocycloalkyl. R[1] may independently be R$^{11}$-substituted or unsubstituted 3 to 20 membered heterocycloalkyl. R[1] may independently be substituted or unsubstituted 3 to 10 membered heterocycloalkyl. R[1] may independently be unsubstituted 3 to 10 membered heterocycloalkyl. R[1] may independently be R$^{11}$-substituted or unsubstituted 3 to 10 membered heterocycloalkyl. R[1] may independently be substituted or unsubstituted 3 to 6 membered heterocycloalkyl. R[1] may independently be unsubstituted 3 to 6 membered heterocycloalkyl. R[1] may independently be R$^{11}$-substituted or unsubstituted 3 to 6 membered heterocycloalkyl. R[1] may independently be substituted or unsubstituted 3 membered heterocycloalkyl. R[1] may independently be unsubstituted 3 membered heterocycloalkyl. R[1] may independently be R$^{11}$-substituted or unsubstituted 3 membered heterocycloalkyl. R[1] may independently be substituted or unsubstituted 4 membered heterocycloalkyl. R[1] may independently be unsubstituted 4 membered heterocycloalkyl. R[1] may independently be R$^{11}$-substituted or unsubstituted 4 membered heterocycloalkyl. R[1] may independently be substituted or unsubstituted 5 membered heterocycloalkyl. R[1] may independently be unsubstituted 5 membered heterocycloalkyl. R[1] may independently be R$^{11}$-substituted or unsubstituted 5 membered heterocycloalkyl. R[1] may independently be substituted or unsubstituted 6 membered heterocycloalkyl. R[1] may independently be unsubstituted 6 membered heterocycloalkyl. R[1] may independently be R$^{11}$-substituted or unsubstituted 6 membered heterocycloalkyl.

R[1] may independently be substituted or unsubstituted aryl. R[1] may independently be substituted or unsubstituted 5 to 20 membered aryl. $R^1$ may independently be unsubstituted 5 to 20 membered aryl. $R^1$ may independently be $R^{11}$-substituted or unsubstituted 5 to 20 membered aryl. $R^1$ may independently be substituted or unsubstituted 5 to 10 membered aryl. $R^1$ may independently be unsubstituted 5 to 10 membered aryl. $R^1$ may independently be $R^{11}$-substituted or unsubstituted 5 to 10 membered aryl. $R^1$ may independently be substituted or unsubstituted 5 or 6 membered aryl. $R^1$ may independently be unsubstituted 5 or 6 membered aryl. $R^1$ may independently be $R^{11}$-substituted or unsubstituted 5 or 6 membered aryl. $R^1$ may independently be substituted or unsubstituted 5 membered aryl. $R^1$ may independently be unsubstituted 5 membered aryl. $R^1$ may independently be $R^{11}$-substituted or unsubstituted 5 membered aryl. $R^1$ may independently be substituted or unsubstituted 6 membered aryl. $R^1$ may independently be unsubstituted 6 membered aryl. $R^1$ may independently be $R^{11}$-substituted or unsubstituted 6 membered aryl.

$R^1$ may independently be substituted or unsubstituted heteroaryl. $R^1$ may independently be substituted or unsubstituted 5 to 20 membered heteroaryl. $R^1$ may independently be unsubstituted 5 to 20 membered heteroaryl. $R^1$ may independently be $R^{11}$-substituted or unsubstituted 5 to 20 membered heteroaryl. $R^1$ may independently be substituted or unsubstituted 5 to 10 membered heteroaryl. $R^1$ may independently be unsubstituted 5 to 10 membered heteroaryl. $R^1$ may independently be $R^{11}$-substituted or unsubstituted 5 to 10 membered heteroaryl. $R^1$ may independently be substituted or unsubstituted 5 or 6 membered heteroaryl. $R^1$ may independently be unsubstituted 5 or 6 membered heteroaryl. $R^1$ may independently be $R^{11}$-substituted or unsubstituted 5 or 6 membered heteroaryl. $R^1$ may independently be substituted or unsubstituted 5 membered heteroaryl. $R^1$ may independently be unsubstituted 5 membered heteroaryl. $R^1$ may independently be $R''$-substituted or unsubstituted 5 membered heteroaryl. $R^1$ may independently be substituted or unsubstituted 6 membered heteroaryl. $R^1$ may independently be unsubstituted 6 membered heteroaryl. $R^1$ may independently be $R''$-substituted or unsubstituted 6 membered heteroaryl.

$R^{11}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{12}$-substituted or unsubstituted alkyl (e.g. $C_1$-$C_8$ alkyl), $R^{12}$-substituted or unsubstituted heteroalkyl (e.g. 2 to 8 membered heteroalkyl), $R^{12}$-substituted or unsubstituted cycloalkyl (e.g. $C_3$-$C_8$ cycloalkyl), $R^{12}$-substituted or unsubstituted heterocycloalkyl (e.g. 3 to 6 membered heterocycloalkyl), $R^{12}$-substituted or unsubstituted aryl (e.g. 5 or 6 membered aryl), or $R^{12}$-substituted or unsubstituted heteroaryl (e.g. 5 or 6 membered heteroaryl).

$R^{12}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

$R^{11}$ may be halogen, —$CF_3$, —OH, —$NH_2$, —COOH, —$CONH_2$, —$NO_2$, —SH, $R^{12}$-substituted or unsubstituted alkyl (e.g. $C_1$-$C_8$ alkyl), or $R^{12}$-substituted or unsubstituted alkyl (e.g. $C_1$-$C_8$ alkyl).

$R^2$ may independently be hydrogen, halogen, oxo, —$CCl_3$, —$CBr_3$, —$CF_3$, —$CI_3$, —Se, —CN, —$SO_2Cl$, —$SO_{n2}R^{10}$, —$SO_{v2}NR^7R^8$, —$NHNH_2$, —$ONR^7R^8$, —$NHC(O)NHNH_2$, —$NHC(O)NR^7R^8$, —$N(O)_{m2}$, —$NR^7R^8$, —$C(O)R^9$, —$C(O)NR^7R^8$, —$OR^{10}$, where $R^7$, $R^8$, $R^9$, $R^{10}$, n, m, and v are as described herein. $R^2$ may independently be hydrogen, halogen, oxo —$CCl_3$, —$CBr_3$, —$CF_3$, —$CI_3$, —CN, —SH, —$SO_2Cl$, —$SO_2NH_2$, —$NHNH_2$, —$ONH_2$, —$NHC(O)NHNH_2$, —$NHC(O)NH_2$, —$NO_2$, —$NH_2$, —$C(O)OH$, —$C(O)NH_2$, —OH. $R^2$ may independently be hydrogen, halogen, oxo, —$CF_3$, —COOH, or —OH. $R^2$ may be hydrogen. $R^2$ may be halogen. $R^2$ may be oxo. $R^2$ may be —COOH. $R^2$ may be —OH. $R^7$, $R^8$, $R^9$, and $R^{10}$ may independently be hydrogen, halogen, or substituted or unsubstituted alkyl (e.g. $C_1$-$C_5$ substituted or unsubstituted alkyl).

$R^2$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$R^2$ may independently be substituted or unsubstituted alkyl. $R^2$ may independently be unsubstituted alkyl. $R^2$ may independently be substituted or unsubstituted $C_1$-$C_{20}$ alkyl. $R^2$ may independently be unsubstituted $C_1$-$C_{20}$ alkyl. $R^2$ may independently be $R^{13}$-substituted or unsubstituted $C_1$-$C_{20}$ alkyl. $R^2$ may independently be substituted or unsubstituted $C_1$-$C_{10}$ alkyl. $R^2$ may independently be unsubstituted $C_1$-$C_{10}$ alkyl. $R^2$ may independently be $R^{13}$-substituted or unsubstituted $C_1$-$C_{10}$ alkyl. $R^2$ may independently be substituted or unsubstituted $C_1$-$C_5$ alkyl. $R^2$ may independently be unsubstituted $C_1$-$C_5$ alkyl. $R^2$ may independently be $R^{13}$-substituted or unsubstituted alkyl. $R^2$ may independently be methyl, substituted or unsubstituted ethyl, or substituted or unsubstituted propyl. $R^2$ may independently be methyl. $R^2$ may independently be substituted or unsubstituted ethyl. $R^2$ may independently be substituted or unsubstituted propyl.

$R^2$ may independently be substituted or unsubstituted heteroalkyl. $R^2$ may independently be unsubstituted heteroalkyl. $R^2$ may independently be substituted or unsubstituted 2 to 20 membered heteroalkyl. $R^2$ may independently be unsubstituted 2 to 20 membered heteroalkyl. $R^2$ may independently be $R^{13}$-substituted or unsubstituted 2 to 20 membered heteroalkyl. $R^2$ may independently be substituted or unsubstituted 2 to 10 membered heteroalkyl. $R^2$ may independently be unsubstituted 2 to 10 membered heteroalkyl. $R^2$ may independently be $R^{13}$-substituted or unsubstituted 2 to 10 membered heteroalkyl. $R^2$ may independently be substituted or unsubstituted 2 to 6 membered heteroalkyl. $R^2$ may independently be unsubstituted 2 to 6 membered heteroalkyl. $R^2$ may independently be $R^{13}$-substituted or unsubstituted 2 to 6 membered heteroalkyl.

$R^2$ may independently be substituted or unsubstituted cycloalkyl. $R^2$ may independently be substituted or unsubstituted 3 to 20 membered cycloalkyl. $R^2$ may independently be unsubstituted 3 to 20 membered cycloalkyl. $R^2$ may independently be $R^{13}$-substituted or unsubstituted 3 to 20 membered cycloalkyl. $R^2$ may independently be substituted or unsubstituted 3 to 10 membered cycloalkyl. $R^2$ may independently be unsubstituted 3 to 10 membered cycloalkyl. $R^2$ may independently be $R^{13}$-substituted or unsubstituted 3 to 10 membered cycloalkyl. $R^2$ may independently be substituted or unsubstituted 3 to 6 membered cycloalkyl. $R^2$ may independently be unsubstituted 3 to 6 membered cycloalkyl. $R^2$ may independently be $R^{13}$-substituted or unsubstituted 3 to 6 membered cycloalkyl. $R^2$ may independently be substituted or unsubstituted 3 membered cycloalkyl. $R^2$ may independently be unsubstituted 3 membered cycloalkyl. $R^2$ may independently be $R^{13}$-substituted or unsubstituted 3 membered cycloalkyl. $R^2$ may independently be substituted or unsubstituted 4 membered cycloalkyl. $R^2$ may independently be unsubstituted 4 membered cycloalkyl. $R^2$ may independently be $R^{13}$-substituted or unsubstituted 4 membered cycloalkyl. $R^2$ may independently be substituted or unsubstituted 5 membered cycloalkyl. $R^2$ may independently be unsubstituted 5 membered cycloalkyl. $R^2$ may independently be $R^{13}$-substituted or unsubstituted 5 membered cycloalkyl. $R^2$ may independently be substituted or unsubstituted 6 membered cycloalkyl. $R^2$ may independently be unsubstituted 6 membered cycloalkyl. $R^2$ may independently be $R^{13}$-substituted or unsubstituted 6 membered cycloalkyl.

$R^2$ may independently be substituted or unsubstituted heterocycloalkyl. $R^2$ may independently be substituted or unsubstituted 3 to 20 membered heterocycloalkyl. $R^2$ may independently be unsubstituted 3 to 20 membered heterocycloalkyl. $R^2$ may independently be $R^{13}$-substituted or unsubstituted 3 to 20 membered heterocycloalkyl. $R^2$ may independently be substituted or unsubstituted 3 to 10 membered heterocycloalkyl. $R^2$ may independently be unsubstituted 3 to 10 membered heterocycloalkyl. $R^2$ may independently be $R^{13}$-substituted or unsubstituted 3 to 10 membered heterocycloalkyl. $R^2$ may independently be substituted or unsubstituted 3 to 6 membered heterocycloalkyl. $R^2$ may independently be unsubstituted 3 to 6 membered heterocycloalkyl. $R^2$ may independently be $R^{13}$-substituted or unsubstituted 3 to 6 membered heterocycloalkyl. $R^2$ may independently be substituted or unsubstituted 3 membered heterocycloalkyl. $R^2$ may independently be unsubstituted 3 membered heterocycloalkyl. $R^2$ may independently be $R^{13}$-substituted or unsubstituted 3 membered heterocycloalkyl. $R^2$ may independently be substituted or unsubstituted 4 membered heterocycloalkyl. $R^2$ may independently be unsubstituted 4 membered heterocycloalkyl. $R^2$ may independently be $R^{13}$-substituted or unsubstituted 4 membered heterocycloalkyl. $R^2$ may independently be substituted or unsubstituted 5 membered heterocycloalkyl. $R^2$ may independently be unsubstituted 5 membered heterocycloalkyl. $R^2$ may independently be $R^{13}$-substituted or unsubstituted 5 membered heterocycloalkyl. $R^2$ may independently be substituted or unsubstituted 6 membered heterocycloalkyl. $R^2$ may independently be unsubstituted 6 membered heterocycloalkyl. $R^2$ may independently be $R^{13}$-substituted or unsubstituted 6 membered heterocycloalkyl.

$R^2$ may independently be substituted or unsubstituted aryl. $R^2$ may independently be substituted or unsubstituted 5 to 20 membered aryl. $R^2$ may independently be unsubstituted 5 to 20 membered aryl. $R^2$ may independently be $R^{13}$-substituted or unsubstituted 5 to 20 membered aryl. $R^2$ may independently be substituted or unsubstituted 5 to 10 membered aryl. $R^2$ may independently be unsubstituted 5 to 10 membered aryl. $R^2$ may independently be $R^{13}$-substituted or unsubstituted 5 to 10 membered aryl. $R^2$ may independently be substituted or unsubstituted 5 or 6 membered aryl. $R^2$ may independently be unsubstituted 5 or 6 membered aryl. $R^2$ may independently be $R^{13}$-substituted or unsubstituted 5 or 6 membered aryl. $R^2$ may independently be substituted or unsubstituted 5 membered aryl. $R^2$ may independently be unsubstituted 5 membered aryl. $R^2$ may independently be $R^{13}$-substituted or unsubstituted 5 membered aryl. $R^2$ may independently be substituted or unsubstituted 6 membered aryl. $R^2$ may independently be unsubstituted 6 membered aryl. $R^2$ may independently be $R^{13}$-substituted or unsubstituted 6 membered aryl.

$R^2$ may independently be substituted or unsubstituted heteroaryl. $R^2$ may independently be substituted or unsubstituted 5 to 20 membered heteroaryl. $R^2$ may independently be unsubstituted 5 to 20 membered heteroaryl. $R^2$ may independently be $R^{13}$-substituted or unsubstituted 5 to 20 membered heteroaryl. $R^2$ may independently be substituted or unsubstituted 5 to 10 membered heteroaryl. $R^2$ may independently be unsubstituted 5 to 10 membered heteroaryl. $R^2$ may independently be $R^{13}$-substituted or unsubstituted 5 to 10 membered heteroaryl. $R^2$ may independently be substituted or unsubstituted 5 or 6 membered heteroaryl. $R^2$ may independently be unsubstituted 5 or 6 membered heteroaryl. $R^2$ may independently be $R^{13}$-substituted or unsubstituted 5 or 6 membered heteroaryl. $R^2$ may independently be substituted or unsubstituted 5 membered heteroaryl. $R^2$ may independently be unsubstituted 5 membered heteroaryl. $R^2$ may independently be $R^{13}$-substituted or unsubstituted 5 membered heteroaryl. $R^2$ may independently be substituted or unsubstituted 6 membered heteroaryl. $R^2$ may independently be unsubstituted 6 membered heteroaryl. $R^2$ may independently be $R^{13}$-substituted or unsubstituted 6 membered heteroaryl.

$R^{13}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{14}$-substituted or unsubstituted alkyl (e.g. $C_1$-$C_8$ alkyl), $R^{14}$-substituted or unsubstituted heteroalkyl (e.g. 2 to 8 membered heteroalkyl), $R^{14}$-substituted or unsubstituted cycloalkyl (e.g. $C_3$-$C_8$ cycloalkyl), $R^{14}$-substituted or unsubstituted heterocycloalkyl (e.g. 3 to 6 membered heterocycloalkyl), $R^{14}$-substituted or unsubstituted aryl (e.g. 5 or 6 membered aryl), or $R^{14}$-substituted or unsubstituted heteroaryl (e.g. 5 or 6 membered heteroaryl).

$R^{14}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

$R^{13}$ may be halogen, $-CF_3$, $-OH$, $-NH_2$, $-COOH$, $-CONH_2$, $-NO_2$, $-SH$, $R^{12}$-substituted or unsubstituted alkyl (e.g. $C_1$-$C_8$ alkyl), or $R^{12}$-substituted or unsubstituted alkyl (e.g. $C_1$-$C_8$ alkyl).

$R^1$ and $R^2$ may independently be a carboxylate moiety, a peptidyl moiety (i.e. a monovalent-peptide), or a nucleic acid moiety (i.e. a monovalent-nucleic acid). When $R^1$ and $R^2$ are independently a carboxylate moiety a peptidyl moiety or a nucleic acid moiety, the moieties may target the prodrug to a specific location in a subject as described herein. Such moieties may increase the solubility of the prodrug when compared to a prodrug without such a moiety.

The symbols n1 and n2 may independently be 0, 1, or 2. The symbols n1 and n2 may independently be 3 or 4. The symbols n1 and n2 may independently be 0. The symbols n1 and n2 may independently be 1. The symbols n1 and n2 may independently be 2. The symbols n1 and n2 may independently be 3. The symbols n1 and n2 may independently be 4. The symbols m1 and m2 may independently be 1. The symbols m1 and m2 may independently be 2. The symbols v1 and v2 may independently be 1. The symbols v1 and v2 may independently be 2.

—C(O)Z$^1$ is a drug moiety and may be derived from non-steroidal anti-inflammatory drug moiety, a histone deacetylase (HDAC) inhibitor drug moiety, a statin drug moiety, leukotriene receptor antagonist drug moiety, a fluoroquinolone drug moiety, a matrix metalloproteinase (MMP) inhibitor drug moiety, a cardiovascular therapy drug moiety (e.g. an angiotensin-converting enzyme (ACE drug moiety) inhibitor drug moiety, or an angiotensin II receptor blocker drug moiety (ARB drug moiety)), a furosemide drug moiety or analogue drug moiety thereof which retains furosemide activity, or retinoic acid drug moiety including analogues thereof which retain retinoic acid activity.

The drug moiety may be derived from a non-steroidal anti-inflammatory drug moiety (NSAID moiety). The NSAID moiety may be a COX inhibitor drug moiety. The COX inhibitor drug moiety may be a salicylate drug moiety or a salicylate-analogue drug moiety. The COX inhibitor drug moiety may be acetylsalicylic acid drug moiety, diflunisal drug moiety, salsalate drug moiety, or choline magnesium trisalicylate drug moiety, including analogues thereof which have COX inhibitor drug activity upon removal of the prodrug moiety. The COX inhibitor drug moiety may be a propionic acid COX inhibitor drug moiety. The COX inhibitor drug moiety may be an ibuprofen drug moiety, a dexibuprofen drug moiety, a naproxen drug moiety, a fenoprofen drug moiety, a ketoprofen drug moiety, a dexketoprofen drug moiety, a flurbiprofen drug moiety, an oxaprozin drug moiety, or a loxoprofen drug moiety, including analogues thereof having COX inhibitor drug activity upon removal of the prodrug moiety. The COX inhibitor drug moiety may be an ibuprofen drug moiety, or an analogue thereof which has ibuprofen activity upon removal of the prodrug moiety. The COX inhibitor drug moiety may be a dexibuprofen drug moiety, or an analogue thereof which has dexibuprofen activity upon removal of the prodrug moiety. The COX inhibitor drug moiety may be a naproxen drug moiety, or an analogue thereof which has naproxen activity upon removal of the prodrug moiety. The COX inhibitor drug moiety may be a fenoprofen drug moiety, or an analogue thereof which has fenoprofen activity upon removal of the prodrug moiety. The COX inhibitor drug moiety may be a ketoprofen drug moiety, or an analogue thereof which has ketoprofen activity upon removal of the prodrug moiety. The COX inhibitor drug moiety may be a dexketoprofen drug moiety, or an analogue thereof which has dexketoprofen activity upon removal of the prodrug moiety. The COX inhibitor drug moiety may be a flurbiprofen drug moiety, or an analogue thereof which has flurbiprofen activity upon removal of the prodrug moiety. The COX inhibitor drug moiety may be an oxaprozin, or an analogue thereof which has oxaprozin activity upon removal of the prodrug moiety. The COX inhibitor drug moiety may be a loxoprofen drug moiety, or an analogue thereof which has loxoprofen activity upon removal of the prodrug moiety.

The COX inhibitor drug moiety may be an acetic acid COX inhibitor drug moiety. The COX inhibitor drug moiety may be an indomethacin drug moiety, a tolmetin drug moiety, a sulindac drug moiety, an etodolac drug moiety, a ketorolac drug moiety, a diclofenac drug moiety, or an aceclofenac drug moiety, including analogues thereof having activity upon removal of the prodrug moiety. The COX inhibitor drug moiety may be an indomethacin drug moiety, or an analogue thereof which has indomethacin activity upon removal of the prodrug moiety. The COX inhibitor drug moiety may be a tolmetin drug moiety, or an analogue thereof which has tolmetin activity upon removal of the prodrug moiety. The COX inhibitor drug moiety may be a sulindac drug moiety, or an analogue thereof which has sulindac activity upon removal of the prodrug moiety. The COX inhibitor drug moiety may be an etodolac drug, or an analogue thereof which has etodolac activity upon removal of the prodrug moiety. The COX inhibitor drug moiety may be a ketorolac drug moiety, or an analogue thereof which has ketorolac activity upon removal of the prodrug moiety. The COX inhibitor drug moiety may be a diclofenac drug, or an analogue thereof which has diclofenac activity upon removal of the prodrug moiety. The COX inhibitor drug moiety may be an aceclofenac drug moiety, or an analogue thereof which has aceclofenac activity upon removal of the prodrug moiety.

The COX inhibitor drug moiety may be an anthranilic acid COX inhibitor drug moiety. The COX inhibitor drug moiety may be a mefenamic acid drug moiety, a meclofenamic acid drug moiety, a flufenamic acid drug moiety, or a tolfenamic acid drug moiety, including analogues thereof having activity upon removal of the prodrug moiety. The COX inhibitor drug moiety may be a mefenamic acid drug moiety, or an analogue thereof which has mefenamic acid activity upon removal of the prodrug moiety. The COX inhibitor drug moiety may be a meclofenamic acid drug moiety, or an analogue thereof which has meclofenamic acid activity upon removal of the prodrug moiety. The COX inhibitor drug moiety may be a flufenamic acid drug moiety, or an analogue thereof which has flufenamic acid activity upon removal of the prodrug moiety. The COX inhibitor drug moiety may be a tolfenamic acid drug moiety, or an analogue thereof which has tolfenamic acid activity upon removal of the prodrug moiety.

The COX inhibitor drug moiety may be an ibuprofen drug moiety, a dexibuprofen drug moiety, a naproxen drug moiety, a fenoprofen drug moiety, a ketoprofen drug moiety, a dexketoprofen drug moiety, a flurbiprofen drug moiety, an oxaprozin drug moiety, or a loxoprofen drug moiety. The COX inhibitor drug moiety may be an indomethacin drug moiety, a tolmetin drug moiety, a sulindac drug moiety, an etodolac drug moiety, a ketorolac drug moiety, a diclofenac drug moiety, an aceclofenac drug moiety, a mefenamic acid drug moiety, a meclofenamic acid drug moiety, a flufenamic acid drug moiety, a tolfenamic acid drug moiety, an acetylsalicylic acid drug moiety, a diflunisal drug moiety, a salsalate drug moiety, a choline magnesium trisalicylate drug moiety, or a licofelone drug moiety. The COX inhibitor drug moiety may be an iso-butyl-propanoic-phenolic acid drug moiety.

The drug moiety may be derived from a HDAC inhibitor drug moiety. The HDAC inhibitor may be a Class I HDAC inhibitor drug moiety, a Class II HDAC inhibitor drug moiety, a Class III HDAC inhibitor drug moiety or a Class IV HDAC inhibitor drug moiety. The HDAC inhibitor may be a phenylbutyric acid drug moiety or a valproic acid drug moiety. The HDAC inhibitor may be a phenylbutyric acid drug moiety. The HDAC inhibitor may be a valproic acid drug moiety.

The drug moiety may be derived from a statin drug moiety. The statin drug moiety may be an atorvastatin drug moiety, a cerivastatin drug moiety, a fluvastatin drug moiety, a pitavastatin drug moiety, or a rosuvastatin drug moiety. The statin drug moiety may be an atorvastatin drug moiety. The statin drug moiety may be a cerivastatin drug moiety. The statin drug moiety may be a fluvastatin drug moiety. The statin drug moiety may be a pitavastatin drug moiety. The statin drug moiety may be a rosuvastatin drug moiety.

The drug moiety may be derived from a leukotriene receptor antagonist drug moiety. The leukotriene receptor antagonist drug moiety may be a montelukast drug moiety or an analogue which has montelukast activity upon removal of the prodrug moiety.

The drug moiety may be derived from a fluoroquinolone drug moiety. The fluoroquinolone drug moiety may be a ciprofloxin drug moiety, a balofloxacin drug moiety, a grepafloxacin drug moiety, a levofloxacin drug moiety, a pazufloxacin drug moiety, a sparfloxacin drug moiety, a temafloxacin drug moiety, a tosufloxacin drug moiety, a clinafloxacin drug moiety, a gatifloxacin drug moiety, a gemifloxacin drug moiety, a moxifloxacin drug moiety, a sitafloxacin drug moiety, a trovafloxacin drug moiety, a prulifloxacin drug moiety, a delafloxacin drug moiety, a JNJ-Q2 drug moiety, or a nemonoxacin drug moiety, or an analogue thereof which has antibacterial activity upon removal of the prodrug moiety. The fluoroquinolone drug moiety may be a ciprofloxin drug moiety, or an analogue thereof which has antibacterial activity upon removal of the prodrug moiety. The fluoroquinolone drug moiety may be a balofloxacin drug moiety, or an analogue thereof which has antibacterial activity upon removal of the prodrug moiety. The fluoroquinolone drug moiety may be a grepafloxacin drug moiety, or an analogue thereof which has antibacterial activity upon removal of the prodrug moiety. The fluoroquinolone drug moiety may be a levofloxacin drug moiety, or an analogue thereof which has antibacterial activity upon removal of the prodrug moiety. The fluoroquinolone drug moiety may be a pazufloxacin drug moiety, or an analogue thereof which has antibacterial activity upon removal of the prodrug moiety. The fluoroquinolone drug moiety may be a sparfloxacin drug moiety, or an analogue thereof which has antibacterial activity upon removal of the prodrug moiety. The fluoroquinolone drug moiety may be a temafloxacin drug moiety, or an analogue thereof which has antibacterial activity upon removal of the prodrug moiety. The fluoroquinolone drug moiety may be a clinafloxacin drug moiety, or an analogue thereof which has antibacterial activity upon removal of the prodrug moiety. The fluoroquinolone drug moiety may be a gatifloxacin drug moiety, or an analogue thereof which has antibacterial activity upon removal of the prodrug moiety. The fluoroquinolone drug moiety may be a gemifloxacin drug moiety, or an analogue thereof which has antibacterial activity upon removal of the prodrug moiety. The fluoroquinolone drug moiety may be a moxifloxacin drug moiety, or an analogue thereof which has antibacterial activity upon removal of the prodrug moiety. The fluoroquinolone drug moiety may be a sitafloxacin drug moiety, or an analogue thereof which has antibacterial activity upon removal of the prodrug moiety. The fluoroquinolone drug moiety may be a trovafloxacin drug moiety, or an analogue thereof which has antibacterial activity upon removal of the prodrug moiety. The fluoroquinolone drug moiety may be a prulifloxacin drug moiety, or an analogue thereof which has antibacterial activity upon removal of the prodrug moiety. The fluoroquinolone drug moiety may be a delafloxacin drug moiety, or an analogue thereof which has antibacterial activity upon removal of the prodrug moiety. The fluoroquinolone drug moiety may be a JNJ-Q2 drug moiety, or an analogue thereof which has antibacterial activity upon removal of the prodrug moiety. The fluoroquinolone drug moiety may be a nemonoxacin drug moiety, or an analogue thereof which has antibacterial activity upon removal of the prodrug moiety.

The drug moiety may be derived from a matrix metalloproteinase inhibitor drug moiety. The MMP inhibitor drug moiety may inhibit MMP1, MMP2, MMP3, or MMP9 upon removal of the prodrug moiety (i.e. formation of a MMP inhibitor drug). The MMP inhibitor drug moiety may be a sulfonamide-based MMP inhibitor drug moiety (e.g. arylsulfonamides, cyclic sulfonamides). The MMP inhibitor drug moiety may be BAY 12-9566.

The drug moiety may be derived from a cardiovascular therapy drug moiety. The drug moiety may be an amlodipine drug moiety. The cardiovascular therapy drug moiety may be an ACE inhibitor drug moiety. The ACE inhibitor drug moiety may be an enalapril drug moiety, a ramipril drug moiety, a quinapril drug moiety, a perindopril drug moiety, a lisinopril drug moiety, a benazepril drug moiety, an imidapril drug moiety, a trandolapril drug moiety, or a cilazapril drug moiety. The ACE inhibitor drug moiety may be an enalapril drug moiety. The ACE inhibitor drug moiety may be a ramipril drug moiety. The ACE inhibitor drug moiety may be a quinapril drug moiety. The ACE inhibitor drug moiety may be a perindopril drug moiety. The ACE inhibitor drug moiety may be a lisinopril drug moiety. The ACE inhibitor drug moiety may be a benazepril drug moiety. The ACE inhibitor drug moiety may be an imidapril drug moiety. The ACE inhibitor drug moiety may be a trandolapril drug moiety. The ACE inhibitor drug moiety may be a cilazapril drug moiety.

The cardiovascular therapy agent drug moiety may be an ARB drug moiety. The ARB drug moiety may be a valsartan drug moiety, a telmisartan drug moiety, an azilsartan drug moiety, or an olmesartan drug moiety. The ARB drug moiety may be a valsartan drug moiety. The ARB drug moiety may be a telmisartan drug moiety. The ARB drug moiety may be an azilsartan drug moiety. The ARB drug moiety may be an olmesartan drug moiety.

The anti-cancer drug moiety may be an anti-cancer alkylating drug moiety. The anti-cancer alkylating drug moiety may be a bendamustine drug moiety, a melphalan drug moiety, or a chlorambucil drug moiety. The anti-cancer alkylating drug moiety may be a bendamustine drug moiety. The anti-cancer alkylating drug moiety may be a melphalan drug moiety. The anti-cancer alkylating drug moiety may a chlorambucil drug moiety.

The drug moiety may be derived from a furosemide drug moiety or an analogue thereof which has furosemide activity upon removal of the prodrug moiety.

The drug moiety may be derived from a retinoic acid drug moiety or an analogue thereof which has retinoic acid activity upon removal of the prodrug moiety.

The drug moiety may be derived from an anti-folate drug moiety. The anti-folate drug moiety may be a methotrexate drug moiety or a pemetrexed drug moiety. The anti-folate drug moiety may be a methotrexate drug moiety. The anti-folate drug moiety may be a pemetrexed drug moiety.

The drug moiety may have the formula:

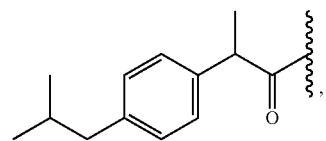

(1)

-continued

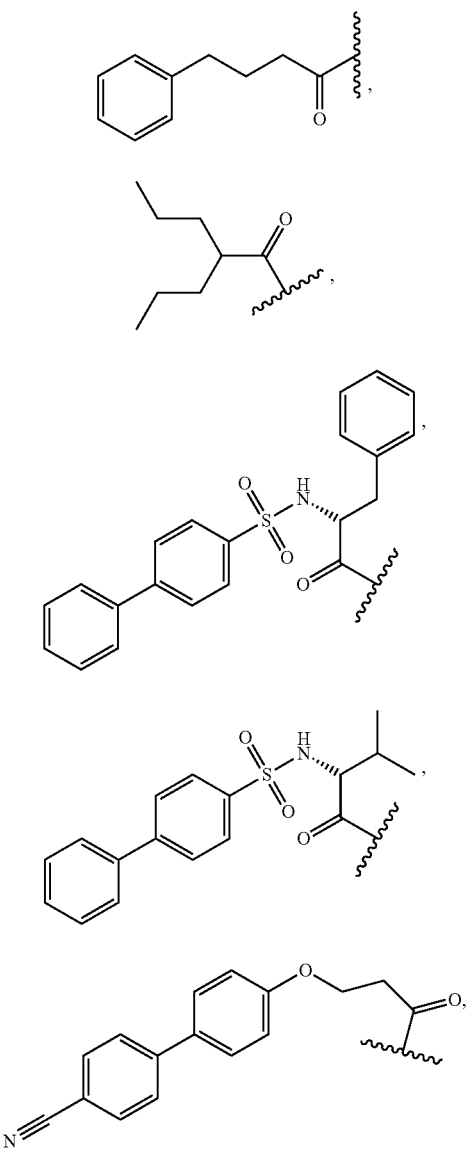

(2)
(3)
(4)
(5)
(6)
(7)
(8)

-continued

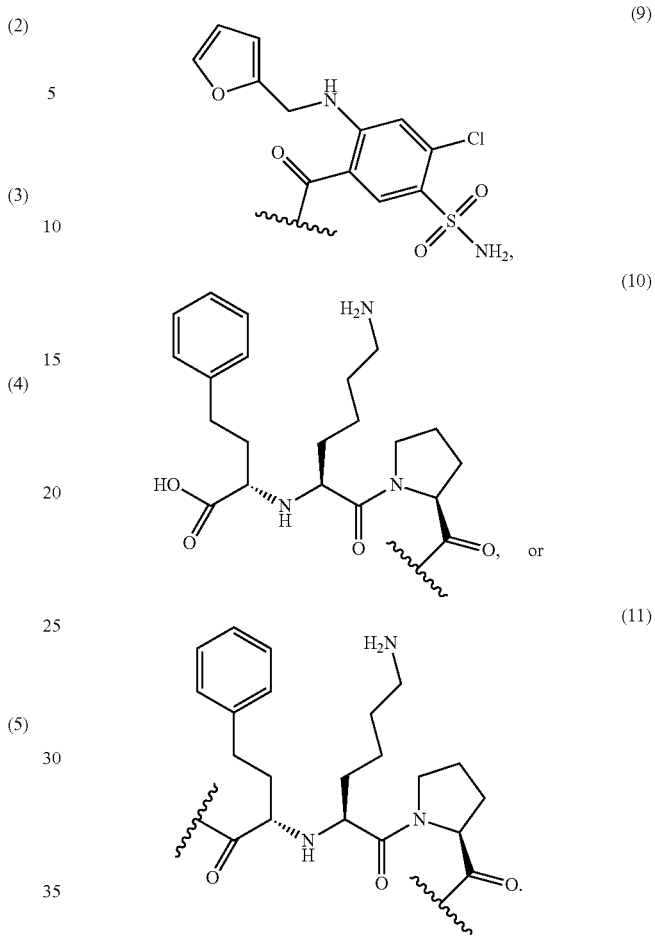

(9)
(10)
or
(11)

The compounds (i.e. prodrugs) described herein may be a product of a carboxylic acid drug and a prodrug moiety as described herein (e.g. substituted or unsubstituted oxazolidinone, substituted or unsubstituted oxazolidithione, substituted or unsubstituted thiazolidinone, or substituted or unsubstituted thiazolidithione).

In another aspect is a prodrug having formula:

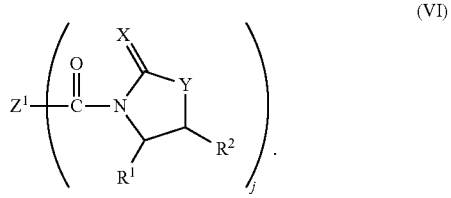

(VI)

In the compound of formula (VI), $Z^1$—C(O)— together form a drug moiety. $Z^1$ (i.e. a drug moiety), X, Y, $R^1$, and $R^2$ are as described herein. The symbol j is an integer between 2 and 4. The symbol j may be 2 (i.e. the carboxyl-linked drug moiety has two carboxylate moieties bound by the prodrug moiety). The symbol j may be 3 ((i.e. the carboxyl-linked drug moiety has three carboxylate moieties bound by the prodrug moiety). The symbol j may be 4 (i.e. the carboxyl-linked drug moiety has two carboxylate moieties bound by the prodrug moiety).

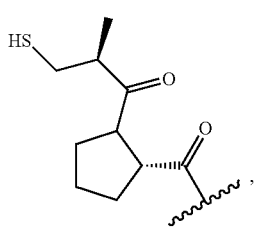

Also provided herein are compounds having the formula:

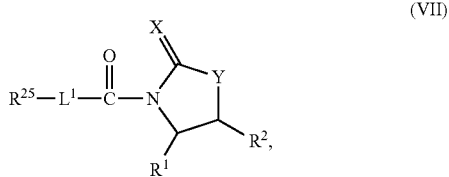

(VII)

In formula (VII), —C(O)-L$^1$-R$^{25}$ together form a drug moiety. X, Y, R', and R$^2$ are as described herein. The drug moiety may be a drug moiety described herein. L$^1$ is a bond, —SO$_2$—, —S(O)$_2$NH—, —NHSO$_2$—, —C(O)O—, —OC(O)—, —C(O)—, —C(O)NH—, —NH—, —NHC(O)—, —O—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^{25}$ is hydrogen, halogen, oxo, —CCl$_3$, —CBr$_3$, —CF$_3$, —CI$_3$, —CN, —SH, —SO$_2$Cl, —SO$_2$NH, —SO$_2$Cl, —NHNH$_2$, —ONH$_2$, —NHC(O)NHNH$_2$, —NHC(O)NNH$_2$, —NO$_2$, —NH$_2$, —C(O)H, —C(O)OH, —C(O)NNH$_2$, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

L$^1$ may be a bond, —SO$_2$—, —S(O)$_2$NH—, —NHSO$_2$—, —C(O)O—, —OC(O)—, —C(O)—, —C(O)NH—, —NH—, —NHC(O)—, —O—, or —S—. L$^1$ may be a bond, —SO$_2$—, —C(O)O—, —C(O)—, —C(O)NH—, —NH—, —O—, or —S—. L$^1$ may be a bond. L$^1$ may be —O—. L$^1$ may be —NH—. L$^1$ may be substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

L$^1$ may be substituted or unsubstituted alkylene. L$^1$ may be substituted alkylene. L$^1$ may be unsubstituted alkylene. L$^1$ may be R$^{20}$-substituted or unsubstituted alkylene. L$^1$ may be substituted or unsubstituted C$_1$-C$_{20}$ alkylene. L$^1$ may be substituted C$_1$-C$_{20}$ alkylene. L$^1$ may be unsubstituted C$_1$-C$_{20}$ alkylene. L$^1$ may be R$^{20}$-substituted or C$_1$-C$_{20}$ unsubstituted alkylene. L$^1$ may be substituted or unsubstituted C$_1$-C$_{10}$ alkylene. L$^1$ may be substituted C$_1$-C$_{10}$ alkylene. L$^1$ may be unsubstituted C$_1$-C$_{10}$ alkylene. L$^1$ may be R$^{20}$-substituted or unsubstituted C$_1$-C$_{10}$ alkylene. L$^1$ may be substituted or unsubstituted C$_1$-C$_5$ alkylene. L$^1$ may be substituted C$_1$-C$_5$ alkylene. L$^1$ may be unsubstituted C$_1$-C$_5$ alkylene. L$^1$ may be R$^{20}$-substituted or unsubstituted C$_1$-C$_5$ alkylene.

L$^1$ may be substituted or unsubstituted heteroalkylene. L$^1$ may be substituted heteroalkylene. L$^1$ may be unsubstituted heteroalkylene. L$^1$ may be R$^{20}$-substituted or unsubstituted heteroalkylene. L$^1$ may be substituted or unsubstituted 2 to 20 membered heteroalkylene. L$^1$ may be substituted 2 to 20 membered heteroalkylene. L$^1$ may be unsubstituted 2 to 20 membered heteroalkylene. L$^1$ may be R$^{20}$-substituted or unsubstituted 2 to 20 membered heteroalkylene. L$^1$ may be substituted or unsubstituted 2 to 10 membered heteroalkylene. L$^1$ may be substituted 2 to 10 membered heteroalkylene. L$^1$ may be unsubstituted 2 to 10 membered heteroalkylene. L$^1$ may be R$^{20}$-substituted or unsubstituted 2 to 10 membered heteroalkylene. L$^1$ may be substituted or unsubstituted 2 to 6 membered heteroalkylene. L$^1$ may be substituted 2 to 6 membered heteroalkylene. L$^1$ may be unsubstituted 2 to 6 membered heteroalkylene. L$^1$ may be R$^{20}$-substituted or unsubstituted 2 to 6 membered heteroalkylene.

L$^1$ may be substituted or unsubstituted cycloalkylene. L$^1$ may be substituted cycloalkylene. L$^1$ may be unsubstituted cycloalkylene. L$^1$ may be R$^{20}$-substituted or unsubstituted cycloalkylene. L$^1$ may be substituted or unsubstituted 3 to 20 membered cycloalkylene. L$^1$ may be substituted 3 to 20 membered cycloalkylene. L$^1$ may be unsubstituted 3 to 20 membered cycloalkylene. L$^1$ may be R$^{20}$-substituted or unsubstituted 3 to 20 membered cycloalkylene. L$^1$ may be substituted or unsubstituted 3 to 10 membered cycloalkylene. L$^1$ may be substituted 3 to 10 membered cycloalkylene. L$^1$ may be unsubstituted 3 to 10 membered cycloalkylene. L$^1$ may be R$^{20}$-substituted or unsubstituted 3 to 10 membered cycloalkylene. L$^1$ may be substituted or unsubstituted 3 to 6 membered cycloalkylene. L$^1$ may be substituted 3 to 6 membered cycloalkylene. L$^1$ may be unsubstituted 3 to 6 membered cycloalkylene. L$^1$ may be R$^{20}$-substituted or unsubstituted 3 to 6 membered cycloalkylene.

L$^1$ may be substituted or unsubstituted heterocycloalkylene. L$^1$ may be substituted heterocycloalkylene. L$^1$ may be unsubstituted heterocycloalkylene. L$^1$ may be R$^{20}$-substituted or unsubstituted heterocycloalkylene. L$^1$ may be substituted or unsubstituted 3 to 20 membered heterocycloalkylene. L$^1$ may be substituted 3 to 20 membered heterocycloalkylene. L$^1$ may be unsubstituted 3 to 20 membered heterocycloalkylene. L$^1$ may be R$^{20}$-substituted or unsubstituted 3 to 20 membered heterocycloalkylene. L$^1$ may be substituted or unsubstituted 3 to 10 membered heterocycloalkylene. L$^1$ may be substituted 3 to 10 membered heterocycloalkylene. L$^1$ may be unsubstituted 3 to 10 membered heterocycloalkylene. L$^1$ may be R$^{20}$-substituted or unsubstituted 3 to 10 membered heterocycloalkylene. L$^1$ may be substituted or unsubstituted 3 to 6 membered heterocycloalkylene. L$^1$ may be substituted 3 to 6 membered heterocycloalkylene. L$^1$ may be unsubstituted 3 to 6 membered heterocycloalkylene. L$^1$ may be R$^{20}$-substituted or unsubstituted 3 to 6 membered heterocycloalkylene. L$^1$ may be substituted or unsubstituted arylene. L$^1$ may be substituted arylene. L$^1$ may be unsubstituted arylene. L$^1$ may be R$^{20}$-substituted or unsubstituted arylene. L$^1$ may be substituted or unsubstituted 5 to 20 membered arylene. L$^1$ may be substituted 5 to 20 membered arylene. L$^1$ may be unsubstituted 5 to 20 membered arylene. L$^1$ may be R$^{20}$-substituted or unsubstituted 5 to 20 membered arylene. L$^1$ may be substituted or unsubstituted 5 to 10 membered arylene. L$^1$ may be substituted 5 to 10 membered arylene. L$^1$ may be unsubstituted 5 to 10 membered arylene. L$^1$ may be R$^{20}$-substituted or unsubstituted 5 to 10 membered arylene. L$^1$ may be substituted or unsubstituted 5 or 6 membered arylene. L$^1$ may be substituted 5 to 6 membered arylene. L$^1$ may be unsubstituted 5 to 6 membered arylene. L$^1$ may be R$^{20}$-substituted or unsubstituted 5 to 6 membered arylene.

L$^1$ may be substituted or unsubstituted heteroarylene. L$^1$ may be substituted heteroarylene. L$^1$ may be unsubstituted heteroarylene. L$^1$ may be R$^{20}$-substituted or unsubstituted heteroarylene. L$^1$ may be substituted or unsubstituted 5 to 20 membered heteroarylene. L$^1$ may be substituted 5 to 20 membered heteroarylene. L$^1$ may be unsubstituted 5 to 20 membered heteroarylene. L$^1$ may be R$^{20}$-substituted or unsubstituted 5 to 20 membered heteroarylene. L$^1$ may be substituted or unsubstituted 5 to 10 membered heteroarylene. L$^1$ may be substituted 5 to 10 membered heteroarylene. L$^1$ may be unsubstituted 5 to 10 membered heteroarylene. $L^1$ may be $R^{20}$-substituted or unsubstituted 5 to 10 membered heteroarylene. $L^1$ may be substituted or unsubstituted 5 or 6 membered heteroarylene. $L^1$ may be substituted 5 to 6 membered heteroarylene. $L^1$ may be unsubstituted 5 to 6 membered heteroarylene. $L^1$ may be $R^{20}$-substituted or unsubstituted 5 to 6 membered heteroarylene.

$R^{20}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{21}$-substituted or unsubstituted alkyl (e.g. $C_1$-$C_8$ alkyl), $R^{21}$-substituted or unsubstituted heteroalkyl (e.g. 2 to 8 membered heteroalkyl), $R^{21}$-substituted or unsubstituted cycloalkyl (e.g. $C_3$-$C_8$ cycloalkyl), $R^{21}$-substituted or unsubstituted heterocycloalkyl (e.g. 3 to 6 membered heterocycloalkyl), $R^{21}$-substituted or unsubstituted aryl (e.g. 5 or 6 membered aryl), or $R^{21}$-substituted or unsubstituted heteroaryl (e.g. 5 or 6 membered heteroaryl).

$R^{21}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{22}$-substituted or unsubstituted alkyl (e.g. $C_1$-$C_8$ alkyl), $R^{22}$-substituted or unsubstituted heteroalkyl (e.g. 2 to 8 membered heteroalkyl), $R^{22}$-substituted or unsubstituted cycloalkyl (e.g. $C_3$-$C_8$ cycloalkyl), $R^{22}$-substituted or unsubstituted heterocycloalkyl (e.g. 3 to 6 membered heterocycloalkyl), $R^{22}$-substituted or unsubstituted aryl (e.g. 5 or 6 membered aryl), or $R^{22}$-substituted or unsubstituted heteroaryl (e.g. 5 or 6 membered heteroaryl).

$R^{22}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{23}$-substituted or unsubstituted alkyl (e.g. $C_1$-$C_8$ alkyl), $R^{23}$-substituted or unsubstituted heteroalkyl (e.g. 2 to 8 membered heteroalkyl), $R^{23}$-substituted or unsubstituted cycloalkyl (e.g. $C_3$-$C_8$ cycloalkyl), $R^{23}$-substituted or unsubstituted heterocycloalkyl (e.g. 3 to 6 membered heterocycloalkyl), $R^{23}$-substituted or unsubstituted aryl (e.g. 5 or 6 membered aryl), or $R^{23}$-substituted or unsubstituted heteroaryl (e.g. 5 or 6 membered heteroaryl).

$R^{23}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{24}$-substituted or unsubstituted alkyl (e.g. $C_1$-$C_8$ alkyl), $R^{24}$-substituted or unsubstituted heteroalkyl (e.g. 2 to 8 membered heteroalkyl), $R^{24}$-substituted or unsubstituted cycloalkyl (e.g. $C_3$-$C_8$ cycloalkyl), $R^{24}$-substituted or unsubstituted heterocycloalkyl (e.g. 3 to 6 membered heterocycloalkyl), $R^{24}$-substituted or unsubstituted aryl (e.g. 5 or 6 membered aryl), or $R^{24}$-substituted or unsubstituted heteroaryl (e.g. 5 or 6 membered heteroaryl).

$R^{24}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

$R^{25}$ may be hydrogen, halogen, oxo, $-CCl_3$, $-CBr_3$, $-CF_3$, $-CI_3$, $-CN$, $-SO_2Cl$, $-SO_2NH$, $-SH$, $-SO_2Cl$, $-NHNH_2$, $-ONH_2$, $-NHC(O)NHNH_2$, $-NHC(O)NNH_2$, $-NO_2$, $-NH_2$, $-C(O)H$, $-C(O)OH$, $-C(O)NNH_2$, or $-OH$. $R^{25}$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{25}$ may be substituted or unsubstituted alkyl. $R^{25}$ may be substituted alkyl. $R^{25}$ may be unsubstituted alkyl. $R^{25}$ may be $R^{26}$-substituted or unsubstituted alkyl. $R^{25}$ may be $R^{26}$-substituted alkyl. $R^{25}$ may be substituted or unsubstituted $C_1$-$C_{20}$ alkyl. $R^{25}$ may be substituted $C_1$-$C_{20}$ alkyl. $R^{25}$ may be unsubstituted $C_1$-$C_{20}$ alkyl. $R^{25}$ may be $R^{26}$-substituted or unsubstituted $C_1$-$C_{20}$ alkyl. $R^{25}$ may be $R^{26}$-substituted $C_1$-$C_{20}$ alkyl. $R^{25}$ may be substituted or unsubstituted $C_1$-$C_{10}$ alkyl. $R^{25}$ may be substituted $C_1$-$C_{10}$ alkyl. $R^{25}$ may be unsubstituted $C_1$-$C_{10}$ alkyl. $R^{25}$ may be $R^{26}$-substituted or unsubstituted $C_1$-$C_{10}$ alkyl. $R^{25}$ may be $R^{26}$-substituted $C_1$-$C_{10}$ alkyl. $R^{25}$ may be substituted or unsubstituted $C_1$-$C_5$ alkyl. $R^{25}$ may be substituted $C_1$-$C_5$ alkyl. $R^{25}$ may be unsubstituted $C_1$-$C_5$ alkyl. $R^{25}$ may be $R^{26}$-substituted or unsubstituted $C_1$-$C_5$ alkyl. $R^{25}$ may be $R^{26}$-substituted $C_1$-$C_5$ alkyl.

$R^{25}$ may be substituted or unsubstituted heteroalkyl. $R^{25}$ may be substituted heteroalkyl. $R^{25}$ may be unsubstituted heteroalkyl. $R^{25}$ may be $R^{26}$-substituted or unsubstituted heteroalkyl. $R^{25}$ may be $R^{26}$-substituted heteroalkyl. $R^{25}$ may be substituted or unsubstituted 2 to 20 membered heteroalkyl. $R^{25}$ may be substituted 2 to 20 membered heteroalkyl. $R^{25}$ may be unsubstituted 2 to 20 membered heteroalkyl. $R^{25}$ may be $R^{26}$-substituted or unsubstituted 2 to 20 membered heteroalkyl. $R^{25}$ may be $R^{26}$-substituted 2 to 20 membered heteroalkyl. $R^{25}$ may be substituted or unsubstituted 2 to 10 membered heteroalkyl. $R^{25}$ may be substituted 2 to 10 membered heteroalkyl. $R^{25}$ may be unsubstituted 2 to 10 membered heteroalkyl. $R^{25}$ may be $R^{26}$-substituted or unsubstituted 2 to 10 membered heteroalkyl. $R^{25}$ may be $R^{26}$-substituted 2 to 10 membered heteroalkyl. $R^{25}$ may be substituted or unsubstituted 2 to 6 membered heteroalkyl. $R^{25}$ may be substituted 2 to 6 membered heteroalkyl. $R^{25}$ may be unsubstituted 2 to 6 membered heteroalkyl. $R^{25}$ may be $R^{26}$-substituted or unsubstituted 2 to 6 membered heteroalkyl. $R^{25}$ may be $R^{26}$-substituted 2 to 6 membered heteroalkyl.

$R^{25}$ may be substituted or unsubstituted cycloalkyl. $R^{25}$ may be substituted cycloalkyl. $R^{25}$ may be unsubstituted cycloalkyl. $R^{25}$ may be $R^{26}$-substituted or unsubstituted cycloalkyl. $R^{25}$ may be $R^{26}$-substituted cycloalkyl. $R^{25}$ may be substituted or unsubstituted 3 to 20 membered cycloalkyl. $R^{25}$ may be substituted 3 to 20 membered cycloalkyl. $R^{25}$ may be unsubstituted 3 to 20 membered cycloalkyl. $R^{25}$ may be $R^{26}$-substituted or unsubstituted 3 to 20 membered cycloalkyl. $R^{25}$ may be $R^{26}$-substituted 3 to 20 membered cycloalkyl. $R^{25}$ may be substituted or unsubstituted 3 to 10 membered cycloalkyl. $R^{25}$ may be substituted 3 to 10 membered cycloalkyl. $R^{25}$ may be unsubstituted 3 to 10 membered cycloalkyl. $R^{25}$ may be $R^{26}$-substituted or unsubstituted 3 to 10 membered cycloalkyl. $R^{25}$ may be $R^{26}$-substituted 3 to 10 membered cycloalkyl. $R^{25}$ may be substituted or unsubstituted 3 to 6 membered cycloalkyl. $R^{25}$ may be substituted 3 to 6 membered cycloalkyl. $R^{25}$ may be unsubstituted 3 to 6 membered cycloalkyl. $R^{25}$ may be $R^{26}$-substituted or unsubstituted 3 to 6 membered cycloalkyl. $R^{25}$ may be $R^{26}$-substituted 3 to 6 membered cycloalkyl.

$R^{25}$ may be substituted or unsubstituted 3 to 20 membered heterocycloalkyl. $R^{25}$ may be substituted 3 to 20 membered heterocycloalkyl. $R^{25}$ may be unsubstituted 3 to 20 membered heterocycloalkyl. $R^{25}$ may be $R^{26}$-substituted or unsubstituted 3 to 20 membered heterocycloalkyl. $R^{25}$ may be $R^{26}$-substituted 3 to 20 membered heterocycloalkyl. $R^{25}$ may be substituted or unsubstituted 3 to 10 membered heterocycloalkyl. $R^{25}$ may be substituted 3 to 10 membered heterocycloalkyl. $R^{25}$ may be unsubstituted 3 to 10 membered heterocycloalkyl. $R^{25}$ may be $R^{26}$-substituted or unsubstituted 3 to 10 membered heterocycloalkyl. $R^{25}$ may be $R^{26}$-substituted 3 to 10 membered heterocycloalkyl. $R^{25}$ may be substituted or unsubstituted 3 to 6 membered heterocycloalkyl. $R^{25}$ may be substituted 3 to 6 membered heterocycloalkyl. $R^{25}$ may be unsubstituted 3 to 6 membered heterocycloalkyl. $R^{25}$ may be $R^{26}$-substituted or unsubstituted 3 to 6 membered heterocycloalkyl. $R^{25}$ may be $R^{26}$-substituted 3 to 6 membered heterocycloalkyl.

$R^{25}$ may be substituted or unsubstituted 5 to 20 membered aryl. $R^{25}$ may be substituted 5 to 20 membered aryl. $R^{25}$ may be unsubstituted 5 to 20 membered aryl. $R^{25}$ may be $R^{26}$-substituted or unsubstituted 5 to 20 membered aryl. $R^{25}$ may be $R^{26}$-substituted 5 to 20 membered aryl. $R^{25}$ may be substituted or unsubstituted 5 to 10 membered aryl. $R^{25}$ may be substituted 5 to 10 membered aryl. $R^{25}$ may be unsubstituted 5 to 10 membered aryl. $R^{25}$ may be $R^{26}$-substituted or unsubstituted 5 to 10 membered aryl. $R^{25}$ may be $R^{26}$-substituted 5 to 10 membered aryl. $R^{25}$ may be substituted or unsubstituted 5 to 6 membered aryl. $R^{25}$ may be substituted 5 to 6 membered aryl. $R^{25}$ may be unsubstituted 5 to 6 membered aryl. $R^{25}$ may be $R^{26}$-substituted or unsubstituted 5 to 6 membered aryl. $R^{25}$ may be $R^{26}$-substituted 5 to 6 membered aryl.

$R^{25}$ may be substituted or unsubstituted 5 to 20 membered heteroaryl. $R^{25}$ may be substituted 5 to 20 membered heteroaryl. $R^{25}$ may be unsubstituted 5 to 20 membered heteroaryl. $R^{25}$ may be $R^{26}$-substituted or unsubstituted 5 to 20 membered heteroaryl. $R^{25}$ may be $R^{26}$-substituted 5 to 20 membered heteroaryl. $R^{25}$ may be substituted or unsubstituted 5 to 10 membered heteroaryl. $R^{25}$ may be substituted 5 to 10 membered heteroaryl. $R^{25}$ may be unsubstituted 5 to 10 membered heteroaryl. $R^{25}$ may be $R^{26}$-substituted or unsubstituted 5 to 10 membered heteroaryl. $R^{25}$ may be $R^{26}$-substituted 5 to 10 membered heteroaryl. $R^{25}$ may be substituted or unsubstituted 5 to 6 membered heteroaryl. $R^{25}$ may be substituted 5 to 6 membered heteroaryl. $R^{25}$ may be unsubstituted 5 to 6 membered heteroaryl. $R^{25}$ may be $R^{26}$-substituted or unsubstituted 5 to 6 membered heteroaryl. $R^{25}$ may be $R^{26}$-substituted 5 to 6 membered heteroaryl.

$R^{26}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{27}$-substituted or unsubstituted alkyl (e.g. $C_1$-$C_8$ alkyl), $R^{27}$-substituted or unsubstituted heteroalkyl (e.g. 2 to 8 membered heteroalkyl), $R^{27}$-substituted or unsubstituted cycloalkyl (e.g. $C_3$-$C_8$ cycloalkyl), $R^{27}$-substituted or unsubstituted heterocycloalkyl (e.g. 3 to 6 membered heterocycloalkyl), $R^{27}$-substituted or unsubstituted aryl (e.g. 5 or 6 membered aryl), or $R^{27}$-substituted or unsubstituted heteroaryl (e.g. 5 or 6 membered heteroaryl).

$R^{27}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{28}$-substituted or unsubstituted alkyl (e.g. $C_1$-$C_8$ alkyl), $R^{28}$-substituted or unsubstituted heteroalkyl (e.g. 2 to 8 membered heteroalkyl), $R^{28}$-substituted or unsubstituted cycloalkyl (e.g. $C_3$-$C_8$ cycloalkyl), $R^{28}$-substituted or unsubstituted heterocycloalkyl (e.g. 3 to 6 membered heterocycloalkyl), $R^{28}$-substituted or unsubstituted aryl (e.g. 5 or 6 membered aryl), or $R^{28}$-substituted or unsubstituted heteroaryl (e.g. 5 or 6 membered heteroaryl).

$R^{28}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{29}$-substituted or unsubstituted alkyl (e.g. $C_1$-$C_8$ alkyl), $R^{29}$-substituted or unsubstituted heteroalkyl (e.g. 2 to 8 membered heteroalkyl), $R^{29}$-substituted or unsubstituted cycloalkyl (e.g. $C_3$-$C_8$ cycloalkyl), $R^{29}$-substituted or unsubstituted heterocycloalkyl (e.g. 3 to 6 membered heterocycloalkyl), $R^{29}$-substituted or unsubstituted aryl (e.g. 5 or 6 membered aryl), or $R^{29}$-substituted or unsubstituted heteroaryl (e.g. 5 or 6 membered heteroaryl).

$R^{29}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{30}$-substituted or unsubstituted alkyl (e.g. $C_1$-$C_8$ alkyl), $R^{30}$-substituted or unsubstituted heteroalkyl (e.g. 2 to 8 membered heteroalkyl), $R^{30}$-substituted or unsubstituted cycloalkyl (e.g. $C_3$-$C_8$ cycloalkyl), $R^{30}$-substituted or unsubstituted heterocycloalkyl (e.g. 3 to 6 membered heterocycloalkyl), $R^{30}$-substituted or unsubstituted aryl (e.g. 5 or 6 membered aryl), or $R^{30}$-substituted or unsubstituted heteroaryl (e.g. 5 or 6 membered heteroaryl).

$R^{30}$ halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

$R^{25}$ may have the formula:

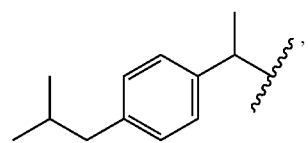

(1a)

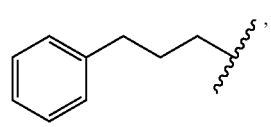

(2a)

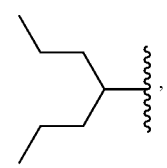

(3a)

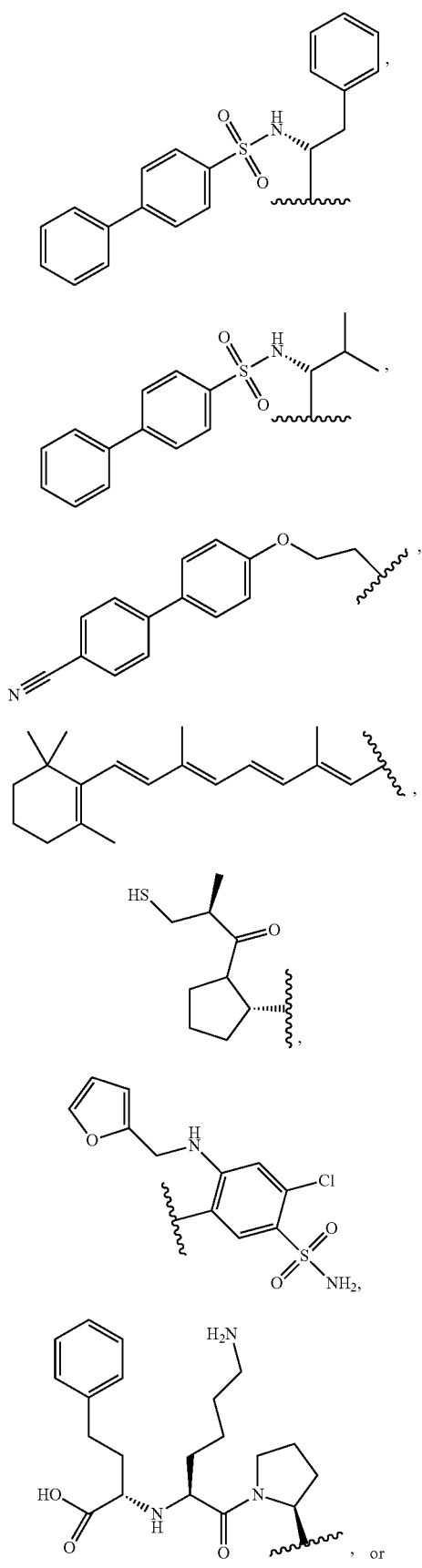
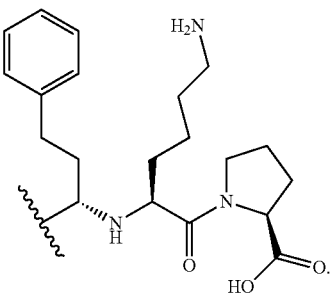

The compounds described herein may be synthesized using the methods described herein. In one aspect, the compounds are synthesized by contacting a carboxylic acid drug with a substituted or unsubstituted oxazolidinone, a substituted or unsubstituted oxazolidithione, a substituted or unsubstituted thiazolidinone, or a substituted or unsubstituted thiazolidithione using conditions described herein. The carboxylic drug may be a NSAID, a histone deacetylase (HDAC) inhibitor drug, a statin drug, leukotriene receptor antagonist drug, a fluoroquinolone drug, a matrix metalloproteinase (MMP) inhibitor drug, a cardiovascular therapy drug (e.g. an angiotensin-converting enzyme inhibitor drug (ACE drug), or an angiotensin II receptor blocker drug (ARB drug)), a furosemide drug or analogue thereof which has furosemide activity, or retinoic acid drug moiety including analogues thereof which have retinoic acid activity.

II. PHARMACEUTICAL COMPOSITIONS

Also provided herein are pharmaceutical compositions. In one aspect, the pharmaceutical composition includes a pharmaceutically acceptable excipient and a compound (i.e. prodrug) as described herein (e.g. formula (I), (II), (III), (IV), (V), (VI), or (VII), including embodiments thereof. The pharmaceutical composition may be administered to a subject in need thereof as described herein.

III. METHODS OF TREATMENT

Methods of treating a ROS-associated disease are provided herein. In one aspect, is a method of treating a ROS-associated disease in a subject in need thereof. The method includes administering a therapeutically effective amount of a compound (i.e. prodrug) described herein, including embodiments thereof to the subject. The prodrug moiety is removed from the prodrug upon contact with a ROS thereby forming a carboxylate drug. The carboxylate drug may be a NSAID, a histone deacetylase (HDAC) inhibitor drug, a statin drug, leukotriene receptor antagonist drug, a fluoroquinolone drug, a matrix metalloproteinase (MMP) inhibitor drug, a cardiovascular therapy drug (e.g. an angiotensin-converting enzyme inhibitor (ACE inhibitor), or an angiotensin II receptor blocker drug (ARB)), furosemide or analogue thereof which has furosemide activity, or retinoic acid including analogues thereof which have retinoic acid activity. The compound (i.e. prodrug) is as described herein (e.g. formula (I), (II), (III), (IV), (V), (VI), or (VII), including embodiments thereof.

The ROS-associated disease may be cancer. The cancer may be a solid tumor cancer. The cancer may be blood cancer. The cancer may be acute myeloid leukemia ("AML") or chronic myelogenous leukemia ("CML"). The cancer may be brain cancer, breast cancer, pancreatic cancer, colon cancer, liver cancer, kidney cancer, lung cancer, non-small cell lung cancer, melanoma, ovary cancer, sarcoma cancer, or prostate cancer. The cancer may be brain cancer. The cancer may be breast cancer. The cancer may be a pancreatic cancer. The cancer may be colon cancer. The cancer may be liver cancer. The cancer may be kidney cancer. The cancer may be lung cancer. The cancer may be non-small cell lung cancer. The cancer may be melanoma. The cancer may be ovary cancer. The cancer may be sarcoma cancer. The cancer may be prostate cancer.

The cancer may be treated by administering to the subject a prodrug as described herein. The drug moiety of the prodrug administered to the subject may be an anti-cancer drug moiety, an anti-inflammatory drug moiety (e.g. a NSAID moiety), a HDAC inhibitor drug moiety, an anti-folate drug moiety, a MMP inhibitor drug moiety, or a combination thereof. More than one prodrug, where each prodrugs has a different drug moiety may be co-administered as described herein. The more than one prodrug may include an anti-cancer drug moiety, a HDAC inhibitor drug moiety, an anti-folate drug moiety, a MMP inhibitor drug moiety or an anti-inflammatory drug moiety (e.g. a NSAID moiety). Thus, also provided herein are methods of treating cancer associated with ROS in a subject in need thereof by administering a therapeutically effective amount of a compound (i.e. prodrug) described herein.

The ROS-associated disease may be cardiovascular disease. The cardiovascular disease may be associated with hypertension or hypercholesterolemia, or an ischemic/reperfusion event (i.e. stroke or myocardial infarction). The ROS-associated cardiovascular disease may be treated by administering a prodrug described herein, where the drug moiety is a cardiovascular therapy drug moiety, a NSAID moiety, a furosemide drug moiety, or a statin drug moiety. The cardiovascular therapy drug moiety may be an ACE inhibitor drug moiety or a ARB drug moiety as described herein. The statin drug moiety may be an atorvastatin drug moiety. Thus, also provided herein are methods of treating cardiovascular disease associated with ROS in a subject in need thereof by administering a therapeutically effective amount of a compound (i.e. prodrug) described herein.

The ROS-associated disease may be fibrosis or a fibrotic disease. The fibrosis may be associated with inflammation, bacterial infection, overproduction or thick mucus, or vasoconstriction. The fibrosis may be treated by administering a prodrug described herein, where the drug moiety is a NSAID moiety, a fluoroquinolone drug moiety, or a LTRA drug moiety. The drug moiety may be a NSAID drug moiety as described herein. The drug moiety may be a fluoroquinolone drug moiety as described herein. The drug moiety may be a LTRA drug moiety as described herein. The fibrosis may be treated by administering combination of the drug moieties described above (e.g. two or more NSAID moities or an NSAID moiety and a fluoroquinolone drug moiety).

The ROS-associated disease may be a neurodegenerative disease or neurological disorder. The neurodegenerative disease may be treated with by administering a prodrug described herein. The drug moiety of the administered prodrug may be an anti-inflammatory drug moiety (e.g. a NSAID moiety) or an MMP inhibitor drug moiety. The neurodegenerative disease may be Alzheimer's disease. The neurodegenerative disease may be ALS. The neurodegenerative disease may be Parkinson's disease.

The ROS-associated disease may be an inflammatory disease. The inflammatory disease may be treated by administering a prodrug as described herein. The prodrug may include a NSAID moiety. The drug moiety may be a COX inhibitor drug moiety as described herein. The drug moiety may be an ibuprofen drug moiety, a dexibuprofen drug moiety, a naproxen drug moiety, a fenoprofen drug moiety, a ketoprofen drug moiety, a dexketoprofen drug moiety, a flurbiprofen drug moiety, an oxaprozin drug moiety, or a loxoprofen drug moiety, or analogues thereof which retain anti-inflammatory activity. The inflammatory disease may be treated by co-administering more than one prodrug, where each prodrug has a different NSAID moiety.

The removal of the prodrug moiety and formation of the carboxylate drug may occur at a targeted location. That is, the overexpression of ROS at a disease site (e.g. site of inflammation or site of tumor) may allow for targeting of the prodrug to a specific location in the subject. The activity of the drug is masked until the prodrug reaches the site of ROS overexpression where the prodrug moiety is removed and the carboxylate drug is formed.

The carboxylate drug may be a non-steroidal anti-inflammatory drug (NSAID), a histone deacetylase (HDAC) inhibitor drug, a statin drug, leukotriene receptor antagonist drug, a fluoroquinolone drug, a matrix metalloproteinase (MMP) inhibitor drug, a cardiovascular therapy drug (e.g. an angiotensin-converting enzyme (ACE inhibitor) inhibitor drug, or an angiotensin II receptor blocker drug (ARB)), furosemide or analogue thereof which retains furosemide activity, or retinoic acid drug including analogues thereof which retain retinoic acid activity.

The carboxylate drug may a NSAID. The NSAID may be a COX inhibitor drug. The COX inhibitor drug may be a salicylate drug or a salicylate-analogue drug. The COX inhibitor drug may be acetylsalicylic acid drug, diflunisal drug, salsalate drug, or choline magnesium trisalicylate drug, including analogues thereof which have COX inhibitor drug activity. The COX inhibitor drug may be a propionic acid COX inhibitor drug. The COX inhibitor drug may be an ibuprofen drug, a dexibuprofen drug, a naproxen drug, a fenoprofen drug, a ketoprofen drug, a dexketoprofen drug, a flurbiprofen drug, an oxaprozin drug, or a loxoprofen drug, including analogues thereof having COX inhibitor drug activity. The COX inhibitor drug may be an ibuprofen drug, or an analogue thereof which has ibuprofen activity. The COX inhibitor drug may be a dexibuprofen drug, or an analogue thereof which has dexibuprofen activity. The COX inhibitor drug may be a naproxen drug, or an analogue thereof which has naproxen activity. The COX inhibitor drug may be a fenoprofen drug, or an analogue thereof which has fenoprofen activity. The COX inhibitor drug may be a ketoprofen drug, or an analogue thereof which has ketoprofen activity. The COX inhibitor drug may be a dexketoprofen drug, or an analogue thereof which has dexketoprofen activity. The COX inhibitor drug may be a flurbiprofen drug, or an analogue thereof which has flurbiprofen activity. The COX inhibitor drug may be an oxaprozin, or an analogue thereof which has oxaprozin activity. The COX inhibitor drug may be a loxoprofen drug, or an analogue thereof which has loxoprofen activity.

The COX inhibitor drug may be an acetic acid COX inhibitor drug. The COX inhibitor drug may be an indomethacin drug, a tolmetin drug, a sulindac drug, an etodolac drug, a ketorolac drug, a diclofenac drug, or an aceclofenac drug, including analogues thereof having activity. The COX inhibitor drug may be an indomethacin drug, or an analogue thereof which has indomethacin activity. The COX inhibitor drug may be a tolmetin drug, or an analogue thereof which has tolmetin activity. The COX inhibitor drug may be a sulindac drug, or an analogue thereof which has sulindac activity. The COX inhibitor drug may be an etodolac drug, or an analogue thereof which has etodolac activity. The COX inhibitor drug may be a ketorolac drug, or an analogue thereof which has ketorolac activity. The COX inhibitor drug may be a diclofenac drug, or an analogue thereof which has diclofenac activity. The COX inhibitor drug may be an aceclofenac drug, or an analogue thereof which has aceclofenac activity.

The COX inhibitor drug may be an anthranilic acid COX inhibitor drug. The COX inhibitor drug may be a mefenamic acid drug, a meclofenamic acid drug, a flufenamic acid drug, or a tolfenamic acid drug, including analogues thereof having activity. The COX inhibitor drug may be a mefenamic acid drug, or an analogue thereof which has mefenamic acid activity. The COX inhibitor drug may be a meclofenamic acid drug, or an analogue thereof which has meclofenamic acid activity. The COX inhibitor drug may be a flufenamic acid drug, or an analogue thereof which has flufenamic acid activity. The COX inhibitor drug may be a tolfenamic acid drug, or an analogue thereof which has tolfenamic acid activity.

The COX inhibitor drug may be an ibuprofen drug, a dexibuprofen drug, a naproxen drug, a fenoprofen drug, a ketoprofen drug, a dexketoprofen drug, a flurbiprofen drug, an oxaprozin drug, or a loxoprofen drug. The COX inhibitor drug may be an indomethacin drug, a tolmetin drug, a sulindac drug, an etodolac drug, a ketorolac drug, a diclofenac drug, an aceclofenac drug, a mefenamic acid drug, a meclofenamic acid drug, a flufenamic acid drug, a tolfenamic acid drug, an acetylsalicylic acid drug, a diflunisal drug, a salsalate drug, a choline magnesium trisalicylate drug, or a licofelone drug. The COX inhibitor drug may be iso-butyl-propanoic-phenolic acid drug.

The carboxylate drug may be a HDAC inhibitor drug. The HDAC inhibitor may be a Class I HDAC inhibitor drug, a Class II HDAC inhibitor drug, a Class III HDAC inhibitor drug or a Class IV HDAC inhibitor drug. The HDAC inhibitor may be a phenylbutyric acid drug or valproic acid drug. The HDAC inhibitor may be a phenylbutyric acid drug. The HDAC inhibitor may be a valproic acid drug.

The carboxylate drug may be a statin drug. The statin drug may be an atorvastatin drug, a cerivastatin drug, a fluvastatin drug, a pitavastatin drug, or a rosuvastatin drug. The statin drug may be an atorvastatin drug. The statin drug may be a cerivastatin drug. The statin drug may be a fluvastatin drug. The statin drug may be a pitavastatin drug. The statin drug may be a rosuvastatin drug.

The carboxylate drug may be a leukotriene receptor antagonist drug. The leukotriene receptor antagonist drug may be a montelukast drug or an analogue which has montelukast activity.

The carboxylate drug may be a fluoroquinolone drug. The fluoroquinolone drug may be a ciprofloxin drug, a balofloxacin drug, a grepafloxacin drug, a levofloxacin drug, a pazufloxacin drug, a sparfloxacin drug, a temafloxacin drug, a tosufloxacin drug, a clinafloxacin drug, a gatifloxacin drug, a gemifloxacin drug, a moxifloxacin drug, a sitafloxacin drug, a trovafloxacin drug, a prulifloxacin drug, a delafloxacin drug, a JNJ-Q2 drug, or a nemonoxacin drug, or an analogue thereof which has antibacterial activity. The fluoroquinolone drug may be a ciprofloxin drug, or an analogue thereof which has antibacterial activity. The fluoroquinolone drug may be a balofloxacin drug, or an analogue thereof which has antibacterial activity. The fluoroquinolone drug may be a grepafloxacin drug, or an analogue thereof which has antibacterial activity. The fluoroquinolone drug may be a levofloxacin drug, or an analogue thereof which has antibacterial activity. The fluoroquinolone drug may be a pazufloxacin drug, or an analogue thereof which has antibacterial activity. The fluoroquinolone drug may be a sparfloxacin drug, or an analogue thereof which has antibacterial activity. The fluoroquinolone drug may be a temafloxacin drug, or an analogue thereof which has antibacterial activity. The fluoroquinolone drug may be a clinafloxacin drug, or an analogue thereof which has antibacterial activity. The fluoroquinolone drug may be a gatifloxacin drug, or an analogue thereof which has antibacterial activity. The fluoroquinolone drug may be a gemifloxacin drug, or an analogue thereof which has antibacterial activity. The fluoroquinolone drug may be a moxifloxacin drug, or an analogue thereof which has antibacterial activity. The fluoroquinolone drug may be a sitafloxacin drug, or an analogue thereof which has antibacterial activity. The fluoroquinolone drug may be a trovafloxacin drug, or an analogue thereof which has antibacterial activity. The fluoroquinolone drug may be a prulifloxacin drug, or an analogue thereof which has antibacterial activity. The fluoroquinolone drug may be a delafloxacin drug, or an analogue thereof which has antibacterial activity. The fluoroquinolone drug may be a JNJ-Q2 drug, or an analogue thereof which has antibacterial activity. The fluoroquinolone drug may be a nemonoxacin drug, or an analogue thereof which has antibacterial activity.

The drug may be derived from a matrix metalloproteinase inhibitor drug. The MMP inhibitor drug that inhibits MMP1, MMP2, MMP3, or MMP9. The MMP inhibitor drug may be a sulfonamide-based MMP inhibitor drug (e.g. aryl-sulfonamides, cyclic sulfonamides). The MMP inhibitor drug may be BAY 12-9566.

The anti-cancer drug may be an anti-cancer alkylating drug. The anti-cancer alkylating drug may be a bendamustine drug, a melphalan drug, or a chlorambucil drug. The anti-cancer alkylating drug may be a bendamustine drug. The anti-cancer alkylating drug may be a melphalan drug. The anti-cancer alkylating drug moiety may a chlorambucil drug.

The carboxylate drug may be a cardiovascular therapy drug. The cardiovascular therapy drug may be an ACE inhibitor drug. The ACE inhibitor drug may be an enalapril drug, a ramipril drug, a quinapril drug, a perindopril drug, a lisinopril drug, a benazepril drug, an imidapril drug, a trandolapril drug, or a cilazapril drug. The ACE inhibitor drug may be an enalapril drug. The ACE inhibitor drug may be a ramipril drug. The ACE inhibitor drug may be a quinapril drug. The ACE inhibitor drug may be a perindopril drug. The ACE inhibitor drug may be a lisinopril drug. The ACE inhibitor drug may be a benazepril drug. The ACE inhibitor drug may be an imidapril drug. The ACE inhibitor drug may be a trandolapril drug. The ACE inhibitor drug may be a cilazapril drug.

The cardiovascular therapy agent drug may be an ARB drug. The ARB drug may be a valsartan drug, a telmisartan drug, an azilsartan drug, or an olmesartan drug. The ARB drug may be a valsartan drug. The ARB drug may be a telmisartan drug. The ARB drug may be an azilsartan drug. The ARB drug may be an olmesartan drug.

The carboxylate drug may be furosemide or an analogue thereof which has furosemide activity. The carboxylate drug may be retinoic acid or an analogue thereof which has retinoic acid activity. The carboxylate drug may be an anti-folate drug. The anti-folate drug may be a methotrexate drug or a pemetrexed drug. The anti-folate drug may be a methotrexate drug. The anti-folate drug may be a pemetrexed drug.

The carboxylate drug may have the formula:

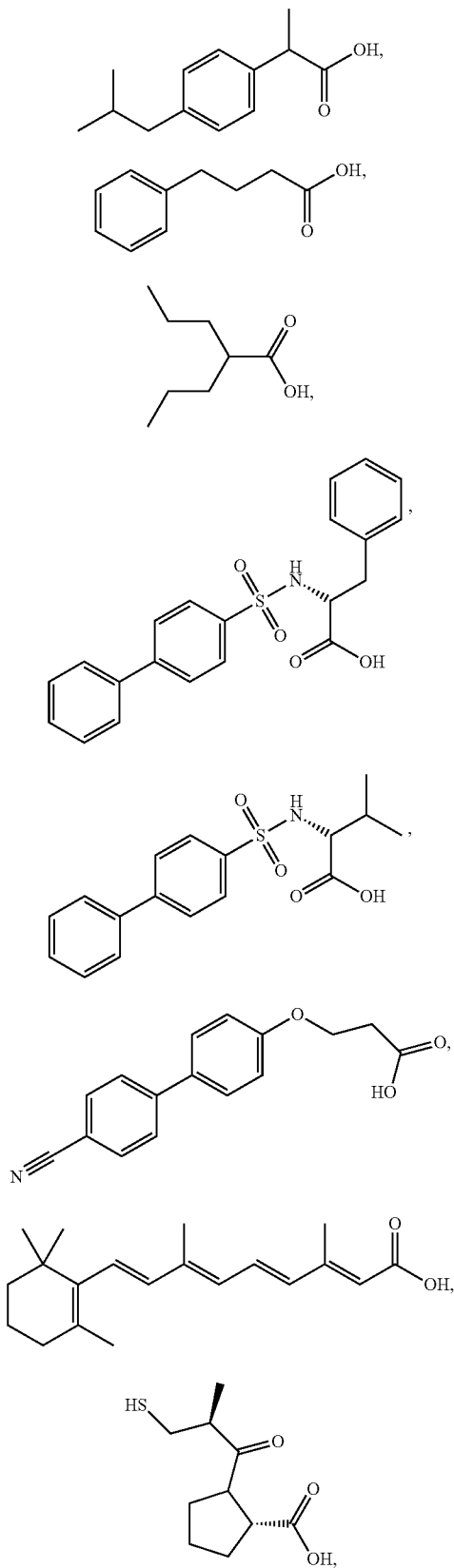

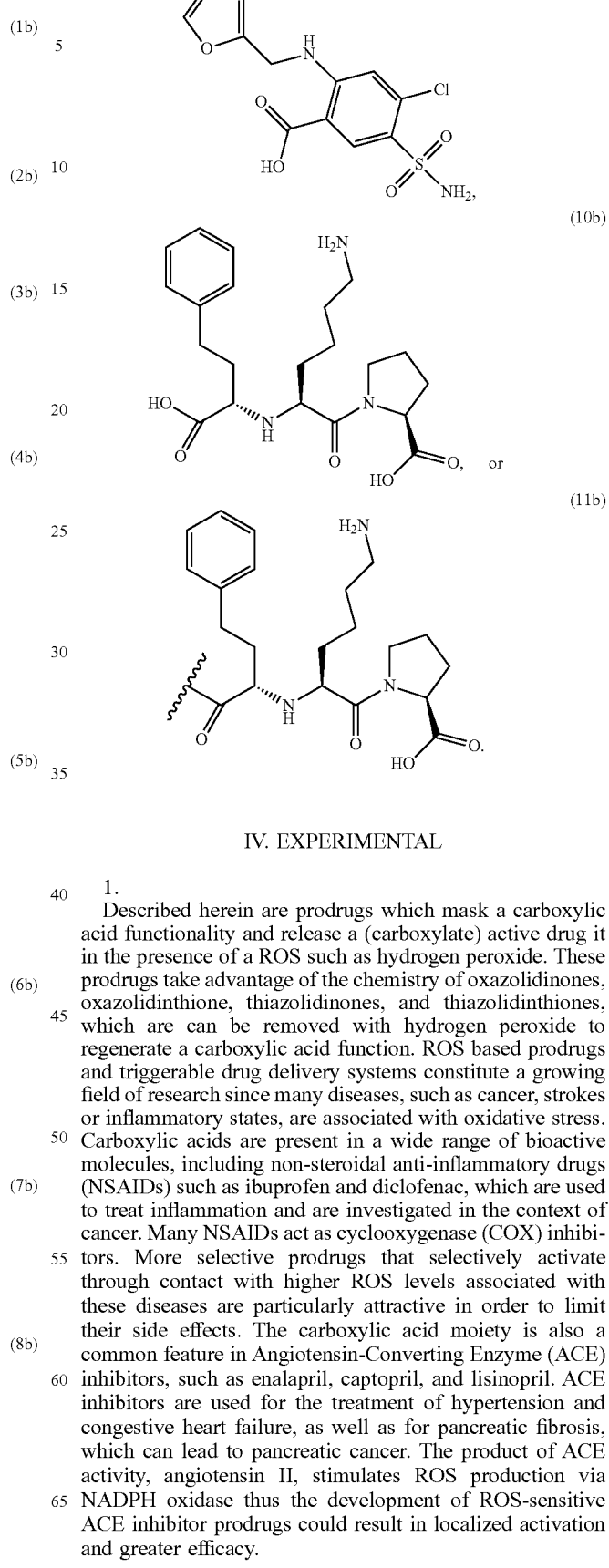

IV. EXPERIMENTAL

1.

Described herein are prodrugs which mask a carboxylic acid functionality and release a (carboxylate) active drug it in the presence of a ROS such as hydrogen peroxide. These prodrugs take advantage of the chemistry of oxazolidinones, oxazolidinthione, thiazolidinones, and thiazolidinthiones, which are can be removed with hydrogen peroxide to regenerate a carboxylic acid function. ROS based prodrugs and triggerable drug delivery systems constitute a growing field of research since many diseases, such as cancer, strokes or inflammatory states, are associated with oxidative stress. Carboxylic acids are present in a wide range of bioactive molecules, including non-steroidal anti-inflammatory drugs (NSAIDs) such as ibuprofen and diclofenac, which are used to treat inflammation and are investigated in the context of cancer. Many NSAIDs act as cyclooxygenase (COX) inhibitors. More selective prodrugs that selectively activate through contact with higher ROS levels associated with these diseases are particularly attractive in order to limit their side effects. The carboxylic acid moiety is also a common feature in Angiotensin-Converting Enzyme (ACE) inhibitors, such as enalapril, captopril, and lisinopril. ACE inhibitors are used for the treatment of hypertension and congestive heart failure, as well as for pancreatic fibrosis, which can lead to pancreatic cancer. The product of ACE activity, angiotensin II, stimulates ROS production via NADPH oxidase thus the development of ROS-sensitive ACE inhibitor prodrugs could result in localized activation and greater efficacy.

Carboxylic acids are crucial motifs for bioactive molecules, and are often present in therapeutics such as COX and ACE inhibitors, playing the role of either a hydrogen bond acceptor or a metal-binding group. Contrary to current ROS-sequestering techniques that have been developed for ROS-sensitive prodrugs and drug-delivery systems, this system exploits the nucleophile properties of dioxidanide. Without being bound by any particular theory, this system appears to allow regeneration of the nucleophile at the end of the activation. Thus, the release of the bioactive agents would not decrease overtime, since hydrogen peroxide is not consumed in the process.

Current ROS or hydrogen peroxide triggered systems use triggers involving boronic acids, boronic esters, or sulfonic esters. Many boron-based systems have limitations, especially in the diversity of chemical functionalities that can be protected. Indeed, carboxylic acids cannot masked with these systems. Thus carboxylic acid prodrugs cannot be formed where the prodrug is a combination of a bond between a carboxylate moiety and the prodrug moiety. In contrast, the present invention describes the prodrug compounds with carboxylate groups generated after contact with reactive oxygene species.

Under physiological pH, hydrogen peroxide is deprotonated to give a dioxanide ion, a very potent nucleophile. This ion is used in chemical synthesis and is known when using Evans auxiliaries' to break the imide motif and release a carboxylic acid and oxazolidinone. Further, dioxanide ion has been used in Crimmins' chemistry with oxazolidinethione and thiazolidinethione. This cleavage uses hydrogen peroxide as an organocatalyst.

2.

In this study, an approach for ROS-activated prodrugs based on a thiazolidinone prodrug moiety was examined. Thiazolidinones are used as auxiliaries for asymmetric reactions and are commonly referred to as Evan's auxiliaries. These groups are $H_2O_2$ responsive protecting groups—that is the thiazolidinone moiety (prodrug moiety) can be removed in the presence of $H_2O_2$. The prodrug moiety effectively masks the carboxylic acid groups of pharmacologically potent agents. In the presence of elevated levels of ROS, the prodrug moiety is hydrolyzed and generates the free carboxylic acid of the drug (Scheme 1). Developed herein are carboxylic acid prodrugs which are responsive to $H_2O_2$, stabile in a simulated physiological environment, and possess an inhibitory profile of the prodrugs compared to the ROS-activated drug of interest.

Scheme 1. Proposed mechanism of activation of a thiazoladinone prodrug of ibuprofen

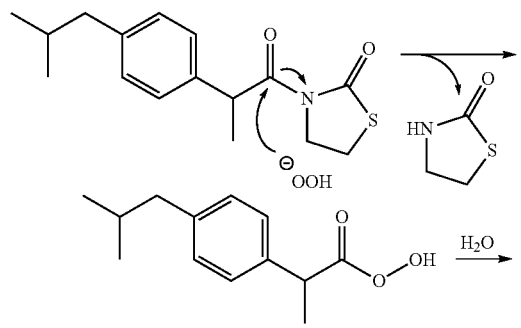

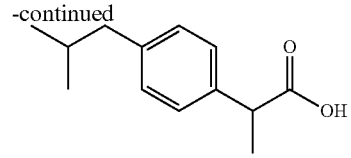

Initial studies were performed on four distinct but closely related prodrug moieties: oxazolidinone (A), oxazolidithione (B), thiazolidinone (C), and thiazolidithione (D) (FIG. 1). Each of these groups was appended to two model compounds, benzoic acid and phenyl acidic acid. These model compounds were chosen to examine the reactivity of aromatic and aliphatic carboxylic acids containing prodrugs.

Compounds A and D were commercially available, while the synthesis for B and C had been previously reported. The formation of the amide bond between the acid and the prodrug moiety was performed via two different methods: addition of DCC, DMAP in $CH_2Cl_2$ ("Method I") or through the Schotten-Baumann reaction ("Method ii"), with the corresponding acid-chloride.

To be effective prodrugs must have good water solubility and be rapidly converted to the active drug under the desired stimulus. These two aspects were evaluated first in model systems. Compounds 1-8 were treated with excess of $H_2O_2$ (27 equiv) in buffer, and deprotection was monitored via analytical HPLC. An authentic HPLC trace of each was obtained and was then compared to a trace obtained after 1 h and 4 h of incubation. After 4 h of incubation, compounds 1, 2, 5, and 6 displayed variable rates of deprotection, ranging from 1-67% conversion to the acid (Table 1). Compounds 3, 4, 7 and 8, all of which contain a thione-based prodrug moiety, displayed full deprotection. The stability of each compound was tested at physiological pH (100 mM TRIS-HCl, pH 7.2) as well as in the presence of glutathione (9 equiv). Compounds 1, 2, 5, and 6 displayed stability in both conditions, >85% stability. In contrast, compounds 3, 4, 7 and 8, all showed poorer stability. Therefore the model compounds that displayed the optimal combination of rate of cleavage and good stability, were 2 and 6.

TABLE 1

Summary of percent conversion to acid from model compounds, in the presence of $H_2O_2$ (9 equiv) after incubation at RT. Traces were obtained at two different time points, 1 h and 4 h, from when the stock solution was initially made.

| Compound | 1 | 2 | 3 | 4 | 5 | 6 | 7 | 8 |
|---|---|---|---|---|---|---|---|---|
| 1 h | 14.6 | 13.6 | 44.7 | 48.5 | <1 | 23.3 | 81.6 | 87.6 |
| 4 h | 25.6 | 37.8 | >99 | >99 | <1 | 67.8 | >99 | >99 |

3.

The success of the model compounds 2 and 6, both of which utilize the B prodrug moiety, prompted the investigation of the scope of this prodrug approach with an FDA approved drug, ibuprofen, and a well-studied matrix metalloproteinase (MMP) inhibitor (MMPi). FIG. 1. Ibuprofen is a non-selective cyclooxygenase (COX) inhibitor, and its chronic use as an analgesic and anti-inflammatory has been associated with formation of ulcers and gastrointestinal bleeding. A ROS-responsive prodrug strategy would aid in diminishing adverse side effects, since it would target the COX-2 isoform, which is mainly induced in areas of inflammation. MMPi also stand to benefit from a ROS prodrug strategy. MMP overexpression has been associated with ischemia-reperfusion events, in which its misregulation leads to accelerated matrix degradation, which disrupts the blood-brain barrier (BBB), and therefore increases the infarct size.

Figure 2:
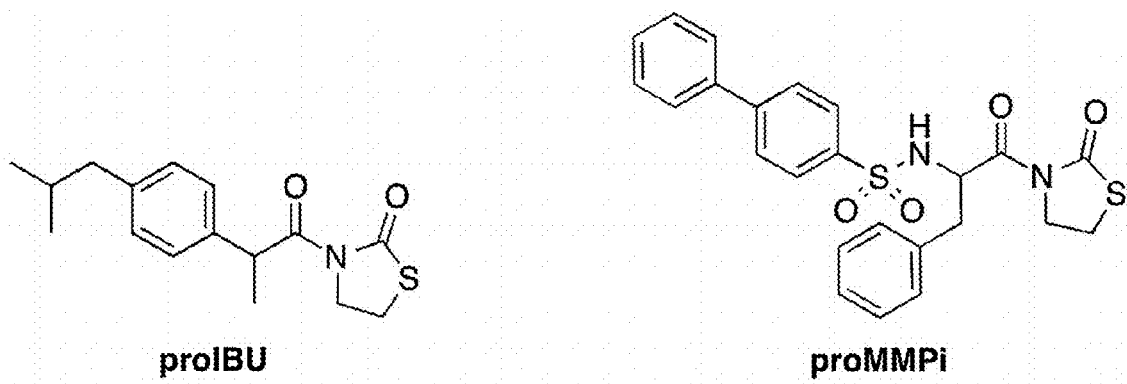
FIG. 2 Synthesized versions of prodrugs of ibuprofen and an MMP inhibitor.

Prodrug moiety B was appended to ibuprofen and MMPi in the same manner as the model compounds (Method i or ii). Both prodrug versions of (proIBU and proMMPi, see FIG. 2) were evaluated for hydrolytic stability via analytical HPLC under simulated physiological conditions. Initially, an authentic HPLC trace was obtained of proIBU and proMMPi, and a second trace was obtained after incubating in buffer (100 mM TRIS-HCl, pH 7.4) for 24 h at 37° C. Each prodrug was incubated in the same conditions, with the addition of 20 equivalents of lysine, serine and glutathione, all in distinct trials. This was done in order to demonstrate that the prodrug moiety is not readily cleaved in the presence of biologically relevant nucleophiles. ProIBU displayed remarkable stability >99% for all different conditions. Table 2.

TABLE 2

Summary of stability of model compounds in several simulated physiological conditions. Compounds were initially dissolved in DMSO and further diluted with the specified buffer, then incubated at RT for 24 h. Stability in the presence of glutathione (9 equiv) was also evaluated.

| Compound | 1 | 2 | 3 | 4 | 5 | 6 | 7 | 8 |
|---|---|---|---|---|---|---|---|---|
| HEPES, pH 7.2 | >99 | 88.6 | 95.5 | 57.0 | >99 | >99 | 54.6 | 32.5 |
| HEPES, pH 8.0 | >99 | 82.5 | 41.2 | 54.8 | 94.5 | >99 | 24.4 | <1 |
| HEPES, pH 7.2 + GSH | >99 | >99 | 59.5 | 77.6 | 86.3 | >99 | 45.7 | 39.5 |

Figure 3:
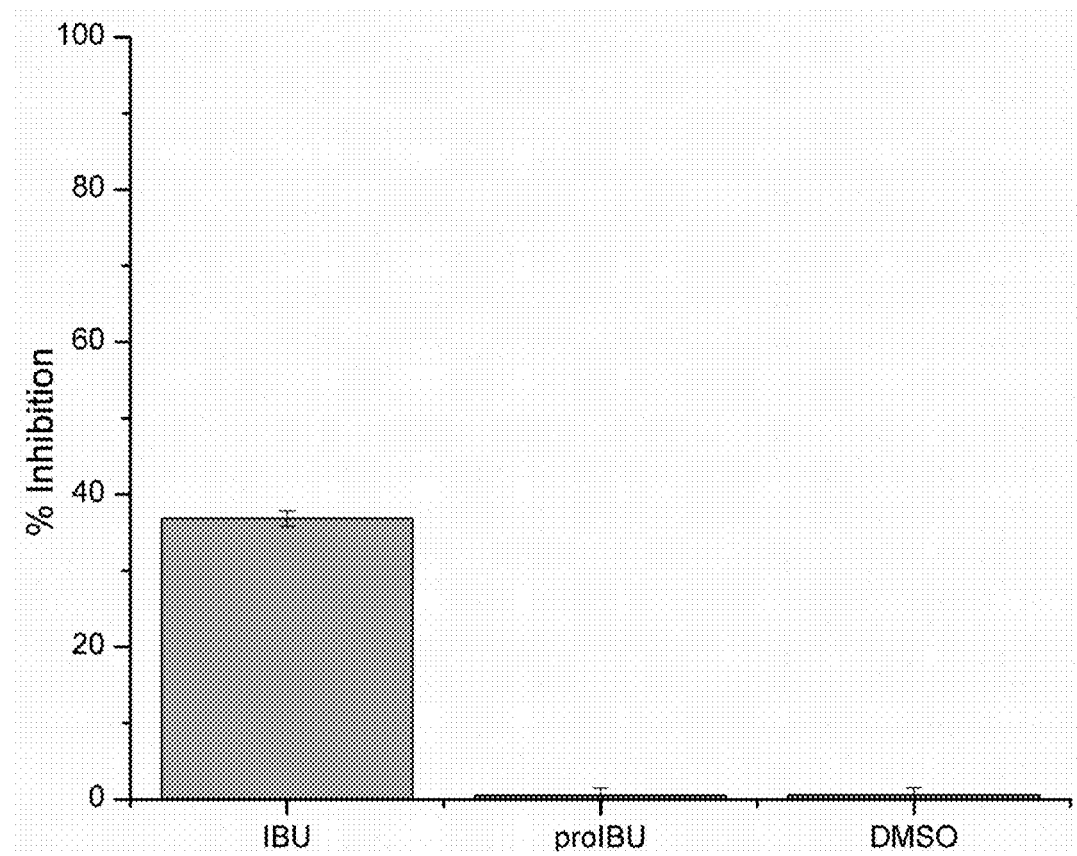
FIG. 3 Percent inhibition of proIBU and ibuprofen against COX-1.
Figure 4:
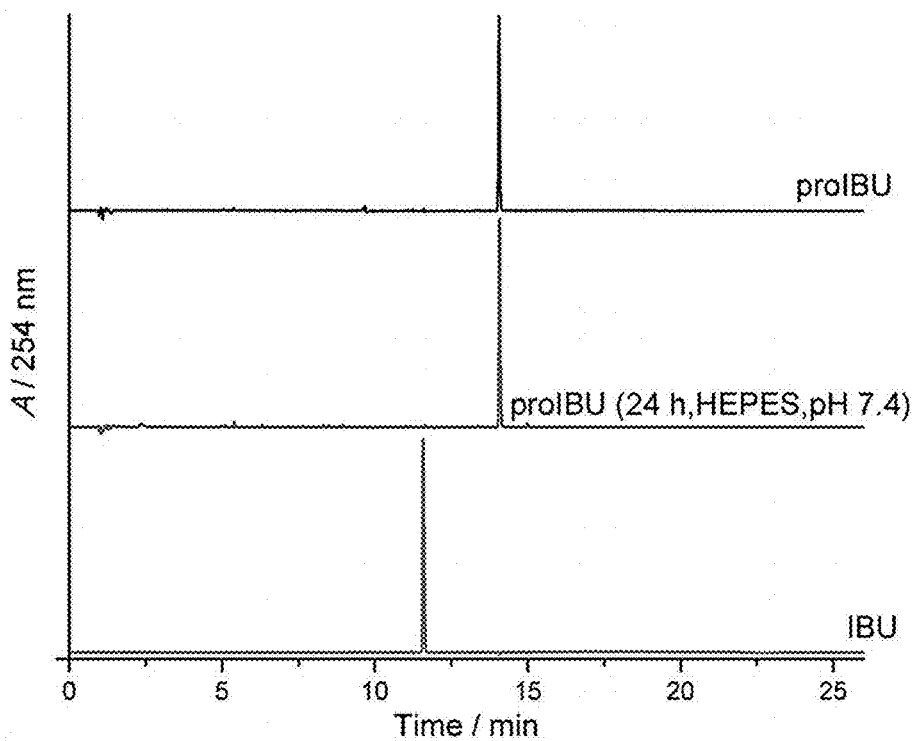
FIG. 4 A) HPLC trace of proIBU (Ret. Time=14.06 min), proIBU after a 24 h (37° C.) incubation in buffer (50 mM HEPES, pH 7.4) (Ret. Time=14.06 min) and ibuprofen (IBU) (Ret. Time=11.57 min); B) HPLC trace of proIBU (Ret. Time=14.06 min), proIBU after a 24 h (37° C.) incubation in buffer (100 mM Tris-Cl, pH 8.0) (Ret. Time=14.06 min) and IBU (Ret. Time=11.57 min).
Figure 4:
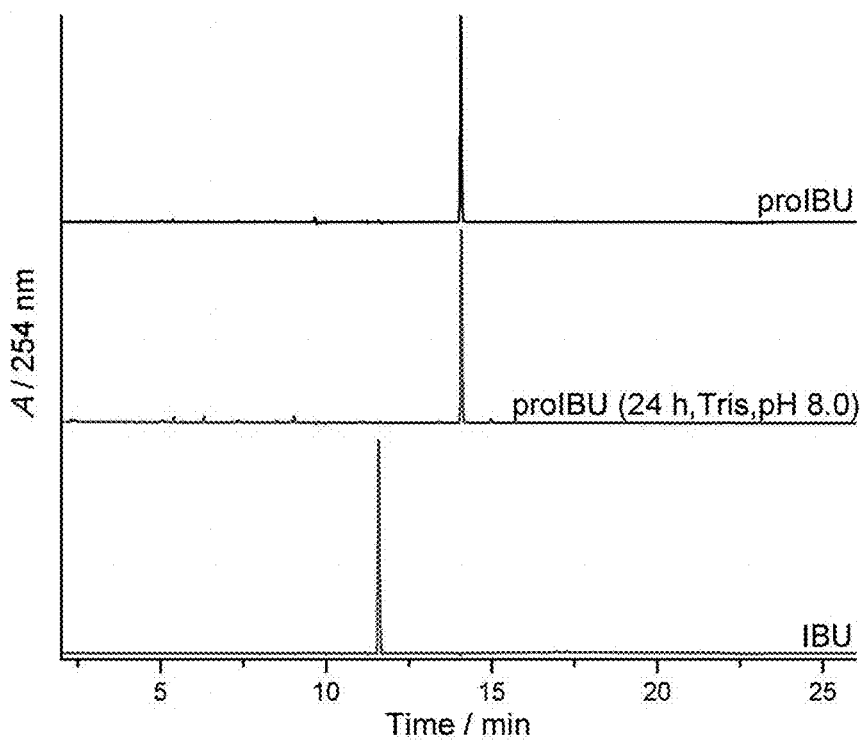
Figure 5:
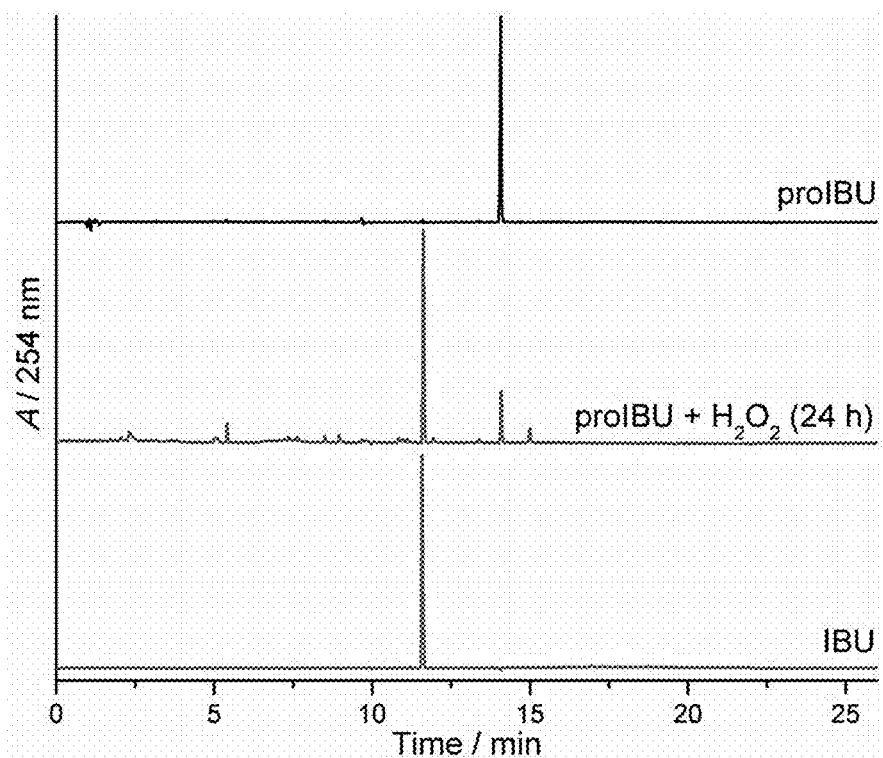
FIG. 5 A) HPLC trace of proIBU (Ret. Time=14.06 min), proIBU after a 24 h (37° C.) incubation with 20 equivalents of H$_2$O$_2$ in buffer (50 mM HEPES, pH 7.4) (Ret. Time=14.06, Ret. Time=11.57 min) and IBU (Ret. Time=11.57 min); B) HPLC trace of proIBU (Ret. Time=14.06 min), proIBU after a 4 h (37° C.) incubation with 20 equivalents of $H_2O_2$ in buffer (100 mM Tris-Cl, pH 8.0) (Ret. Time=14.06, Ret. Time=11.57 min), proIBU after a 6 h (37° C.) incubation with 20 equivalents of $H_2O_2$ in buffer (100 mM Tris-Cl) (Ret. Time=11.57 min, teal) and IBU (Ret. Time=11.57 min).
Figure 5:
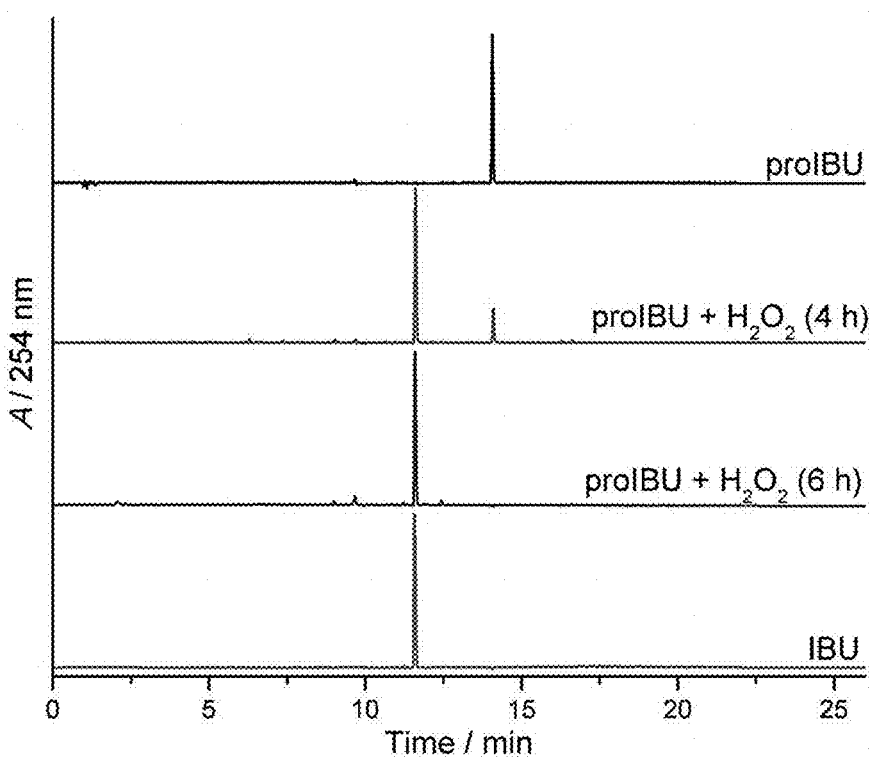
Figure 6:
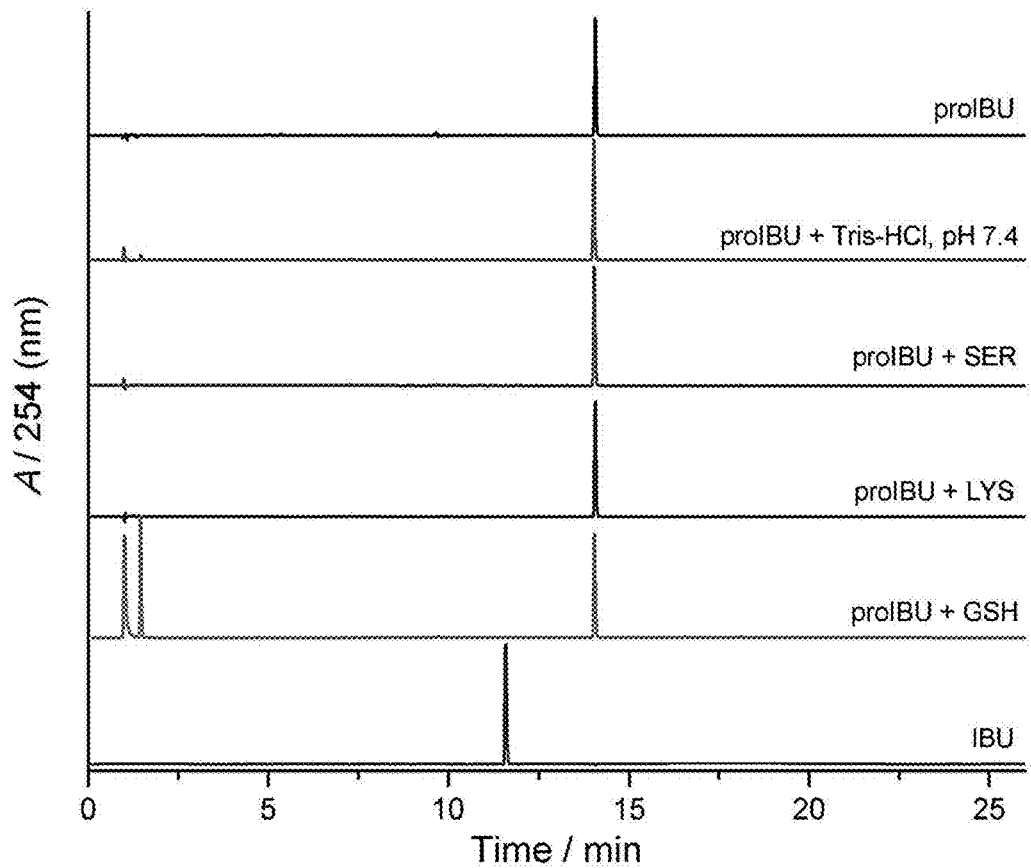
FIG. 6 HPLC trace of proIBU (Ret. Time=14.06 min), proIBU after a 24 h (37° C.) incubation in buffer (100 mM Tris-Cl, pH 7.4) (Ret. Time=14.06), proIBU after a 24 h (37° C.) incubation in buffer (100 mM Tris-Cl, pH 7.4) with 20 equivalents of serine (Ret. Time=14.06), proIBU after a 24 h (37° C.) incubation in buffer (100 mM Tris-Cl, pH 7.4) with 20 equivalents of lysine (Ret. Time=14.06), proIBU after a 24 h (37° C.) incubation in buffer (100 mM Tris-Cl, pH 7.4) with 20 equivalents of glutathione (Ret. Time=14.06), and IBU (Ret. Time=11.57 min).
Figure 7:
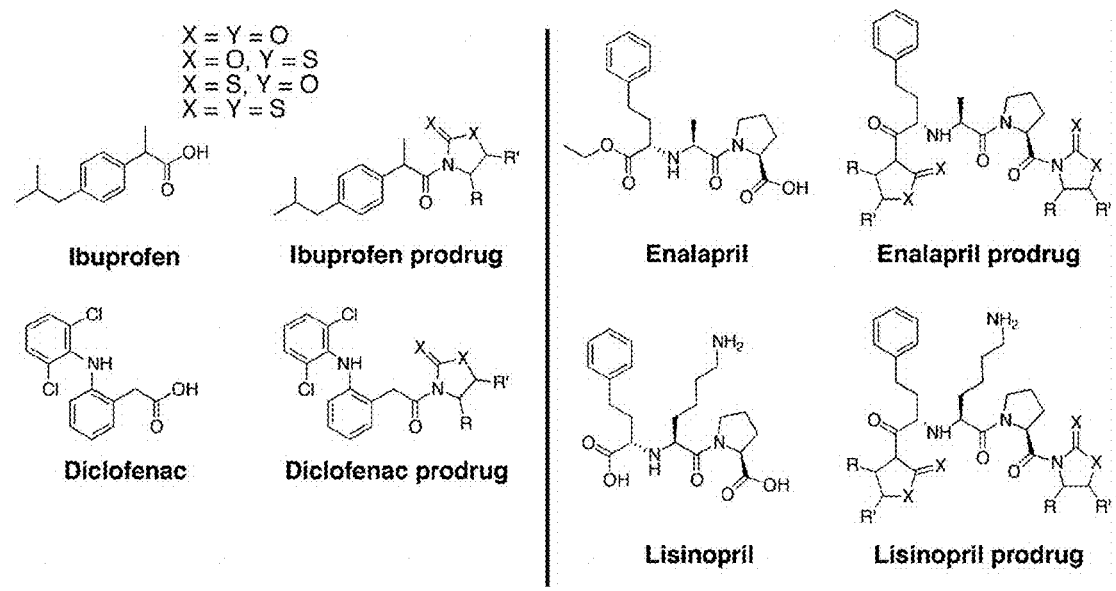
FIG. 7 Schematic of common COX and ACE inhibitors and ROS prodrugs thereof.
Figure 8:
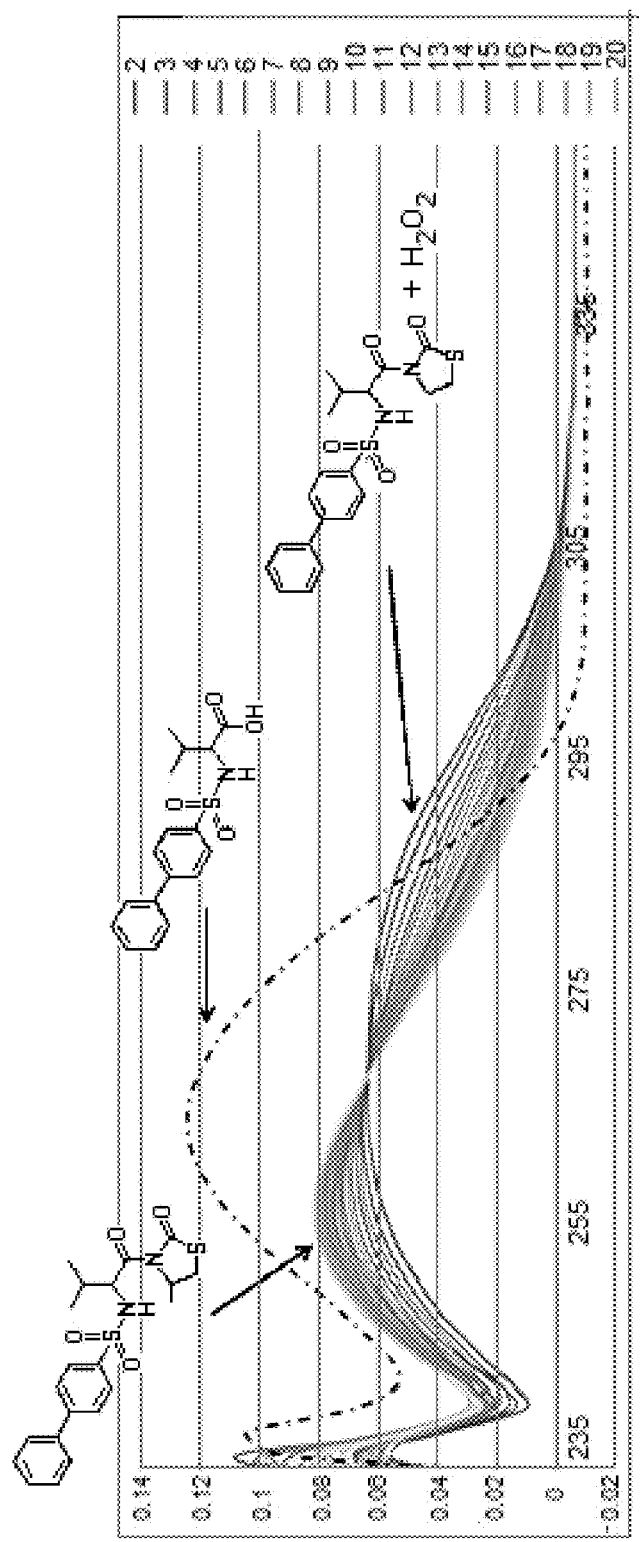
FIG. 8 Cleavage of proMMP inhibitor prodrug moiety and release of drug followed by UV/Vis.
Figure 9:
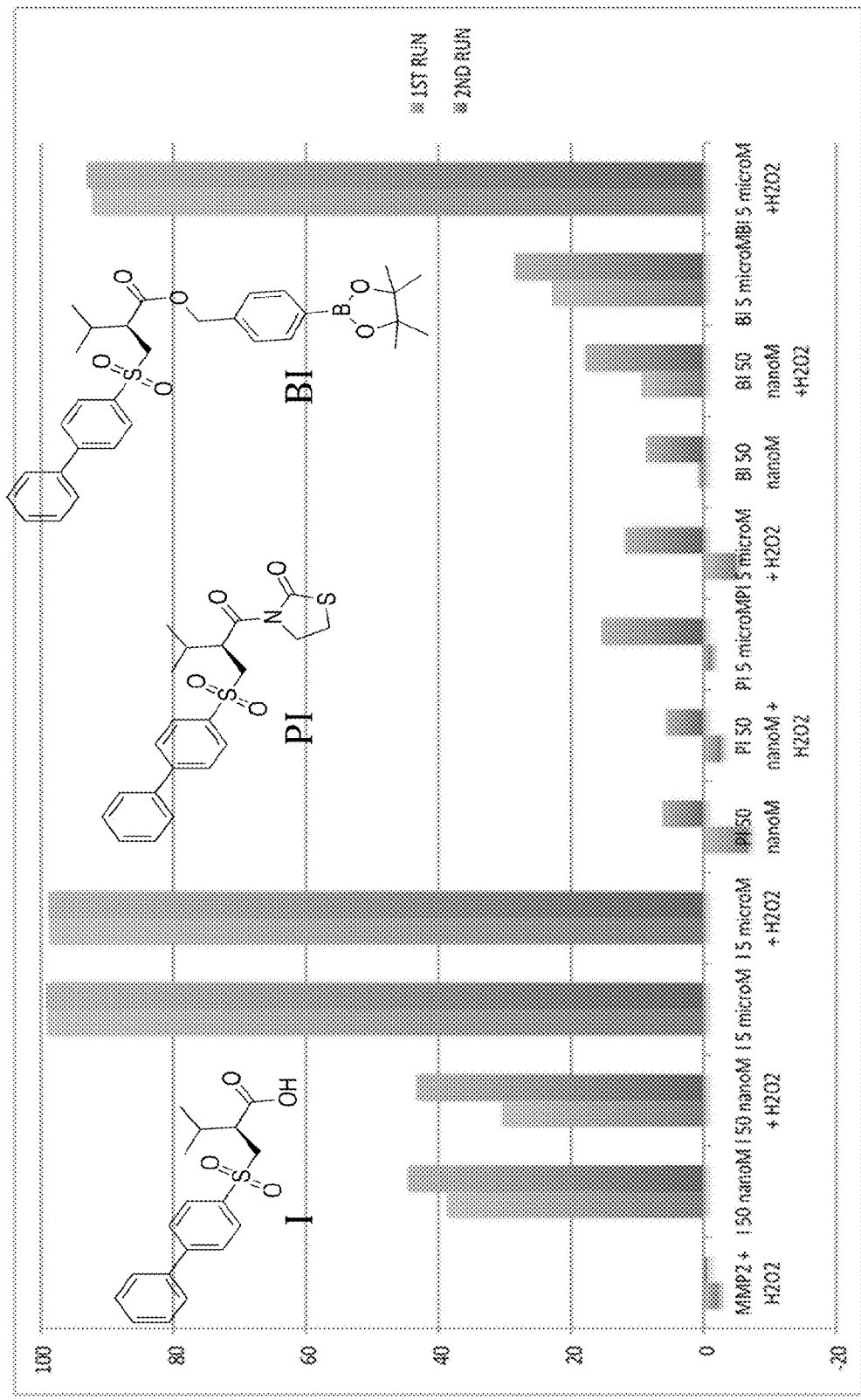
FIG. 9 MMP-2 inhibition assay (% inhibition).
Figure 10:
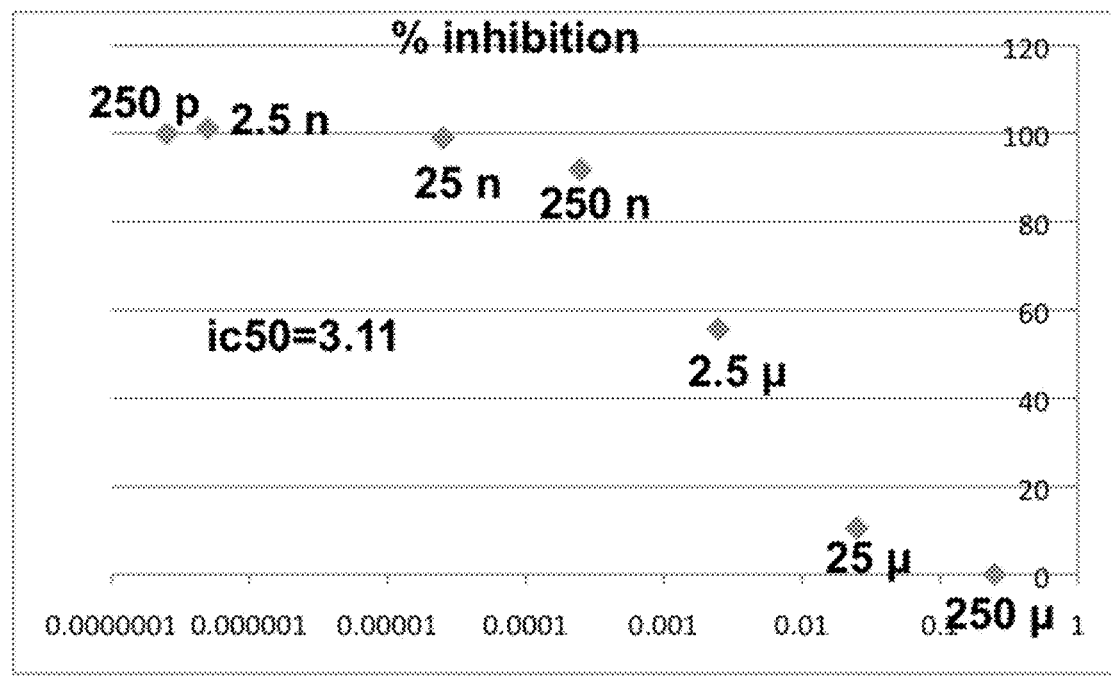
FIG. 10 $IC_{50}$ study of MMP inhibitor.
Figure 10:
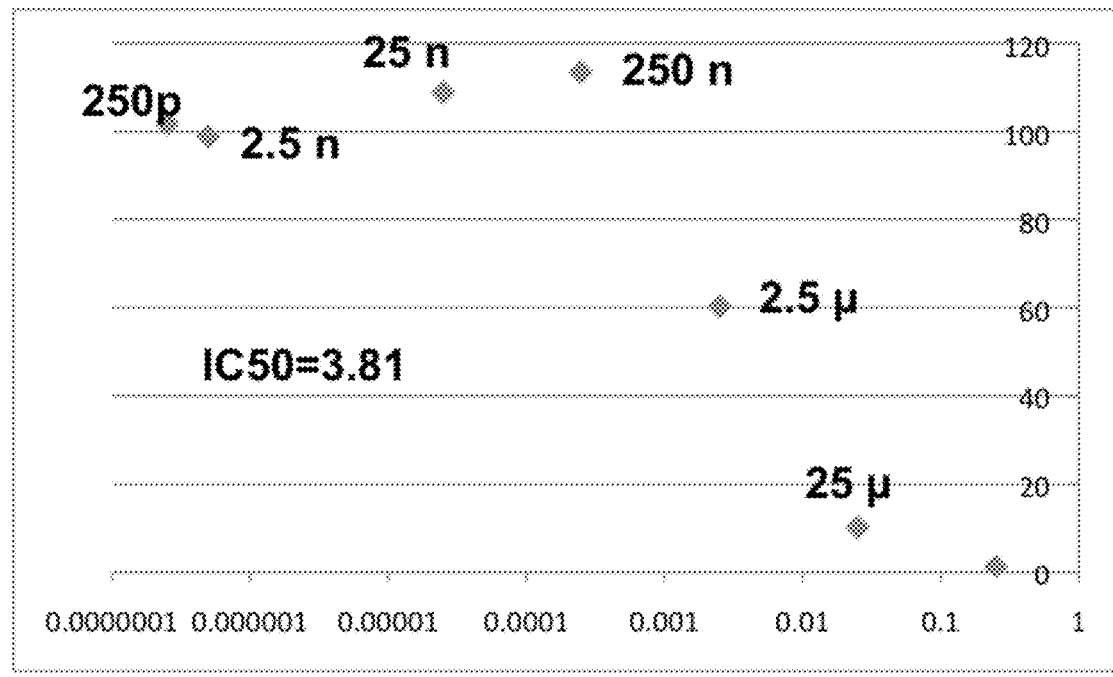

The efficacy of the prodrug to inhibit its target was also evaluated. For proIBU a commercially available fluorescent assay was utilized. ProIBU was tested against both isoforms of the COX enzyme. The inhibition assays demonstrated little to no inhibition by proIBU. Table 1 and FIG. 3.

4.

Histone deacetylases (HDACs) are implicated in cancer and appear, in part, responsible for aberrant expression of cellular proteins and other factors in the propagation of cancer. Thus, administering HDAC inhibitors has been shown effective to treating certain types of cancer.

We investigated two clinically relevant HDAC inhibitors, phenylbutyric acid and valproic acid. Prodrugs of these compounds were synthesized as described.

Scheme 9. Synthesis of the Evans-based prodrugs of phenylbutyric acid and valproic acid (conditions for i are indicated in the methods herein).

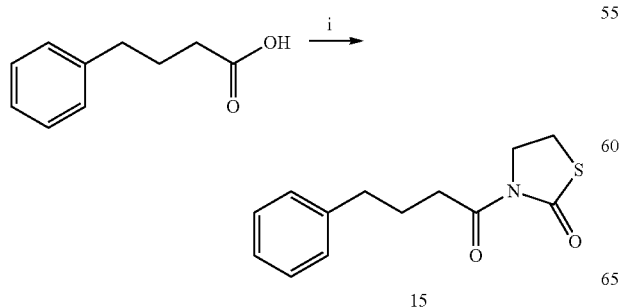

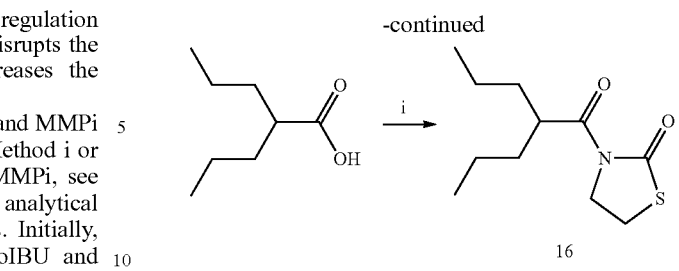

5.

Matrix metalloproteinases (MMPs) are enzymes implicated in cancer and cardiovascular disorders. Several MMP inhibitors possess carboxylic acid functional groups and are potent inhibitors of MMP activity. Sulfonamide-based MMPi compounds were investigated herein. Compounds were synthesized as described below.

Yield 16.5%. MS-ESI$^+$ m/z=(M−H)$^-$: 509.3 (M−CO$_2$−H)$^-$: 465.3).

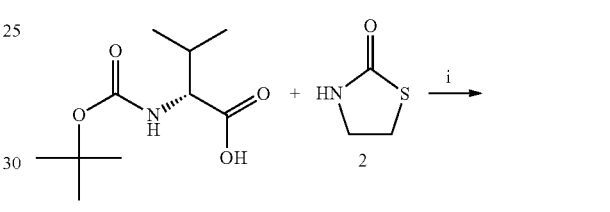

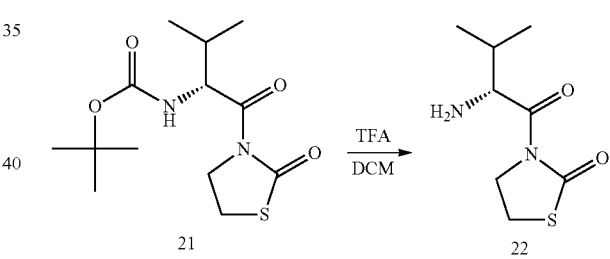

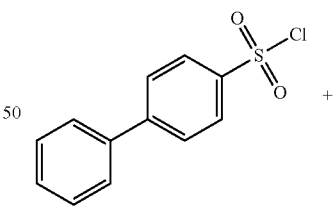

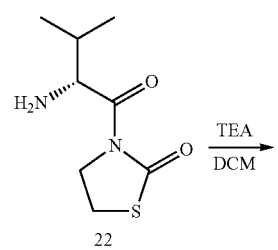

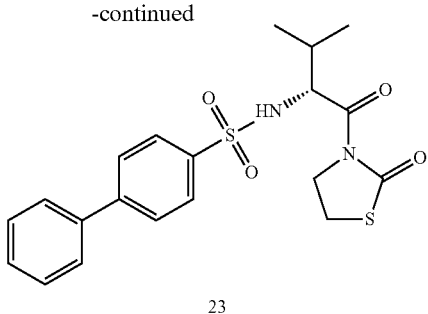

23

1 eq. of Boc-valine (217 mg) was treated with method i. After purification, the compound was deprotected in a mixture of TFA/DCM 10 ml and dried under vacuum to get compound 22. Yield: 61%. $^1$H-NMR (400 MHz, CD$_2$Cl$_2$, δ) 0.93 (d, $^3$J=6.8 Hz, 3H, a), 1.04 (d, $^3$J=6.8 Hz, 3H, b), 2.2-2.22 (m, 1H, c), 2.74-2.79 (m, 2H, d), 3.64-3.68 (m, 2H, e), 3.95-3.96 (m, 1H, f). MS-ESI$^+$ m/z=(M+Na)$^+$: 225.2.

1 eq of compound 22 (154 mg) was dissolved in 10 ml dry DCM together with 1.1 eq of biphenyl sulfonyl chloride (123 mg) and 200 μL of TEA. The mixture was stirred for 4 h. The mixture was then extracted, washed, dried and evaporated under vacuum. The residue is purified by column to yield compound 23. Yield: 1.2%. $^1$H-NMR (400 MHz, CD$_2$Cl$_2$, δ) 0.88 (d, $^3$J=8 Hz, 3H), 1.00 (d, $^3$J=8 Hz, 3H), 2.16-2.18 (m, 1H), 3.23 (t, $^3$J=8 Hz, 2H), 3.76 (t, $^3$J=8 Hz, 2H), 3.90-3.92 (m, 1H), 5.76 (bs, 1H), 7.44-7.52 (m, 3H aromatics), 7.64 (d, $^3$J=8 Hz, 2H, aromatics), 7.80 (d, $^3$J=8 Hz, 2H, aromatics), 8.01 (d, $^3$J=8 Hz, 2H, aromatics). MS-ESI$^+$ m/z=(M+Na)': 477.1.

Yield: 5%. $^1$H-NMR (400 MHz, C$_H$Cl$_3$, δ) 3.44-3.48 (m, 3H, a, b), 3.70-3.75 (m, 1H, c), 4.30-4.43 (m, 2H, d), 5.26-5.29 (m, 1H, e), 7.01 (d, $^3$J=8.8 Hz, 2H, f), 7.52 (d, $^3$J=8.8 Hz, 2H, g), 7.62-7.70 (m, 3H, h, i). MS-ES$^{1+}$ m/z= (M–H)$^-$: 395.3

6.

Retinoic acid was synthesized as described below.

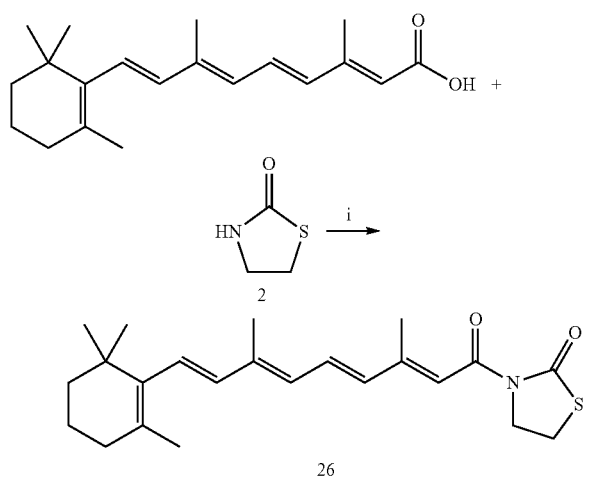

Protected Retin-A
$^1$H-NMR (500 MHz, CD$_2$Cl$_2$, δ) 1.01 (s, 6H, a), 1.44-1.46 (m, 2H, b), 1.58-1.61 (m, 2H, c), 1.69 (s, 3H, d), 1.99 (s, 3H, e), 2.00-2.02 (m, 2H, f), 2.29 (s, 3H, g), 3.25 (t, $^3$J=7.2 Hz, 2H, h), 4.14 (t, $^3$J=7.2 Hz, 2H, i), 6.12-6.17 (m, 2H, j) 6.29 (d, $^3$J=15.8 Hz, 1H, j) 6.39 (d, $^3$J=15.0 Hz, 1H, j), 6.74 (s, 1H, k), 7.06 (dd, $^3$J=15.0 Hz, $^3$J=11.5 Hz 1H, l). MS-ESI$^+$ m/z=(M+Na)$^+$: 408.3 (2M+Na)$^+$: 793.5.

7.

General:

All chemicals were purchased from commercial suppliers (Sigma-Aldrich, Acros Organics, TCI America) and were used without further purification, unless otherwise noted. Chromatography was performed using a CombiFlashRf 200 automated system from TeledyneISCO (Lincoln, USA). NMR spectra were recorded on a Varian FT 400 NMR instrument. Mass spectrometry (MS) was performed at the Molecular Mass Spectrometry Facility (MMSF) in the Department of Chemistry & Biochemistry at the University of California, San Diego.

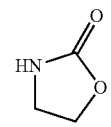

A

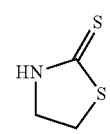

D

Oxazolidin-2-one (A) and thiazolidine-2-thione (D) were commercially available.

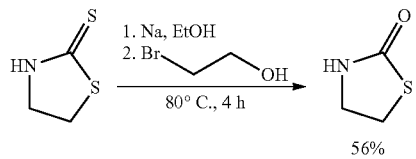

Synthesis of Thiazolidin-2-one (B)

To a solution of anhydrous EtOH (10 mL) in a dry vessel was added sodium (0.25 g, 11 mmol). The mixture was kept under N$_2$ atmosphere and stirred at RT for ~30 mins. To this was added thiazolidine-2-thione (D) (1.2 g, 10 mmol) and 2-bromoethanol (1.3 g, 10 mmol). The reaction heated to reflux for 4 h. At this point, reaction was allowed to cool to RT, then filtered to remove insoluble white solids, which were rinsed with anhydrous EtOH (3×10 mL). The filtrate was concentrated, then purified via silica gel chromatography eluting hexanes and ethyl acetate (EtOAc). This afforded B in 56% yield (0.64 g, 6.2 mmol). $^1$H NMR (400 MHz, Acetone-d$_6$) δ 6.91 (br s, 1H), 3.62 (t, J=7.2 Hz, 2H), 3.44 (t, J=7.2 Hz, 2H). ESI-MS(+): m/z 104.0 [M+H]$^+$, 126.0 [M+Na]$^+$.

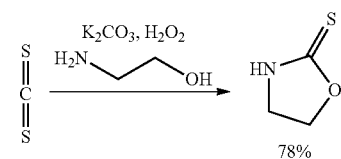

Synthesis of Oxazolidine-2-thione (C)

To a solution of 2-aminoethanol (6.1 g, 100 mmol) in EtOH (250 mL) was added of K$_2$CO$_3$ (6.9 g, 50 mmol) and carbon disulfide (15.2 g, 200 mmol). The mixture was heated to 40° C. H$_2$O$_2$ (30% w/w) (15.3 mL, 150 mmol) was slowly added over 1 h. The reaction was then allowed to cool to RT, and stirred for an additional 4 h. At this point, sat. NH$_4$Cl (aq, 10 mL) was added, and the solution was extracted with EtOAc (3×150 mL). The organic phases were combined, dried with MgSO$_4$, concentrated, then purified via silica gel chromatography eluting hexanes and EtOAc. This afforded C in 78% yield (4.0 g, 39 mmol). $^1$H NMR (400 MHz, Acetone-d$_6$) δ 8.63 (br, 1H), 4.66 (t, J=8.7 Hz, 2H), 3.81 (t, J=8.7 Hz, 2H). ESI-MS(+): m/z 104.0 [M+H]$^+$, 126.0 [M+Na]$^+$.

General Procedure for 1-8

Protocol for Amide Coupling (Method i):

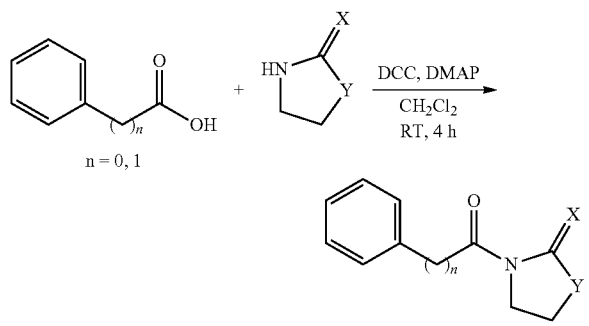

To a solution of carboxylic acid (1 mmol) in anhydrous CH$_2$Cl$_2$ (10 mL), was added DCC (1.1 mmol) and DMAP (1.1 mmol). The mixture was stirred at RT for 20 min followed by the addition of the corresponding amine (A-D) (1 mmol) and stirred for an additional 4 hours. The resulting solution was concentrated, then purified via silica gel chromatography eluting hexanes and EtOAc.

Protocol for Schotten-Baumann Reaction (Method ii)

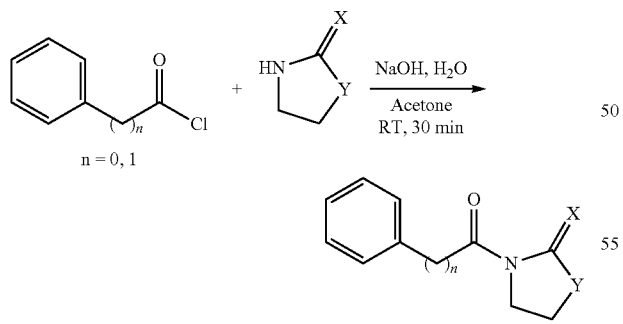

To a solution of A-D (12 mmol) in H$_2$O (5 mL) was added NaOH (15 mmol). To this was then added acetone (45 mL), followed by the addition of the corresponding acyl chloride (15 mmol). The mixture was stirred for 30 min at RT. Acetone was removed from solution under reduced pressure and the remaining aqueous solution was further diluted with H$_2$O (20 mL). This was then extracted with EtOAc (3×20 mL). The organic phases were combined and dried with MgSO$_4$, concentrated, then purified via silica gel chromatography eluting hexanes and EtOAc.

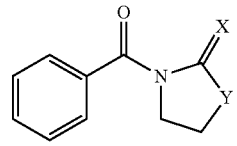

(1) X=Y=O; (2) X=O, Y=S; (3) X=S, Y=O; (4) X=Y=S

3-benzoyloxazolidin-2-one (1)

Yield for Method i: 72% (0.14 g, 0.72 mmol). $^1$H NMR (400 MHz, Acetone-d$_6$) δ 7.64-7.66 (m, 2H), 7.52-7.56 (m, 1H) 7.40-7.45 (m, 2H) 4.55 (t, J=7.7 Hz, 2H) 4.18 (t, J=7.7 Hz, 2H). ESI-MS(+): m/z 192.2 [M+H]$^+$, 214.1 [M+Na]$^+$.

3-benzoylthiazolidin-2-one (2)

Yield for Method i: 50% (0.10 g, 0.50 mmol. $^1$H NMR (400 MHz, Acetone-d$_6$) δ 7.62-7.65 (m, 2H), 7.52-7.56 (m, 1H), 7.41-7.45 (m, 2H), 4.25 (t, J=7.0 Hz, 2H), 3.55 (t, J=7.0 Hz, 2H). $^{13}$C NMR (100 MHz, Acetone-d$_6$) δ 172.4, 169.5, 134.8, 132.0, 129.1, 128.0, 48.7, 25.9. ESI-MS(+): m/z 230.0 [M+Na]$^+$.

Phenyl(2-thioxooxazolidin-3-yl)methanone (3)

Yield for Method i: 72% (0.15 g, 0.72 mmol). $^1$H NMR (400 MHz, Acetone-d$_6$) δ 7.71-7.73 (m, 2H), 7.54-7.58 (m, 1H), 7.42-7.46 (m, 2H), 4.77 (t, J=7.0 Hz, 2H), 4.36 (t, J=7.0 Hz, 2H). $^{13}$C NMR (100 MHz, Acetone-d$_6$) δ 187.7, 171.1, 134.5, 132.3, 129.5, 128.1, 68.2, 48.4. ESI-MS(+): m/z 230.0 [M+Na]$^+$.

Phenyl(2-thioxothiazolidin-3-yl)methanone (4)

Yield for Method i: 86% (0.19 g, 0.86 mmol). $^1$H-NMR (400 MHz, Acetone-d$_6$) δ 7.73-7.76 (m, 2H), 7.55-7.59 (m, 1H), 7.43-7.47 (m, 2H), 4.58 (t, J=7.2 Hz, 2H), 3.68 (t, J=7.2 Hz, 2H). ESI-MS(+): m/z 224.1 [M+H]$^+$, 246.0 [M+Na]$^+$.

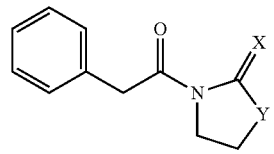

(5) X=Y=O; (6) X=O, Y=S; (7) X=S, Y=O; (8) X=Y=S

3-(2-phenylacetyl)oxazolidin-2-one (5)

Yield for Method ii: 82% (2.5 g, 12.3 mmol). $^1$H NMR (400 MHz, Acetone-d$_6$) δ 7.24-7.31 (m, 5H), 4.47 (t, J=7.8 Hz, 2H) 4.34 (s, 2H), 4.03 (t, J=7.8 Hz, 2H). ESI-MS(+): m/z 206.0 [M+H]', 226.0 [M+Na]$^+$.

3-(2-phenylacetyl)thiazolidin-2-one (6)

Yield for Method i: 41% (0.09 g, 0.41 mmol). $^1$H-NMR (400 MHz, Acetone-$d_6$) δ 7.24-7.32 (m, 5H), 4.17-4.20 (m, 4H), 3.42 (t, J=7.4 Hz, 2H). ESI-MS(+): m/z 222.1 [M+H]$^+$, 244.0 [M+Na]$^+$.

2-phenyl-1-(2-thioxooxazolidin-3-yl)ethan-1-one (7)

Yield for Method i: 63% (0.14 g, 0.63 mmol). $^1$H NMR (400 MHz, Acetone-$d_6$) δ 7.25-7.32 (m, 5H), 4.70 (s, 2H), 4.64 (t, J=7.6 Hz, 2H), 4.29 (t, J=7.6 Hz, 2H). ESI-MS(+): m/z 244.0 [M+Na]'.

2-phenyl-1-(2-thioxothiazolidin-3-yl)ethan-1-one (8)

Yield for Method i: 73% (0.17 g, 0.73 mmol). $^1$H NMR (400 MHz, Acetone-$d_6$) δ 7.25-7.33 (m, 5H), 4.63 (s, 2H), 4.61 (t, J=7.6 Hz, 2H), 3.44 (t, J=7.6 Hz, 2H). ESI-MS(+): m/z 260.0 [M+Na]$^+$.

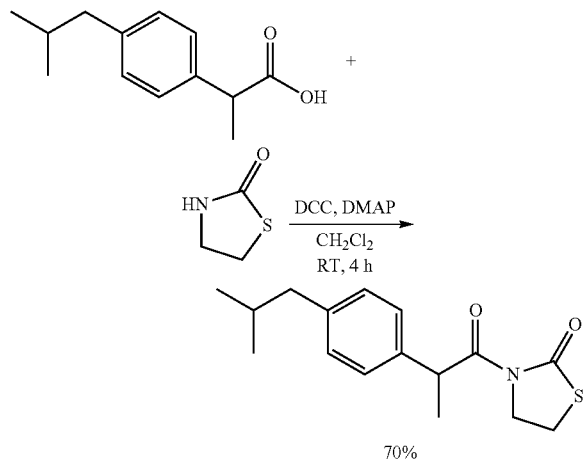

3-(2-(4-isobutylphenyl)propanoyl)thiazolidin-2-one (proIBU)

(Yield for Method i: 70%). $^1$H NMR (400 MHz, Acetone-$d_6$) δ 7.19 (d, J=8.1 Hz, 2H), 7.10 (d, J=8.1 Hz, 2H), 4.93 (q, J=7.0 Hz, 1H), 4.15-4.20 (m, 2H), 3.28-3.37 (m, 2H), 2.44 (d, J=7.2 Hz, 2H), 1.84 (sep J=6.7 Hz, 1H), 1.30 (d, J=7.0 Hz, 3H), 0.88 (d, J=6.7 Hz, 6H). $^{13}$C NMR (100 MHz, Acetone-$d_6$) δ 174.0, 172.2, 140.1, 138.5, 129.1, 127.8, 47.8, 44.7, 43.7, 30.1, 24.6, 21.8, 19.21. ESI-MS(+): m/z 292.2 [M+H]$^+$, 314.2 [M+Na]$^+$. HRMS calcd for $C_{16}H_{21}N\ O_2S\ Na$: 314.1185; Found: 314.1192.

HPLC Analysis
Method i:
Analytical HPLC was performed on an Agilent 1260 System equipped with a Poroshell 120 reverse-phase column (EC-C18, 4.6×100 mm, 2.7 µm). Separation was achieved with a flow rate of 1 mL min$^{-1}$ and the following mobile phase: 5% MeOH+0.1% formic acid in $H_2O$ (A) and 0.1% formic acid in MeOH (B). Starting with 95% A and 5% B, a linear gradient was run for 15 min to a final solvent mixture of 5% A and 95% B, which was held for 5 min before ramping back down to 95% A and 5% B over the course of 2 min, with constant holding at this level for 4 additional min. All compounds were initially dissolved in DMSO and further diluted with 50 mM HEPES, pH 7.2 buffer. Injections consisted of 100 µL, of a 50 µM.

Method ii:
Analytical HPLC was performed on a HP Series 1050 System equipped with a Poroshell 120 reverse-phase column (EC-C18, 4.6×100 mm, 2.7 µm). Separation was achieved with a flow rate of 1 mL min$^{-1}$ and the following mobile phase: 2.5% ACN+0.1% formic acid in $H_2O$ (A) and 0.1% formic acid in ACN (B). Starting with 95% A and 5% B, a linear gradient was run for 15 min to a final solvent mixture of 5% A and 95% B, which was held for 5 min before ramping back down to 95% A and 5% B over the course of 2 min, with constant holding at this level for 4 additional min. All compounds were initially dissolved in DMSO and further diluted with specified buffer. Injections consisted of 100 µl, of a 1 mM solution.

V. REFERENCES

Daniel, K. B., Major Jourden, J. L., Negoescu, K. E., and Cohen, S. M. (2010) Activation of sulfonate ester based matrix metalloproteinase proinhibitors by hydrogen peroxide, *J. Biol. Inorg. Chem.* 16, 313-323.

Major Jourden, J. L., and Cohen, S. M. (2010) Enzymatic activation of a matrix metalloproteinase inhibitor, *Chem. Commun.* 46, 1241-1243.

Major Jourden, J. L., and Cohen, S. M. (2010) Hydrogen Peroxide Activated Matrix Metalloproteinase Inhibitors: A Prodrug Approach, *Angew. Chem. Int. Ed.* 49, 6795-6797.

Major Jourden, J. L., Daniel, K. B., and Cohen, S. M. (2011) Investigation of self-immolative linkers in the design of hydrogen peroxide activated metalloprotein inhibitors, *Chem. Comm.* 47, 7968-7970.

Wang, Q., Tang, X. N., and Yenari, M. A. (2007) The inflammatory response in stroke, *J. Neuroimmunol.* 184, 53-68.

Lopez-Lazaro, M. (2007) Dual role of hydrogen peroxide in cancer: possible relevance to cancer chemoprevention and therapy, *Cancer Lett.* 252, 1-8.

Chang, M. C. Y., Pralle, A., Isacoff, E. Y., and Chang, C. J. (2004) A selective, cell-permeable optical probe for hydrogen peroxide in living cells, *J. Am. Chem. Soc.* 126, 15392-15393.

Miller, E. W., and Chang, C. J. (2007) Fluorescent probes for nitric oxide and hydrogen peroxide in cell signaling, *Curr. Opin. Chem. Biol.* 11, 620-625.

Sella, E., and Shabat, D. (2008) Self-immolative dendritic probe for direct detection of triacetone triperoxide, *Chem. Commun.*, 5701-5703.

Lo, L. C., and Chu, C. Y. (2003) Development of highly selective and sensitive probes for hydrogen peroxide, *Chem. Commun.*, 2728-2729.

Xu, K. H., Tang, B., Huang, H., Yang, G. W., Chen, Z. Z., Li, P., and An, L. G. (2005) Strong red fluorescent probes suitable for detecting hydrogen peroxide generated by mice peritoneal macrophages, *Chem. Commun.*, 5974-5976.

Charkoudian, L. K., Pham, D. M., and Franz, K. J. (2006) A pro-chelator triggered by hydrogen peroxide inhibits iron-promoted hydroxyl radical formation, *J. Am. Chem. Soc.* 128, 12424-12425.

Charkoudian, L. K., Pham, D. M., Kwon, A. M., Vangeloff, A. D., and Franz, K. J. (2007) Modifications of boronic ester pro-chelators triggered by hydrogen peroxide tune reactivity to inhibit metal-promoted oxidative stress, *Dalton Trans.*, 5031-5042.

Dickens, M. G., and Franz, K. J. (2010) A Prochelator Activated by Hydrogen Peroxide Prevents Metal-Induced Amyloid beta Aggregation, *ChemBioChem* 11, 59-62.

Kratz, F., Muller, I. A., Ryppa, C., and Warnecke, A. (2008) Prodrug strategies in anticancer chemotherapy, *ChemMedChem* 3, 20-53.

Rautio, J., Kumpulainen, H., Heimbach, T., Oliyai, R., Oh, D., Jarvinen, T., and Savolainen, J. (2008) Prodrugs: design and clinical applications, *Nat. Rev. Drug Disc.* 7, 255-270.

Hsieh, P. W., Hung, C. F., and Fang, J. Y. (2009) Current Prodrug Design for Drug Discovery, *Curr. Pharm. Des.* 15, 2236-2250.

Kuang, Y. Y., Baakrishnan, K., Gandhi, V., and Peng, X. H. (2011) Hydrogen Peroxide Inducible DNA Cross-Linking Agents: Targeted Anticancer Prodrugs, *J. Am. Chem. Soc.* 133, 19278-19281.

Cao, S., Wang, Y. B., and Peng, X. H. (2012) ROS-Inducible DNA Cross-Linking Agent as a New Anticancer Prodrug Building Block, *Chem. Eur. J.* 18, 3850-3854.

Karton-Lifshin, N., Segal, E., Omer, L., Portnoy, M., Satchi-Fainaro, R., and Shabat, D. (2011) A Unique Paradigm for a Turn-ON Near-Infrared Cyanine-Based Probe: Noninvasive Intravital Optical Imaging of Hydrogen Peroxide, *J. Am. Chem. Soc.* 133, 10960-10965.

Van de Bittner, G. C., Dubikovskaya, E. A., Bertozzi, C. R., and Chang, C. J. (2010) In vivo imaging of hydrogen peroxide production in a murine tumor model with a chemoselective bioluminescent reporter, *Proc. Natl. Acad. Sci. USA* 107, 21316-21321.

Kurumbail, R. G., Kiefer, J. R., and Marnett, L. J. (2001) Cyclooxygenase enzymes: catalysis and inhibition, *Curr. Opin. Struct. Biol.* 11, 752-760.

Rowlinson, S. W., Kiefer, J. R., Prusakiewicz, J. J., Pawlitz, J. L., Kozak, K. R., Kalgutkar, A. S., Stallings, W. C., Kurumbail, R. G., and Marnett, L. J. (2003) A novel mechanism of cyclooxygenase-2 inhibition involving interactions with Ser-530 and Tyr-385, *J. Biol. Chem.* 278, 45763-45769.

Menter, D. G., Schilsky, R. L., and DuBois, R. N. (2010) Cyclooxygenase-2 and Cancer Treatment: Understanding the Risk Should Be Worth the Reward, *Clin. Cancer Res.* 16, 1384-1390.

Reuter, S., Gupta, S. C., Chaturvedi, M. M., and Aggarwal, B. B. (2010) Oxidative stress, inflammation, and cancer How are they linked?, *Free Radic. Biol. Med.* 49, 1603-1616.

Watermeyer, J. M., Kroger, W. L., O'Neill, H. G., Sewell, B. T., and Sturrock, E. D. (2010) Characterization of domain-selective inhibitor binding in angiotensin-converting enzyme using a novel derivative of lisinopril, *Biochem. J.* 428, 67-74.

Sakurai, T., Kudo, M., Fukuta, N., Nakatani, T., Kimura, M., Park, A. M., and Munakata, H. (2011) Involvement of Angiotensin II and Reactive Oxygen Species in Pancreatic Fibrosis, *Pancreatology* 11, 7-13.

Brown, N. J., and Vaughan, D. E. (1998) Angiotensin-converting enzyme inhibitors, *Circulation* 97, 1411-1420.

Evans, D. A., Bender, S. L., and Morris, J. (1988) Total Synthesis of the Polyether Antibiotic X-206, *J. Am. Chem. Soc.* 110, 2506-2526.

Evans, D. A., Britton, T. C., and Ellman, J. A. (1987) Contrasteric Carboximide Hydrolysis with Lithium Hydroperoxide, *Tet. Lett.* 28, 6141-6144.

Stella, V. J; Charman, W. N.; Naringrekar, V. H. "Prodrugs. Do they have advantages in clinical practice?" *Drugs* 1985 29(5), 455-473.

Wu, K.-M. "A New Classification of Prodrugs: Regulatory Perspectives" *Pharmaceuticals* 2009 2(3), 77-81.

Pelicano, H.; Carney, D.; Huang, P. "ROS stress in cancer cells and therapeutic implications" *Drug Resist. Updates* 2004 7, 97-110.

Nagata, M. "Inflammatory cells and oxygen radicals" *Curr. Drug Targets Inflamm. Allergy* 2005 4(4), 503-504.

Haorah, S. H.; Ramirez, K.; Schall, D.; Smith, R.; Pandya, Y.; Persidsky, "Oxidative stress activates protein tyrosine kinase and matrix metalloproteinases leading to blood-brain barrier dysfunction" *J. Neurochem.* 2007 101, 566-576.

Rouffet, M.; Cohen, S. M. "Emerging Trends in Metalloprotein Inhibition" *Dalton Trans.* 2011, 40 3445-3454.

Major Jourden, J. L.; Cohen, S. M. "Hydrogen Peroxide Activated Matrix Metalloproteinase Inhibitors—A Prodrug Approach" *Angew. Chem. Intl. Ed.* 2010, 49, 6795-6797.

Dickens, M. G.; Franz, K. J. "A Prochelator Activated by Hydrogen Peroxide Prevents Metal-Induced Amyloid β Aggregation" *ChemBioChem* 2010 11(1), 59-62.

Messina, P.; Labbé, E.; Buriez, O.; Hillard, E. A.; Vessières, A.; Hamels, D.; Top, S.; Jaouen, G.; Frapart, Y. M.; Mansuy, D.; Amatore, C. "Deciphering the activation sequence of ferrociphenol anticancer drug candidates." *Chemistry* 2012 18(21): 6581-6587.

Evans, D. A.; Britton, T. C.; Ellman, J. A. "Contrasteric carboximide hydrolysis with lithium hydroperoxide" *Tet. Lett.* 1987 28(49) 6141-6144.

Crimmins, M. T.; King, B. W.; Tabet, A. E. "Asymmetric Aldol Additions with Titanium Enolates of Acyloxazolidinethiones: Dependence of Selectivity on Amine Base and Lewis Acid Stoichiometry". *J. Am. Chem. Soc.* 1997 119(33), 7883-7884.

Crimmins M. T.; Chaudhary K. "Titanium enolates of thiazolidinethione chiral auxiliaries: Versatile tools for asymmetric aldol additions." *Org. Lett.* 2000 2(6), 775-777.

Kurumbail, R. G.; Stevens, A. M.; Gierse, J. K.; McDonald, J. J.; Stegeman, R. A.; Pak, J. Y.; Gildehaus, D.; Miyashiro, J. M.; Penning, T. D.; Seibert, K.; Isakson, P. C.; Stallings, W. C. "Structural basis for selective inhibition of cyclooxygenase-2 by anti-inflammatory agents." *Nature* 1996 384, 644-648.

Marks, P. A.; Dokmanovic, M. *Expert Opinion on Investigational Drugs* 2005 14, 1497-1522.

De Ruijter, A. J. M.; Van Gennip, A. H.; Caron, H. N.; Kemp, S.; Van Kuilenburg, A. B. P. *Biomedical Journal* 2003 370, 737-749.

Dokmanovic, M.; Marks, P. A. *Journal of Cellular Biochemistry* 2005 96, 293-304.

Deng, X.; Chen, N.; Wang, Z.; Li, X.; Hu, H.; Xu, J. *Phosphorus, Sulfur Silicon Relat. Elem.* 2011 186, 1563-1571.

Jalce, G.; Franck, X.; Figadère, B. *Eur. J. Org. Chem.* 2009, 378-386.

Mundy, B. P.; Kim, Y. *J. Heterocyclic Chem.* 1982 19, 1221-1222.

Izawa, T.; Mukaiyama, T. *Bull. Chem. Soc. Jpn.* 1979 52(2), 555-558.

Shibata, I.; Baba, A.; Matsuda, H. *J. Chem. Soc., Chem. Commun.* 1986, 1703-1704.

Suzuki, T.; Hamashima, Y.; Sodeoka, M. *Angew. Chem. Int. Ed.* 2007 46, 5435-5439.

Sakamoto, M; Watanbe, S.; Fujita, T.; Aoyama, H.; Omote, Y. *J. Chem. Soc. Perkin Trans I* 1991, 2541-2545.

Izawa, T.; Mukaiyama, T. *Chem. Lett.* 1977 1443-1446.

Major-Jourden, J.; Cohen, S. M. *Angew. Chem. Int. Ed.* 2010 49, 6795-6797.

Seaver, B.; Smith, J. R. "Inhibition of COX Isoforms by Nutraceuticals" *J. Herbal Pharmacother.* 2004 4(2), 11-18.

Gurvich, N.; Tsygankova, O. M.; Meinkoth, J. L.; Klein, P. S. "Histone deacetylase is a target of valproic acid-mediated cellular differentiation." *Cancer Res.* 2004, 64, 1079-86

Bradner, J. E.; West, N.; Grachan, M. L.; Greenberg, E. F.; Haggarty, S. J.; Warnow, T.; mazitschek, R. "Chemical phylogenetics of histone deacetylases" *ACS Med. Chem. Lett.* 2011 2, 39-42.

Riester, D.; Hildmann, C.; Schwienhorst, A. "Histone deacetylase inhibitors—turning epigenic mechanisms of gene regulation into tools of therapeutic intervention in malignant and other diseases" *Appl. Microbiol. Biotechnol.* 2007 75, 499-514

Chung, T. K.; Funk, M. A.; Baker, D. H. "L-2-Oxothiazolidine-4-Carboxylate as a Cysteine Precursor: Efficacy for Growth and Hepatic Glutathione Synthesis in Chicks and Rats" *The Journal of Nutrition* 1990 158-165.

Stella, V. J; Charman, W. N.; Naringrekar, V. H. "Prodrugs. Do they have advantages in clinical practice?" *Drugs* 1985 29(5), 455-473.

Wu, K.-M. "A New Classification of Prodrugs: Regulatory Perspectives" *Pharmaceuticals* 2009 2(3), 77-81.

Pelicano, H.; Carney, D.; Huang, P. "ROS stress in cancer cells and therapeutic implications" *Drug Resist. Updates* 2004 7, 97-110.

Nagata, M. "Inflammatory cells and oxygen radicals" *Curr. Drug Targets Inflamm. Allergy* 2005 4(4), 503-504.

Haorah, S. H.; Ramirez, K.; Schall, D.; Smith, R.; Pandya, Y.; Persidsky, "Oxidative stress activates protein tyrosine kinase and matrix metalloproteinases leading to blood-brain barrier dysfunction" *J. Neurochem.* 2007 101, 566-576.

Rouffet, M.; Cohen, S. M. "Emerging Trends in Metalloprotein Inhibition" *Dalton Trans.* 2011, 40 3445-3454.

Major Jourden, J. L.; Cohen, S. M. "Hydrogen Peroxide Activated Matrix Metalloproteinase Inhibitors—A Prodrug Approach" *Angew. Chem. Intl. Ed.* 2010, 49, 6795-6797.

Dickens, M. G.; Franz, K. J. "A Prochelator Activated by Hydrogen Peroxide Prevents Metal-Induced Amyloid β Aggregation" *ChemBioChem* 2010 11(1), 59-62.

Messina, P.; Labbé, E.; Buriez, O.; Hillard, E. A.; Vessières, A.; Hamels, D.; Top, S.; Jaouen, G.; Frapart, Y. M.; Mansuy, D.; Amatore, C. "Deciphering the activation sequence of ferrociphenol anticancer drug candidates." *Chemistry* 2012 18(21): 6581-6587.

Evans, D. A.; Britton, T. C.; Ellman, J. A. "Contrasteric carboximide hydrolysis with lithium hydroperoxide" *Tet. Lett.* 1987 28(49) 6141-6144.

Crimmins, M. T.; King, B. W.; Tabet, A. E. "Asymmetric Aldol Additions with Titanium Enolates of Acyloxazolidinethiones: Dependence of Selectivity on Amine Base and Lewis Acid Stoichiometry". *J. Am. Chem. Soc.* 1997 119(33), 7883-7884.

Crimmins M. T.; Chaudhary K. "Titanium enolates of thiazolidinethione chiral auxiliaries: Versatile tools for asymmetric aldol additions." *Org. Lett.* 2000 2(6), 775-777.

Kurumbail, R. G.; Stevens, A. M.; Gierse, J. K.; McDonald, J. J.; Stegeman, R. A.; Pak, J. Y.; Gildehaus, D.; Miyashiro, J. M.; Penning, T. D.; Seibert, K.; Isakson, P. C.; Stallings, W. C. "Structural basis for selective inhibition of cyclooxygenase-2 by anti-inflammatory agents." *Nature* 1996 384, 644-648.

What is claimed is:

1. A compound of formula:

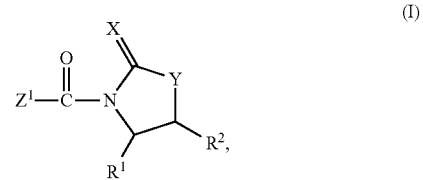

wherein
—C(O)Z$^1$ together form a drug moiety;
R$^1$ is hydrogen;
R$^2$ is independently hydrogen, halogen, —CCl$_3$, —CBr$_3$, —CF$_3$, —CI$_3$, —CN, —SH, —SO$_2$Cl, —SO$_{n2}$R$^{10}$, —SO$_{y2}$NR$^7$R$^8$, —NHNH$_2$, —ONR$^7$R$^8$, —NHC(O)NHNH$_2$, —NHC(O)NR$^7$R$^8$, —N(O)$_{m2}$, —NR$^7$R$^8$, —C(O)R$^9$, —C(O)—OR$^9$, —C(O)NR$^7$R$^8$, —OR$^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^7$, R$^8$, R$^9$, and R$^{10}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
Z$^1$ is a cyclooxygenase (COX) inhibitor drug moiety selected from the group consisting of an ibuprofen drug moiety, a dexibuprofen drug moiety, a naproxen drug moiety, a fenoprofen drug moiety, a ketoprofen drug moiety, a dexketoprofen drug moiety, a flurbiprofen drug moiety, an oxaprozin drug moiety, a loxoprofen drug moiety, an indomethacin drug moiety, a tolmetin drug moiety, a sulindac drug moiety, an etodolac drug moiety, a ketorolac drug moiety, a diclofenac drug moiety, a aceclofenac drug moiety, a mefenamic acid drug moiety, a meclofenamic acid drug moiety, a flufenamic acid drug moiety, a tolfenamic acid drug moiety, an acetylsalicylic acid drug moiety, a diflunisal drug moiety, a salsalate drug moiety, a choline magnesium trisalicylate drug moiety, and a licofelone drug moiety;
an integer from 0 to 2;
an integer from 1 to 2; and
an integer from 1 to 2.

2. The compound of claim 1, wherein said COX inhibitor drug moiety is an ibuprofen drug moiety, a dexibuprofen drug moiety, a naproxen drug moiety, a fenoprofen drug moiety, a ketoprofen drug moiety, a dexketoprofen drug moiety, a flurbiprofen drug moiety, an oxaprozin drug moiety, or a loxoprofen drug moiety.

3. The compound of claim 1, wherein the COX inhibitor drug moiety is an indomethacin drug moiety, a tolmetin drug moiety, a sulindac drug moiety, an etodolac drug moiety, a ketorolac drug moiety, a diclofenac drug moiety, a aceclofenac drug moiety, a mefenamic acid drug moiety, a meclofenamic acid drug moiety, a flufenamic acid drug moiety, a tolfenamic acid drug moiety, an acetylsalicylic acid drug moiety, a diflunisal drug moiety, a salsalate drug moiety, a choline magnesium trisalicylate drug moiety, or a licofelone drug moiety.

4. A pharmaceutical composition comprising a compound of claim 1 and a pharmaceutically acceptable excipient.

* * * * *